US012755831B2

(12) United States Patent
Furkel et al.

(10) Patent No.: US 12,755,831 B2
(45) Date of Patent: Oct. 6, 2026

(54) SINGLE-CELL MORPHOLOGY ANALYSIS FOR DISEASE PROFILING AND DRUG DISCOVERY

(71) Applicant: Universität Heidelberg, Heidelberg (DE)

(72) Inventors: Jennifer S. Furkel, Heidelberg (DE); Maximilian-Werner Knoll, Heidelberg (DE); Hugo A. Katus, Heidelberg (DE); Mathias Konstandin, Heidelberg (DE)

(73) Assignee: UNIVERSITÄT HEIDELBERG, Heidelberg (DE)

( * ) Notice: Subject to any disclaimer, the term of this patent is extended or adjusted under 35 U.S.C. 154(b) by 724 days.

(21) Appl. No.: 17/923,121

(22) PCT Filed: May 14, 2021

(86) PCT No.: PCT/EP2021/062878
§ 371 (c)(1),
(2) Date: Nov. 3, 2022

(87) PCT Pub. No.: WO2021/229079
PCT Pub. Date: Nov. 18, 2021

(65) Prior Publication Data

US 2023/0352149 A1 Nov. 2, 2023

(30) Foreign Application Priority Data

May 14, 2020 (EP) .................................... 20174777

(51) Int. Cl.
*G01N 33/50* (2006.01)
*G16H 20/10* (2018.01)
*G16H 30/40* (2018.01)

(52) U.S. Cl.
CPC ......... *G16H 30/40* (2018.01); *G01N 33/5044* (2013.01); *G16H 20/10* (2018.01); *G01N 2800/32* (2013.01); *G01N 2800/52* (2013.01)

(58) Field of Classification Search
CPC ............... G16H 20/10; G01N 33/5044; G01N 2800/32; G01N 2800/52
(Continued)

(56) References Cited

U.S. PATENT DOCUMENTS

2003/0113301 A1* 6/2003 Edge .................... C12N 5/0657 424/93.21
2009/0170091 A1* 7/2009 Giuliano ............ G01N 33/5008 435/6.14
(Continued)

OTHER PUBLICATIONS

Christian Scheeder et al., "Machine learning and image-based profiling in drug discovery," Current Opinion in Systems Biology, vol. 10, pp. 43-52, May 26, 2018.
(Continued)

*Primary Examiner* — Jamares Q Washington
(74) *Attorney, Agent, or Firm* — MARSHALL, GERSTEIN & BORUN LLP

(57) ABSTRACT

The present invention provides method of studying an effect of a test substance on a test sample of bio-logical cells using a set of relevant parameters and a set of meta-features, the method comprising:

Figure 1:
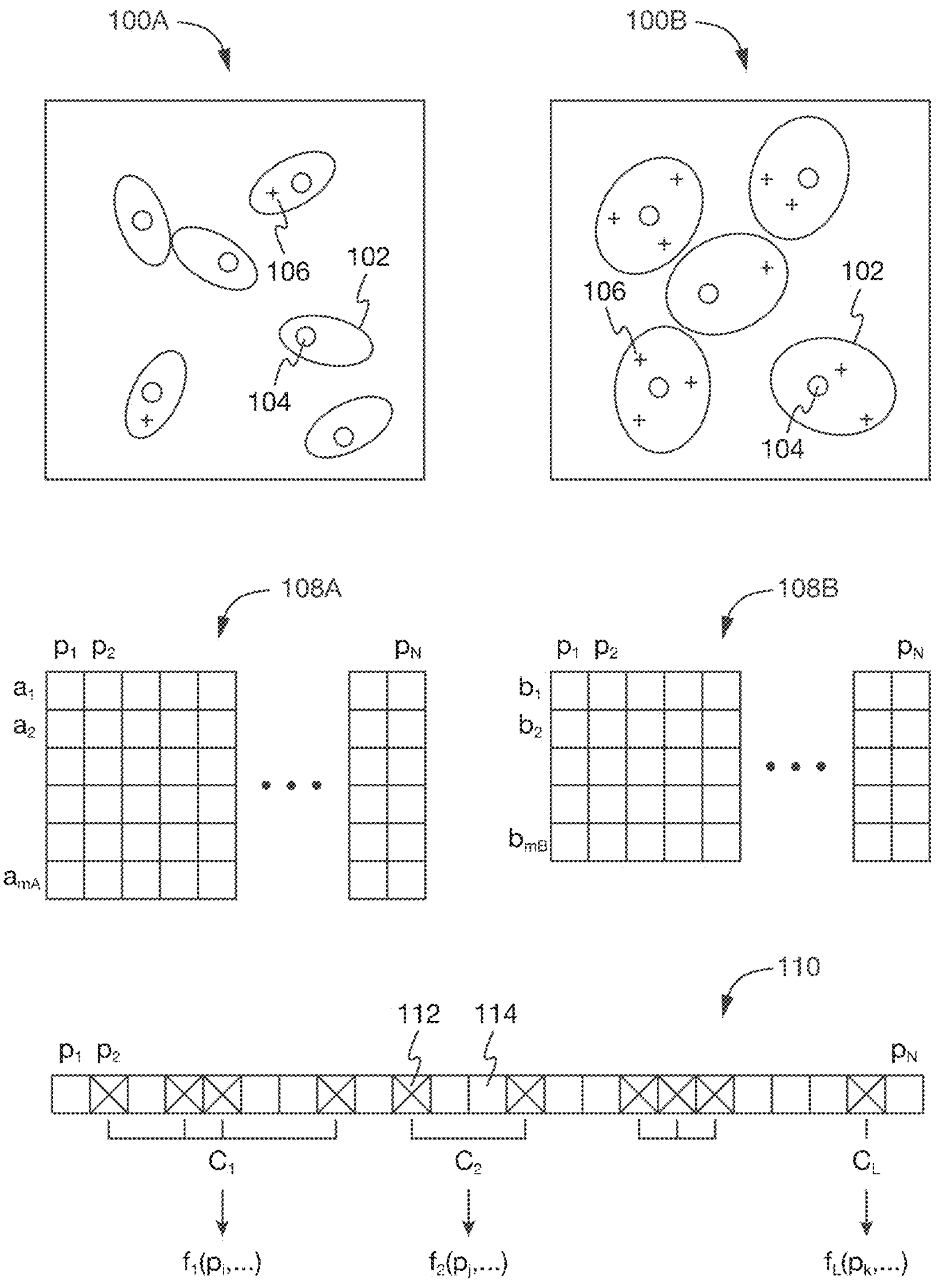

exposing the test sample to the test substance;

determining parameter values of the set of relevant parameters for each of a plurality of cells in the test sample; and determining feature values of the set of meta-features for the test sample, wherein each of the feature values is calculated from the parameter values of a cluster of correlated parameters from the set of relevant parameters that is associated with the respective meta-feature, wherein a reference sample for determining the set of meta-features was exposed to a stimulus substance.

16 Claims, 45 Drawing Sheets

(58) Field of Classification Search
USPC .......................................... 382/128, 133, 134
See application file for complete search history.

(56) References Cited

U.S. PATENT DOCUMENTS

| | | | | |
|---|---|---|---|---|
| 2011/0169937 | A1* | 7/2011 | McLaughlin | G16C 20/70<br>382/133 |
| 2012/0164669 | A1* | 6/2012 | Hess | G01N 33/6893<br>435/7.94 |
| 2017/0307596 | A1* | 10/2017 | Coyne | C12N 5/0696 |

OTHER PUBLICATIONS

Vebjorn Ljosa et al., "Comparision of Methods for Image-Based Profiling of Cellular Morphological Responses to Small-Molecule Treatment," Journal of Biomolecular Screening, vol. 18, No. 10, pp. 1321-1329, Sep. 17, 2013.
Loo Lit-Hsin et al., "IMage-based multivariate profiling of drug responses from single cells," Nature Methods, Nature Pub. Group, New York, vol. 4, No. 5, pp. 445-453, Apr. 1, 2007.
Matthew D. Sutcliffe et al., "High content analysis identifies unique morphological features of reprogrammed cardiomyocytes," Scientific Reports, vol. 8, No. 1, Jan. 19, 2018.

* cited by examiner

C

| | amyloidosis | aortic stenosis | DCM | hyp cmp | ICMP | hypertension |
|---|---|---|---|---|---|---|
| *test* | 9 | 6 | 3 | 4 | 2 | 3 |
| *train* | 20 | 12 | 6 | 7 | 4 | 7 |

A lower 95% CI (Wilson)

| | Pe | NE | A | Iso | Ins | ET | AT |
|---|---|---|---|---|---|---|---|
| *Pe* | 94 | 25 | 11 | 11 | 13 | 1 | 1 |
| *NE* | 25 | 235 | 35 | 94 | 42 | 2 | 5 |
| *A* | 11 | 35 | 157 | 53 | 11 | 1 | 2 |
| *Iso* | 11 | 94 | 53 | 227 | 44 | 0 | 0 |
| *Ins* | 13 | 42 | 11 | 44 | 115 | 0 | 0 |
| *ET* | 1 | 2 | 1 | 0 | 0 | 34 | 1 |
| *AT* | 1 | 5 | 2 | 0 | 0 | 1 | 16 |

Number of features

| | Pe | NE | A | Iso | Ins | ET | AT |
|---|---|---|---|---|---|---|---|
| *Pe* | 112 | 35 | 18 | 18 | 20 | 2 | 2 |
| *NE* | 35 | 259 | 46 | 112 | 54 | 5 | 9 |
| *A* | 18 | 46 | 178 | 67 | 17 | 3 | 4 |
| *Iso* | 18 | 112 | 67 | 251 | 57 | 1 | 1 |
| *Ins* | 20 | 54 | 17 | 57 | 134 | 0 | 1 |
| *ET* | 2 | 5 | 3 | 1 | 0 | 45 | 2 |
| *AT* | 2 | 9 | 4 | 1 | 1 | 2 | 24 |

upper 95% CI (Wilson)

| | Pe | NE | A | Iso | Ins | ET | AT |
|---|---|---|---|---|---|---|---|
| *Pe* | 132 | 48 | 28 | 28 | 31 | 7 | 7 |
| *NE* | 48 | 284 | 61 | 132 | 69 | 12 | 17 |
| *A* | 28 | 61 | 201 | 84 | 27 | 9 | 10 |
| *Iso* | 28 | 132 | 84 | 276 | 73 | 6 | 6 |
| *Ins* | 31 | 69 | 27 | 73 | 155 | 4 | 6 |
| *ET* | 7 | 12 | 9 | 6 | 4 | 59 | 7 |
| *AT* | 7 | 17 | 10 | 6 | 6 | 7 | 35 |

Fig. 25A

```
basedir/
 |
 *-- run1/
 |    |
 |    *-- plate1/
 |    |    |
 |    |    *-- Cells.txt
 |    |    |
 |    |    *-- Primarieswithoutborder.txt
 |    |    |
 |    |    *-- Cytoplasm.txt
 |    |    |
 |    |    *-- Treatment.csv
 |    |
 |    *-- plate2/
 |    |    |
 |    |    *-- ...
 |    |
 |    *-- plate3/
 |         |
 |         *-- ...
 |
 *-- run2/
      |
      *-- plate1/
      |    |
      |    *-- ...
      |
      *-- plate2/
      |    |
      |    *-- ...
      |
      *-- plate3/
           |
           *-- ...
```

Fig.28 plate treatment layout

| | 1 | 2 | 3 | 4 | 5 | 6 | 7 | 8 | 9 | 10 | 11 | 12 |
|---|---|---|---|---|---|---|---|---|---|---|---|---|
| A | Ko_1 | Ko_1 | Ko_1 | Ko_1 | Ko_1 | Ko_1 | Ko_1 | Ko_1 | Ko_1 | Ko_1 | Ko_1 | Ko_1 |
| B | A_1 | A_1 | A_1 | A_1 | A_1 | A_1 | A_2 | A_2 | A_2 | A_2 | A_2 | A_2 |
| C | A_3 | | A_3 | A_3 | A_3 | A_3 | D_3 | D_3 | D_3 | D_3 | D_3 | D_3 |
| D | D_1 | D_1 | D_1 | D_1 | D_1 | D_1 | D_2 | D_2 | D_2 | D_2 | D_2 | D_2 |
| E | Pe_1 | Pe_1 | Pe_1 | Pe_1 | Pe_1 | Pe_1 | Pe_2 | Pe_2 | Pe_2 | Pe_2 | Pe_2 | Pe_2 |
| F | Pe_3 | Pe_3 | Pe_3 | Pe_3 | Pe_3 | Pe_3 | Ins_3 | Ins_3 | Ins_3 | Ins_3 | Ins_3 | Ins_3 |
| G | Ins_1 | Ins_1 | Ins_1 | Ins_1 | Ins_1 | Ins_1 | Ins_2 | Ins_2 | Ins_2 | Ins_2 | Ins_2 | Ins_2 |
| H | Si_1 | Si_1 | Si_1 | Si_1 | Si_1 | Si_1 | Sc_1 | Sc_1 | Sc_1 | Sc_1 | Sc_1 | Sc_1 |

SINGLE-CELL MORPHOLOGY ANALYSIS FOR DISEASE PROFILING AND DRUG DISCOVERY

FIELD OF THE INVENTION

The present invention is in the field of medical diagnostics and pharmacology. In particular, the invention relates to a method of determining a set of meta-features for comparing samples of biological cells and a method of studying an effect of a test substance on a test sample of biological cells using a set of meta-features.

BACKGROUND

The automated analysis of microscopic images of cell samples allows for rapidly extracting a plurality of morphological parameters on the single-cell level for large numbers of samples, see e.g. A. E. Carpenter et al., *Genome Biol.*, 7(10):R100 (2006). Such high-content techniques may be used for a wide variety of applications in life sciences and medicine, ranging from basic pharmacological research to personalized medicine. High-throughput image-based screening may for example be employed to study the effects of drugs on cell cultures, see e.g. Z. E. Perlman et al., *Science* 5699, 1194-1198 (2004) and L.-H. Loo et al., *Nat. Methods* 4,445-453 (2007). In oncology, automated morphological assessments are for example being used to predict treatment responses to chemotherapeutic therapies, see e.g. B. Snijder et al., *The Lancet Haematology* 4(12): p. e595-e606 (2017) and K. Gorshkov et al., *Drug discovery today* 24(1): p. 272-278 (2019).

These techniques also hold great potential for the study and treatment of cardiovascular diseases. Many of these conditions are associated with cardiac hypertrophy as cardiomyocytes grow in size in response to increased stress. This may for example be detected in microscopic images by analyzing changes in geometrical cell parameters such as the cell surface area, the cell perimeter or the cell form factor, see e.g. K. A. Ryall et al., *J. Mol. Cell. Cardiol.* 72, 74-84 (2014). By increasing the number of accessible parameters and due to their potential for fast and efficient automation, high-content morphological analyses might thus allow for an improved assessment of the effect of a given substance on samples of heart cells. This may for example be useful for testing candidate substances for the development of novel drugs. Furthermore, this approach could provide a powerful diagnostic tool for assessing the risk of developing certain cardiovascular conditions as well as for assessing the response to a therapeutic treatment. EP 2 954 322 A1, for example, describes a method, in which a sample of cardiomyocytes is exposed to blood plasma of a patient and the effect thereof is analyzed for diagnostic purposes.

In contrast to oncological settings, however, in vitro models in cardiovascular research such as primary neonatal rat cardiomyocytes (NRCM) or inducible progenitor derived cardiomyocytes (hiPSC-CM) are heterogeneous cell populations, which intrinsically exhibit large variations in parameters such as the cell size. This poses considerable challenges for extracting meaningful information from parameters on the single-cell level and in particular for automated high-content analyses.

SUMMARY OF THE INVENTION

The object of the invention is thus to enable the high-content morphological analysis of heterogeneous cell populations for studying the effect of substances on cell samples for disease profiling and drug discovery.

This object is met by a method according to claim 1, a computer program product according to claim 14, and a system according to claim 15. Embodiments of the present invention are detailed in the dependent claims.

In particular, the present invention provides a method of studying an effect of a test substance on a test sample of biological cells using a set of relevant parameters and a set of meta-features, the method comprising: exposing the test sample to the test substance; determining parameter values of the set of relevant parameters for each of a plurality of cells in the test sample; and determining feature values of the set of meta-features for the test sample, wherein each of the feature values is calculated from the parameter values of a cluster of correlated parameters from the set of relevant parameters that is associated with the respective meta-feature, wherein the reference sample for determining the set of meta-features was exposed to a stimulus substance.

Preferably, the stimulus substance is a mediator involved in one or more medical conditions, in particular in one or more cardiovascular conditions.

Preferably, the set of relevant parameters and the set of meta-features are determined by: receiving parameter values of a set of cell parameters for each of a plurality of cells in a control sample and for each of a plurality of cells in a reference sample; identifying a set of relevant parameters from the set of cell parameters by comparing the parameter values from the control sample and the parameter values from the reference sample for at least one of the cell parameters; identifying clusters of correlated parameters within the set of relevant parameters based on correlations between the parameter values of the relevant parameters; and defining a meta-feature for at least one of the clusters as a mathematical function of the parameters of the respective cluster.

Preferably, the method further comprises: determining parameter values of the set of relevant parameters for each of a plurality of cells in a control test sample; determining feature values of the set of meta-features from the parameter values of the set of relevant parameters for the control test sample; and comparing feature values of meta-features for the test sample and feature values of meta-features for the control test sample to assess the effect of the test substance.

In a preferred embodiment, the biological cells are cardiomyocytes and the stimulus substance comprises a hypertrophy inducing substance, in particular at least one of phenylephrine, adrenaline, noradrenaline, isoproterenol, insulin, endothelin, and angiotensin, and/or the test substance comprises a candidate substance to be tested as a potential inhibitor of the medical condition. Experiments have shown that the presented method is particularly useful for analyzing cardiomyocytes.

Preferably, the test substance comprises patient-specific material, in particular blood and/or human-induced pluripotent stem cell-derived cardiomyocytes, iPSC-CMs, in combination with one or more pharmacological substances.

Preferably, the test substance comprises a sample of a patient, in particular a blood sample of the patient, preferably blood serum or blood plasma of the patient, wherein the method preferably further comprises diagnosing a medical condition, and/or assessing a progress of a therapeutic treatment against the medical condition based on the feature values of the set of meta-features for the test sample, in particular wherein the medical condition is hypertrophic cardiomyopathy, amyloidosis and/or aortic stenosis.

Preferably, the method is used to distinguish different cell types, in particular to distinguish one or more of: fibroblast, cardiomyocyte, immune cell, or others, and/or to distinguish different cell sub-types, in particular one or more of cardiomyocyte subtype 1 and cardiomyocyte subtype 2.

Optionally, the method is a method for assessing suitability of therapeutic treatments for an individual patient, in particular regarding treatment efficacy, adverse events, time to treatment response, wherein preferably the method is used for continuous therapeutic monitoring.

Optionally, the method further comprises performing a single-cell phenotyping by determining feature values of the set of meta-features and/or parameter values of the set of relevant parameters for at least one of the plurality of cells in the test sample, and/or performing a population-level phenotyping by determining average feature values of the set of meta-features and/or average parameter values of the set of relevant parameters averaged over a set of cells from the plurality of cells in the test sample.

Preferably, the plurality of cells include one or more of one or more cells extracted from mammalian hearts, in particular whole heart lysate cells, cardiomyocytes, fibroblasts, immune cells, and/or mammalian stem-cell derived cardiomyocytes, in particular human induced pluripotent stem cell-derived cardiomyocytes.

Preferably, determining parameter values of the set of relevant parameters for each of a plurality of cells in the test sample comprises obtaining a plurality of images of the plurality of cells at a plurality of time points, wherein in particular the plurality of images are obtained using a microscope. For example, a video camera may be used to obtain the images a multiple time points.

The method may further comprise an initial step of staining or labelling the biological cells, a cell compartment, a cell structure, a specific protein or mRNA of interest and/or the test substance with a stain or dye or with an imaging marker, e.g. a fluorescent marker. This is advantageous in particular in the context of temporal imaging.

The present invention further provides a computer program product comprising a set of machine-readable instructions executable by a processing device, wherein the instructions cause the processing device to execute the presented method.

The present invention further provides system comprising a processing device and a data storage coupled to the processing device, wherein the data storage stores a set of machine-readable instructions that, when executed by the processing device, cause the processing device to: receive at least one microscopic image of a test sample of biological cells and at least one microscopic image of a control test sample of biological cells; determine parameter values of a set of relevant parameters for each of a plurality of cells in the test sample and for each of a plurality of cells in the control test sample from the at least one microscopic image of the respective sample; determine feature values of a set of meta-features from the parameter values of the set of relevant parameters for the test sample; and determine feature values for the set of meta-features from the parameter values of the set of relevant parameters for the control test sample, wherein the system preferably further comprises the test sample and the control test sample, wherein the test sample is to be exposed to a test substance.

Preferably, the system is configured such that the set of relevant parameters and the set of meta-features were determined by: receiving parameter values of a set of cell parameters for each of a plurality of cells in a control sample and for each of a plurality of cells in a reference sample; identifying a set of relevant parameters from the set of cell parameters by comparing the parameter values from the control sample and the parameter values from the reference sample for at least one of the cell parameters; identifying clusters of correlated parameters within the set of relevant parameters based on correlations between the parameter values of the relevant parameters; and defining a meta-feature for at least one of the clusters as a mathematical function of the parameters of the respective cluster.

The present invention further provides a method of determining a set of meta-features for comparing samples of biological cells, the method comprising: (1) receiving parameter values of a set of cell parameters for each of a plurality of cells in a control sample and for each of a plurality of cells in a reference sample; (2) identifying a set of relevant parameters from the set of cell parameters by comparing the parameter values from the control sample and the parameter values from the reference sample for at least one of the cell parameters; (3) identifying clusters of correlated parameters within the set of relevant parameters based on correlations between the parameter values of the relevant parameters; and (4) defining a meta-feature for at least one of the clusters as a mathematical function of the parameters of the respective cluster. The above numbering as well as any similar numbering in the context of this disclosure are for clarity only and do not imply a certain order of execution. As far as technically feasible, this method as well as other methods or sets of instructions described herein may be executed in an arbitrary order and steps thereof may in particular be executed simultaneously at least in part.

Each of the control and reference samples may comprise a large number of cells, for example more than 100 cells, in one example between $10^3$ and $10^6$ cells. In some examples, one or both of the control and reference samples may comprise two or more subsamples, which may for example be wells on one or more multi-well plates. Preferably, the control and reference samples comprise the same types of cells. The control and reference samples may in particular comprise cells derived from the same cell type. In some embodiments, the control and reference samples comprise cells of a single type and/or derived from a single cell line, in other embodiments the control sample and/or the reference sample comprises cells of multiple types and/or cells derived from multiple cell lines. The cells may for example be heart cells and may in particular comprise cells of one or more cell types selected from the group consisting of cardiomyocytes, endothelial cells, leukocytes, fibroblasts, peri-vascular cells, macrophages, and/or cardiac progenitor cells. The cells may for example be derived from one or more immortalized cell lines and/or may comprise immature and mature heart cells, e.g. human induced pluripotent stem cell derived cardiomyocytes (hiPSC-CMs). In some embodiments, cells in the reference sample and/or in the control sample may exhibit one or more specific mutations, e.g. a mutation that is known or suspected to be associated with a medical condition.

The cell parameters are parameters that characterize one or more properties associated with a single cell, in particular morphological properties associated with a single cell, e.g. as detailed below. The set of cell parameters may be a set of pre-defined parameters. In some examples, the set of cell parameter may also comprise or consist of unknown parameters, i.e. the parameter values may be received without knowing the meaning or definition of the respective parameters. For example, at least some of the cell parameter values may have been determined using a neural network, e.g. a convolutional neural network for analyzing microscopic images of the samples. The set of cell parameters may comprise a large number of parameters, for example more than 100 parameters, in one example between 1000 and 5000 parameters. The parameter values may be received for each of the cells in the control and/or reference samples or for a subset of cells in the control and/or reference samples.

The parameter values from the reference sample are compared to the respective parameter values from the control sample for at least one cell parameter, preferably for a plurality of cell parameters, in one example for all of the cell parameters. Comparing the parameter values for a cell parameter may for example comprise comparing the mean or median value of the respective parameter values in the reference sample or in a part thereof to the mean or median value in the control sample or in a part thereof and/or comparing a distribution of the respective parameter values in the reference sample or in a part thereof to the distribution in the control sample or in a part thereof, e.g. as detailed below. Based on this comparison, a set of relevant parameters is determined from the set of cell parameters, for example by selecting parameters fulfilling one or more pre-defined conditions pertaining to the comparison, e.g. as detailed below.

Correlations between the parameter values of the relevant parameters are evaluated, for example correlations over a set of cells in the control and/or reference samples, in one example over all cells in the control and/or reference samples. This may comprise determining a correlation metric for pairs and/or groups of relevant parameters, wherein the correlation metric quantifies a degree of correlation or similarity between the respective parameters. Based on the correlations, clusters of correlated parameters are identified, e.g. groups of parameters for which the correlation metric fulfills one or more pre-defined conditions, for example exceeds a pre-defined threshold. This may comprise using one or more clustering algorithms, e.g. as detailed below. Each of the clusters may comprise a different number of relevant parameters. In some examples, at least one of the clusters may only contain a single relevant parameter.

For at least one of the clusters, a meta-feature is defined, wherein the meta-feature is a mathematical function of the relevant parameters of the respective cluster. Accordingly, a feature value of the meta-feature may be calculated for each cell from the parameter values of the corresponding parameters for the respective cell. The meta-feature may for example be defined as the mean or median of the relevant parameters of the respective cluster, wherein the parameters may be normalized, standardized, and/or weighted beforehand in some examples. The meta-feature does not depend on parameters that are not contained in the respective cluster. Preferably, a meta-feature is defined for each of the clusters.

The method according to the invention thus allows for determining a set of meta-features, which may subsequently be used to compare other samples of cells, e.g. a pair of samples different from the control and reference samples. By identifying relevant parameters based on a comparison between the control and reference samples, situation-specific parameters may be extracted from a large number of initial parameters, for example by exposing one of the samples to a certain substance or treatment. Furthermore, aggregating relevant parameters to a smaller number of meta-features provides a robust and efficient way for comparing samples of cells, e.g. to assess the significance of differences between the samples, and facilitates interpretation and understanding of the data. Thereby, the method according to the invention allows for extracting meaningful information from single-cell morphology analyses even for heterogeneous cell populations such as cardiomyocytes. This may in particular be used for automated drug screening as well as for diagnostic purposes, for example by exposing one of the control and reference samples to a mediator involved in one or more medical conditions as detailed below. Furthermore, at least some of the method steps may be implemented using machine learning techniques such as artificial neural networks, e.g. for identifying the set of relevant parameters and/or for identifying the clusters of correlated parameters.

A related two-step approach comprising an identification of informative parameters and a clustering thereof is known from W. D. Anderson et al., *Front. Cell. Neurosci.* 11:233 (2017), which involves an approximate decomposition of a parameter value matrix by nonnegative matrix factorization to identify parameter clusters for illustrative purposes.

In a preferred embodiment, the reference sample was exposed to a reference substance prior to determining the parameter values of the cell parameters. The reference substance may for example have a functional, physiological, pathological, and/or morphological effect on cells in the reference sample. Preferably, the reference substance comprises a stimulus substance that is a mediator involved in one or more medical conditions, in particular one or more cardiovascular conditions. As used herein, a mediator may refer to any substance with a known or suspected effect on cells that is associated with the respective medical condition, in particular a substance or effect that is known or suspected to be involved in the development of the medical condition. This may for example allow for defining meta-features that are associated with a certain kind of medical condition, which in turn may allow for an efficient screening of potential inhibitors of the respective condition or of risk factors associated therewith as well as for an efficient diagnosis or risk assessment for the respective condition. In some examples, the reference substance and/or the stimulus substance may comprise a plurality of substances. In one example, the stimulus substance comprises a hypertrophy inducing substance, in particular at least one of phenylephrine, adrenaline, noradrenaline, isoproterenol, insulin, endothelin, and angiotensin. In some examples, the reference substance may comprise at least one substance in addition to the stimulus substance, e.g. an inhibiting substance as detailed below.

In some embodiments, the reference sample may comprise a plurality of individual samples. Each of the individual samples may for example have been exposed to a different dose of the reference substance, e.g. to a different concentration of the reference substance and/or for a different duration. Comparing the parameter values from the control sample and the parameter values from the reference sample may comprise modelling a dose dependency of an effect of the reference substance on the respective parameter. For this, a statistical model may be used, e.g. a model assuming a certain functional dependence on the dose, on the concentration, and/or on the duration. In one example, a model assuming a linear dependence on the dose, on the concentration, and/or on the duration may be used. Preferably, a mixed error-component model is used. For example, some or all of the individual samples may comprise two or more subsamples, e.g. wells on one or more multi-well plates in one or more experimental runs, wherein the subsamples, plates, and/or experimental runs may be treated as random variables and the dose, the concentration, and/or the duration as fixed variables.

Preferably, comparing the parameter values from the control and reference samples comprises determining a significance measure for at least one of the cell parameters, in some examples for a plurality of cell parameters, in one example for all of the cell parameters. The significance measure characterizes a statistical significance of a difference or equivalence between the respective parameter values in the control sample and the respective parameter values in the reference sample. In other words, the significance measure may quantify to which degree of certainty the parameter values in the control and reference sample are different or are the same, i.e. whether or not the parameter values allow for concluding that the samples are different or not different in this regard. The significance measure may for example characterize the statistical significance of the difference or equivalence between a mean or median of the respective parameter values in the control sample and a mean or median of the respective parameters in the reference sample, wherein the mean or median may be obtained from each of the plurality of cells in the respective sample or a part thereof. The significance measure may for example quantify an error, in particular a statistical error such as a standard deviation, or a confidence interval of the difference between the means or medians. The significance measure may in particular be a measure for null hypothesis testing, e.g. a p-value. In embodiments, in which a dose dependency is modelled, the significance measure may quantify the statistical significance of the assumed dose dependency and may e.g. be a measure for the goodness of fit of the statistical model, for example a fit error.

The relevant parameters may be identified based on the significance measure of the at least one cell parameter. In some examples, all parameters for which the significance measure indicates significance, e.g. is above or below a pre-defined threshold, are selected as relevant parameters, whereas all parameters for which the significance measure does not indicate significance are not included in the set of relevant parameters. Accordingly, the significance measure may for example be used to identify cell parameters exhibiting a statistically significant difference between the control and reference samples, e.g. due to an effect of the reference substance, or to identify cell parameters exhibiting a statistically significant equivalence between the control and reference samples. The latter may for example be of interest if the reference substance comprises an inhibiting substance such as a potential inhibitor for a medical condition in addition to a stimulus substance being a mediator involved in the medical condition.

In some embodiments, comparing the parameter values from the control and reference samples may also comprise determining a validity measure for the at least one cell parameter. The validity measures may for example be obtained by performing a statistical cross-validation of a statistical model for the respective cell parameter, e.g. an exhaustive or non-exhaustive cross-validation using subsets of cells in the control and reference samples. The statistical model may for example predict a difference between the respective parameter values in the control sample and in the reference sample based on the data from one or more subsets. The subsets may e.g. comprise a pre-defined number of cells in the respective sample, a pre-defined portion or fraction of the respective sample, and/or a pre-defined number of subsamples in the respective sample. In some examples, a non-exhaustive k-fold cross-validation may be performed using subsets, each of which comprises one or more wells on multi-well plates. The validity measure may for example quantify a mean prediction error of the cross-validation averaged over a plurality of permutations of subsets.

The relevant parameters may be identified based on the significance measure and the validity measure of the at least one cell parameter. In some examples, all parameters for which the significance measure indicates significance and the validity measure indicates validity, e.g. both measures are above or below a respective pre-defined threshold, are selected as relevant parameters, whereas all parameters for which the significance measure does not indicate significance and/or the validity measure does not indicate validity are not included in the set of relevant parameters.

In some examples, identifying the set of relevant parameters may further comprise a multiplicity adjustment of the significance measure and/or of the validity measure to reduce the number of falsely identified relevant parameters. This may comprise an adjustment based on a false discovery rate (FDR), e.g. using the Benjamini-Hochberg method, and/or on a family-wise error rate (FWER), e.g. using the Bonferroni method.

The clusters of correlated parameters are identified by performing a cluster analysis on the relevant parameters. In a preferred embodiment, the clusters of correlated parameters are identified by performing a hierarchical cluster analysis on the relevant parameters. Additionally or alternatively, other cluster analyses may be performed, for example a centroid-based clustering such as k-means clustering, a density-based clustering, and/or a distribution-based clustering. In some embodiments, a neural network-based clustering may be used, e.g. using unsupervised machine learning. For the hierarchical cluster analysis, a similarity metric and a linkage criterion may be used for building up the clusters. The similarity metric may e.g. be the Euclidean distance or the squared Euclidean distance of the parameter values over the set of cells in the control and/or reference samples taken into account for clustering. The linkage criterion may for example be based on a minimum or average distance between parameters in clusters and/or on an intra-cluster variance. The clustering method may e.g. be Ward's minimum variance method (for example ward.D or ward.D2 clustering in the R programming language), complete-linkage clustering, or average-linkage clustering (for example weighted or unweighted pair group method with arithmetic mean (WPGMA/UPGMA) clustering). To determine the number of clusters, a predetermined cutoff quantifying a maximum degree of intra-cluster variability may be used, for example a predetermined cutoff for the intra-cluster variance or the intra-cluster median absolute deviation. In some embodiments, the cutoff may not be predetermined, but the method may comprise determining the cutoff, e.g. based on an evolution of the degree of intra-cluster variability with the number of clusters.

The set of cell parameters may for example comprise at least one geometrical cell parameter characterizing the size and/or shape of the respective cell or of a part thereof. The at least one geometrical cell parameter may e.g. comprise one or more parameters selected from the group consisting of a volume of the cell, a cross-sectional area of the cell, a surface area of the cell, a perimeter of the cell, an eccentricity of the cell, an aspect ratio of the cell, a second moment of area of the cell, an orientation of the cell, and corresponding parameters for parts of the cell such as the nucleus.

Additionally or alternatively, the set of cell parameters may comprise at least one structural parameter characterizing a structure and/or topography of the respective cell or of a part thereof. A structural parameter may for example quantify a spatial variability or spatial correlations in the cell or a part thereof, for example a roughness of a membrane of the cell or a spatial variability of a cytoplasm compartment and/or of a nuclear compartment of the cell. In some examples, the cell parameters may for example have been obtained from microscopic images of the samples, e.g. as detailed below, and a structural parameter may e.g. quantify a contrast, a variance of the measured intensity within the cell or a part thereof or a correlation length of the measured intensity within the cell or a part thereof. A structural parameter may further quantify other intensity-related properties, e.g. a mean intensity, a minimum intensity or a maximum intensity within the cell or a part thereof.

Additionally or alternatively, the set of cell parameters may comprise at least one functional parameter characterizing a concentration and/or a distribution of one or more biomolecules and/or of one or more biochemical substances in the respective cell or in a part thereof. Such parameters may for example have been obtained by staining or labelling the respective biomolecule or substance with a stain or dye or with an imaging marker, e.g. a fluorescent marker. Additionally or alternatively, some or all of the parameters may e.g. have been obtained from the auto-fluorescence of the biomolecule or biochemical substance. Accordingly, a functional parameter may for example quantify a spatially integrated intensity of the respective fluorescence light within the cell or a part thereof or a ratio of the spatially integrated intensity in different parts of the cell, e.g. inside and outside of the cell's nucleus. The biomolecules may for example be proteins, peptides, DNA, RNA, antibodies, amino acids, lipids, fatty acids, saccarides, carbohydrates, other metabolites, and/or a product of an assay such as an enzyme-linked immunosorbent assay or a proximity ligation assay. The biomolecules may in particular be biomolecules involved in a cellular signaling pathway, e.g. a transcription factor such as nuclear factor of activated T-cells (NFAT), myocyte-specific enhancer factor 2C (MEF2C), atrial natriuretic peptide (ANP), and/or GATA-4.

Additionally or alternatively, the set of cell parameters may comprise at least one proximity parameter associated with one or more cells in the vicinity of the respective cell. The at least one proximity parameter may e.g. comprise one or more parameters selected from the group consisting of a number of cells within a predefined radius around the cell, a number of neighboring cells touching the cell, a fraction of the membrane of the cell in contact with neighboring cells, a mean distance to neighboring cells, and parameters based on cell parameters of neighboring cells.

Additionally or alternatively, the set of cell parameters may comprise at least one machine vision parameter extracted from an image of the respective cell or of a part thereof using a neural network. The machine vision parameter may for example correspond to or be associated with one or more outputs of a neural network, in particular a convolutional neural network, which may e.g. be used to analyze a microscopic image of the respective sample. In some examples, the meaning of the machine vision parameter may not be known, i.e. there may not be a straightforward interpretation in terms of morphological cell features.

In a preferred embodiment, the method may further comprise determining a parameter value of a secondary cell parameter for each of the plurality of cells in the control sample and for each of the plurality of cells in the reference sample. The parameter value of the secondary parameter is determined based on the parameter values of the set of cell parameters for the respective cell. The secondary cell parameter may be added to the set of cell parameters, e.g. prior to identifying the relevant parameters. The secondary parameter may for example be an average, a difference, or a ratio of two or more parameters from the set of cell parameters. In other examples, the secondary parameter may e.g. be a categorization parameter assigning the respective cell to one of a plurality of categories based on the parameter values. The categorization parameter may for example be determined by comparing one or more cell parameters to respective thresholds. In some embodiments, the method may comprise defining these thresholds, e.g. based on a distribution of the respective cell parameter over a set of cells. This may for example comprise determining a minimum, a maximum, and/or a width in the distribution of the respective cell parameter. In some embodiments, a plurality of secondary parameters may be determined and added to the set of cell parameters.

In a preferred embodiment, the secondary parameter is a categorization parameter that characterizes a cell type or a state of the cell. In one example, the secondary parameter indicates whether the respective cell is of a certain type, e.g. a cardiomyocyte or not, for example based on thresholds for geometrical, structural, and/or functional parameters. In another example, the secondary parameter characterizes a cell cycle state of the cell, e.g. based on a threshold for a functional parameter such as a parameter associated with a density or distribution of DNA in the cell or in a part thereof. In yet another example, the secondary parameter characterizes whether a cell is intact or not, e.g. based on a threshold for a ratio between the cross-sectional area of the cell and of the nucleus. Accordingly, the respective secondary parameters may for example allow for identifying apoptotic cells, non-intact cells and/or cells not matching a predetermined cell type.

In some embodiments, the method further comprises selecting a subset of cells from the plurality of cells in the control sample and/or in the reference sample based on the parameter values, e.g. prior to identifying the relevant parameters. This may for example comprise excluding cells from the selected subset for which one or more parameter values are missing, e.g. since the respective cell is at a border of microscopic image. Selecting the subset of cells may in particular comprise identifying apoptotic cells, non-intact cells and/or cells not matching a predetermined cell type based on the parameter values, in particular based on parameter values of one or more secondary parameters, and excluding the respective cells from the selected subset. In some examples, only the selected subset may be used for further analysis, e.g. to identify the set of relevant parameters and/or the cluster of correlated parameters.

In some embodiments, the method may further comprise identifying cell populations within the plurality of cells in the control sample and/or in the reference sample based on the parameter values and/or on the feature values. Cell populations may for example be identified based on thresholds for the parameter values and/or for the feature values. In some examples, the method may comprise determining the respective thresholds, e.g. by determining whether the distribution of the respective parameter values or meta-feature values is multimodal and optionally identifying minima and/or maxima in the multi-modal distribution. Additionally or alternatively, cell populations may be identified using a neural network, e.g. by performing a clustering using unsupervised machine learning on the parameter values and/or on the feature values. In one example, one cell population is selected as a subset to be used for further analysis.

In some embodiments, receiving the parameter values for the control sample and/or for the reference sample comprises receiving one or more microscopic images of the respective sample. The one or more microscopic images may in particular comprise images of the respective sample taken at different wavelengths. Individual cells may be identified in the one or more microscopic images and the parameter values for each of the identified individual cells may be extracted from the one or more microscopic images, e.g. using an image analysis software, in particular a cell morphology analysis software such as the software "CellProfiler", see A. E. Carpenter et al., *Genome Biol.,* 7(10): R100 (2006). In some embodiments, a neural network, e.g. a convolutional neural network, may be employed to identify individual cells in the one or more microscopic images and/or to extract parameter values from the one or more microscopic images.

In some embodiments, receiving the one or more microscopic images comprises taking the one or more microscopic images of the control and/or reference samples. The microscopic images may for example be taken by bright-field imaging, dark-field imaging, cross-polarized light imaging, phase-contrast imaging, fluorescence imaging, confocal imaging, and/or superresolution imaging. In some embodiments, this may also comprise staining one or more parts of the cells in the control sample and/or in the reference sample, e.g. the cytoskeleton and/or nuclear DNA. Receiving the one or more microscopy images may further comprise labelling one or more biomolecules or biochemical substances in the cells in the control sample and/or in the reference sample with an imaging marker, e.g. biomolecules involved in a cellular signaling pathway such as one or more transcription factors.

The invention further provides a method of studying an effect of a test substance on a test sample of biological cells using a set of relevant parameters and a set of meta-features determined with a method of determining a set of meta-features according to one of the embodiments described above. The method of studying the effect of the test substance comprises (1) exposing the test sample to the test substance; (2) determining parameter values of the set of relevant parameters for each of a plurality of cells in the test sample; and (3) determining feature values of the set of meta-features for the test sample, wherein each of the feature values is calculated from the parameter values of a cluster of correlated parameters from the set of relevant parameters that is associated with the respective meta-feature.

The test sample may comprise a large number of cells, for example more than 100 cells, in one example between $10^3$ and $10^6$ cells. In some examples, the test sample may comprise two or more subsamples, which may for example be wells on one or more multi-well plates. Preferably, the test sample is similar to the control and reference samples. The test sample may in particular comprise the same types of cells as the control and reference samples, e.g. cells derived from the same cell line as the cells in the control and reference samples.

The test substance may for example be a substance of which a functional, physiological, pathological, and/or morphological effect on cells in the test sample is to be studied. Preferably, the test substance is different from a reference substance that the reference sample was exposed to for determining the meta-features. The test substance may be a single substance or may comprise two or more substances. In some embodiments, subsamples within the test sample may be exposed to different doses of the test substance.

The set of relevant parameters and the set of meta-features may have been determined prior to execution of the method of studying the effect of the test substance. Information pertaining to the set of relevant parameters and to the meta-features may for example be obtained from a data storage, e.g. a list of identifiers for the relevant parameters and the respective definitions of the meta-features. The parameter values of the set of relevant parameters are determined for each of the plurality of cells in the test sample, e.g. as described above, wherein the plurality of cells may comprise all cells in the test sample or a subset thereof. In some examples, the set of relevant parameters may comprise one or more secondary parameters, e.g. as described above. Based on the definitions of the meta-features, the respective feature values are calculated from the parameter values of the relevant parameters of the corresponding cluster. The feature values may be determined for each of the plurality of cells in the test sample or a subset thereof, which may e.g. be selected based on parameter values of the relevant parameters or of additional parameters that are determined in addition to the relevant parameters. The subset may for example be selected as described above and apoptotic cells, non-intact cells, cells not matching a predetermined cell type, and/or cells that are not part of a certain cell population may be excluded from further analysis.

As detailed above, the method of studying an effect of a test substance according to the invention allows for extracting meaningful information from single-cell morphology analyses even for heterogeneous cell populations such as cardiomyocytes by characterizing cells in the test sample in terms of the meta-features determined from clusters of correlated relevant parameters. This may in particular be used for automated drug screening as well as for diagnostic purposes, for example by using a potential inhibitor of a medical condition or a sample of a patient as the test substance as detailed below.

In a preferred embodiment, the method further comprises determining parameter values of the set of relevant parameters for each of a plurality of cells in a control test sample and determining feature values of the set of meta-features from the parameter values of the set of relevant parameters for the control test sample. Preferably, the control test sample is not exposed to the test substance. In some examples, the control test sample may have been exposed to a different substance instead or may not have been exposed to any substance other than substances that the test sample has also been exposed to in addition to the test substance, e.g. a cell culture medium. The method may further comprise comparing feature values of meta-features for the test sample and feature values of meta-features for the control test sample to assess the effect of the test substance, e.g. for at least one meta-feature, in some examples for all of the meta-features. Preferably, this comprises determining a significance measure characterizing a statistical significance of a difference or equivalence between the respective feature values in the control sample and in the reference sample, e.g. as described above. In some examples, this may in particular comprise modelling a dose dependency of an effect of the test substance on the respective meta-feature using a statistical model, e.g. a mixed error-component model.

In a preferred embodiment, the reference sample for determining the set of meta-features was exposed to a stimulus substance, the stimulus substance being a mediator involved in one or more medical conditions, e.g. as described above. The stimulus substance may in particular be a mediator involved in one or more cardiovascular conditions. In one example, the stimulus substance comprises a hypertrophy inducing substance, in particular at least one of phenylephrine, adrenaline, noradrenaline, isoproterenol, insulin, endothelin, and angiotensin. By using meta-features associated with a certain medical condition and in particular with a certain mediator, the effect of the test substance with regard to the medical condition and pathways associated with the mediator may be assessed.

In some embodiments, a plurality of sets of relevant parameters and a plurality of sets of meta-features may be used and the method may comprise determining the respective parameter and feature values for the test sample and/or for the test control sample. Preferably, each of the sets of relevant parameters/meta-features was determined using a different stimulus substance, e.g. a plurality of mediators involved in the same medical condition, in particular the same cardiovascular condition. In one example, a plurality of sets of relevant parameters/meta-features is used, wherein each of the sets was determining using a stimulus substance comprising a different hypertrophy inducing substance, in particular a different one of phenylephrine, adrenaline, noradrenaline, isoproterenol, insulin, endothelin, and angiotensin.

In a preferred embodiment, the test substance comprises a candidate substance to be tested as a potential inhibitor of the medical condition and/or a substance associated with a pathway related to the medical condition, e.g. a specific protein. Accordingly, the method according to the invention may be used to assess the effect of the candidate substance on the meta-features associated with the particular medical condition, which may allow for efficiently identifying promising substances for the development of novel drugs. In some examples, the test substance may additionally comprise other substances, for example a stimulus substance being a mediator involved in the medical condition. In one example, the stimulus substance may be the same as the reference substance used to determine the set of relevant parameters and the set of meta-features.

In another preferred embodiment, the test substance comprises a sample of a patient. The sample may in particular be a blood sample of the patient, preferably blood serum or blood plasma of the patient. The method according to the invention may thus be used for diagnostic purposes similar to the method of EP 2 954 322 A1. This may for example allow for determining whether the blood plasma of a patient has an effect on meta-features associated with a certain medical condition or mediator therefor. In some examples, the test substance may comprise another substance in addition to the sample of the patient, e.g. a mediator for a medical condition such as a hypertrophy inducing substance.

The method may in particular also comprise diagnosing a medical condition, assessing a risk of developing the medical condition and/or assessing a progress of a therapeutic treatment against the medical condition based on the feature values of the set of meta-features for the test sample. The medical condition may for example be a cardiovascular condition, in particular hypertrophic cardiomyopathy, amyloidosis and/or aortic stenosis. Other examples of medical conditions include medical conditions associated with heart failure such as arrhythmia, coronary artery disease, hypertension, metabolic diseases, and autoimmune diseases. The method may e.g. comprise quantifying a difference of meta-features for the test sample and for the test control sample and a significance thereof, e.g. for one or all of the meta-features. This may further comprise comparing the difference to one or more pre-defined thresholds or to the difference of a previous assessment, e.g. at an earlier stage of the treatment of the patient. The medical condition may for example be diagnosed or the risk of developing the medical condition may for example be considered as high if the difference of the meta-feature or for a certain fraction of meta-features exceeds the pre-defined threshold or if the difference of the meta-feature or for a certain fraction of meta-features is below the pre-defined threshold, e.g. if the respective meta-features are equivalent. In one example, diagnosing the medical condition may also comprise determining a probability for one or more subtypes of the medical condition and/or diagnosing a subtype of the medical condition. In some examples, the method may also comprise assessing a prognosis for a clinical endpoint such as survival or cardiac decompensation. For diagnosing the medical condition, assessing the risk of developing the medical condition and/or assessing the progress of the therapeutic treatment, other data may be taken into account in addition to the feature values of the set of meta-features, in particular clinical data such as blood values or cardiologic measurements.

In some embodiments, the parameter values of the set of relevant parameters for the test sample and/or for the control test sample are determined from one or more microscopic images of the cells in the respective sample, e.g. as detailed above.

In some embodiments, the method further comprises performing a single-cell phenotyping by determining feature values of the set of meta-features and/or parameter values of the set of relevant parameters for at least one of the plurality of cells in the test sample and/or for at least one of the plurality of cells in the test control sample. The single-cell phenotyping may comprise transforming the feature and/or parameter values, e.g. using a dimensionality reduction method such as T-distributed stochastic neighbor embedding (t-SNE). In one example, the feature and/or parameter values are mapped onto a two- or three-dimensional space.

In some embodiments, the method further comprises performing a population-level phenotyping by determining average feature values of the set of meta-features and/or average parameter values of the set of relevant parameters averaged over a set of cells from the plurality of cells in the test sample and/or in the control test sample. In some examples, the method may comprise determining the set of cells for the population-level phenotyping, e.g. based on thresholds for one or more meta-features and/or relevant parameters. In one example, the method may also comprise determining the threshold, for example by identifying multimodal distributions as described above.

In a preferred embodiment, the method also comprises determining the set of relevant parameters and the set of meta-features using the method of determining a set of meta-features according to one of the embodiments described above.

The invention further provides a computer program product comprising a set of machine-readable instructions executable by a processing device. The instructions cause the processing device to execute a method of determining a set of meta-features according to any one of the embodiments described above and/or a method of studying an effect of a test substance on a test sample according to any one of the embodiments described above.

In some embodiments, the computer program product comprises a set of instructions to determine a set of meta-features for comparing samples of biological cells using the corresponding method according to any one of the embodiments described above. The set of instructions comprises instructions to (1) receive parameter values of a set of cell parameters for each of a plurality of cells in a control sample and for each of a plurality of cells in a reference sample; (2) identify a set of relevant parameters from the set of cell parameters by comparing the parameter values from the control sample and the parameter values from the reference sample for at least one of the cell parameters; (3) identify clusters of correlated parameters within the set of relevant parameters based on correlations between the parameter values of the relevant parameters; and (4) define a meta-feature for at least one of the clusters as a mathematical function of the parameters of the respective cluster.

Additionally or alternatively, the computer program product comprises a set of instructions to study an effect of a test substance on a test sample of biological cells using the corresponding method according to any one of the embodiments described above. For this, a set of relevant parameters and a set of meta-features are used that were determined with a corresponding method according to any one of the embodiments described above, e.g. by execution of the respective instructions of the computer program product by the processing device. The set of instructions comprise instructions to (1) expose the test sample to the test substance; (2) determine parameter values of the set of relevant parameters for each of a plurality of cells in the test sample; and (3) determine feature values of the set of meta-features for the test sample, wherein each of the feature values is calculated from the parameter values of a cluster of correlated parameters from the set of relevant parameters that is associated with the respective meta-feature.

In addition, the computer program product may comprise further instructions for executing one or both of the methods in accordance with any one of the embodiments described above. The computer program product may for example comprise additional instructions for comparing the parameter values of the control and reference samples and identifying the relevant parameters, for identifying the clusters of correlated parameters, for determining secondary parameters, and/or for extracting the parameter values from microscopic images. In some examples, the computer program product may also comprise additional instructions for comparing features values for the test sample with a control test sample, for diagnosing a medical condition, assessing a risk of developing the medical condition, and/or assessing a progress of a therapeutic treatment against the medical condition, and/or for performing a single-cell and/or population-level phenotyping.

The invention further relates to a system comprising a processing device and a data storage coupled to the processing device. The data storage stores a set of machine-readable instructions that, when executed by the processing device, cause the processing device to (1) receive at least one microscopic image of a test sample of biological cells and at least one microscopic image of a control test sample of biological cells; (2) determine parameter values of a set of relevant parameters for each of a plurality of cells in the test sample and for each of a plurality of cells in the control test sample from the at least one microscopic image of the respective sample; (3) determine feature values of a set of meta-features from the parameter values of the set of relevant parameters for the test sample; and (4) determine feature values for the set of meta-feature from the parameter values of the set of relevant parameters for the control test sample. The set of relevant parameters and the set of meta-features used for this were determined using the method of determining a set of meta-features according to any one of the embodiments described above. Information pertaining to the set of relevant parameters and the set of meta-features may for example be stored in the data storage.

In some embodiments, the data storage may store additional instructions, e.g. some or all of the instructions of the computer program product described above. The system may also comprise additional components. In some embodiments, the system may comprise one or more samples, e.g. at least one test sample, wherein the test sample is to be exposed to a test substance, at least one control test sample, at least one reference sample, and/or at least one control sample. The system may also comprise one or more reference substances. In some examples, the system may further be configured to control a microscope, e.g. a high-throughput microscope, and/or a sample preparation subsystem, e.g. a pipetting robot configured to prepare the samples in wells on one or more multi-well plates.

LIST OF FIGURES

Figure 2:
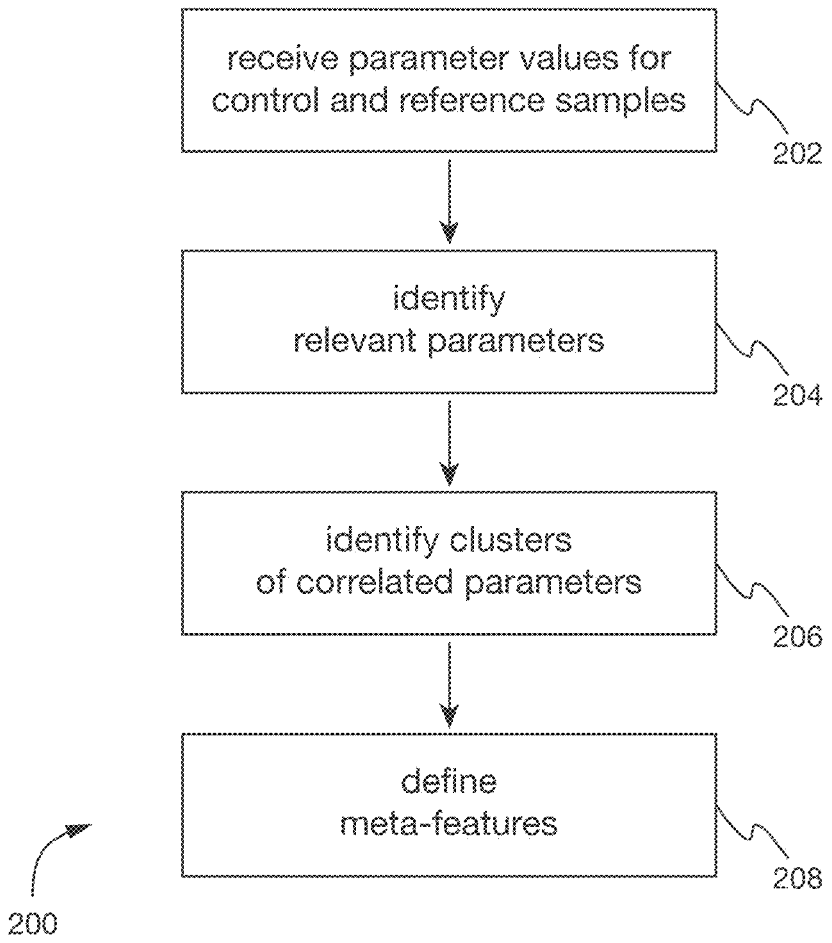
Figure 3:
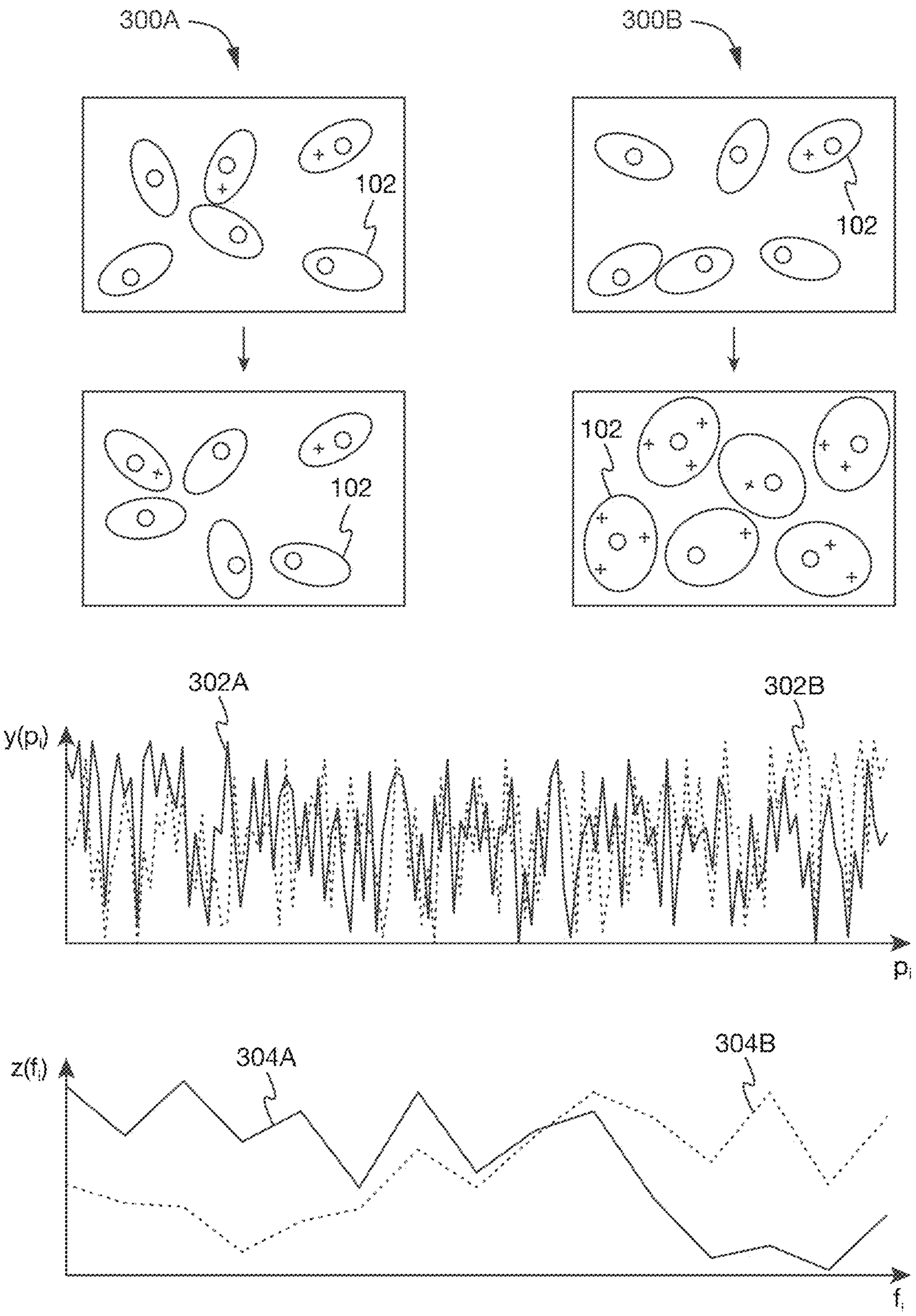
Figure 4:
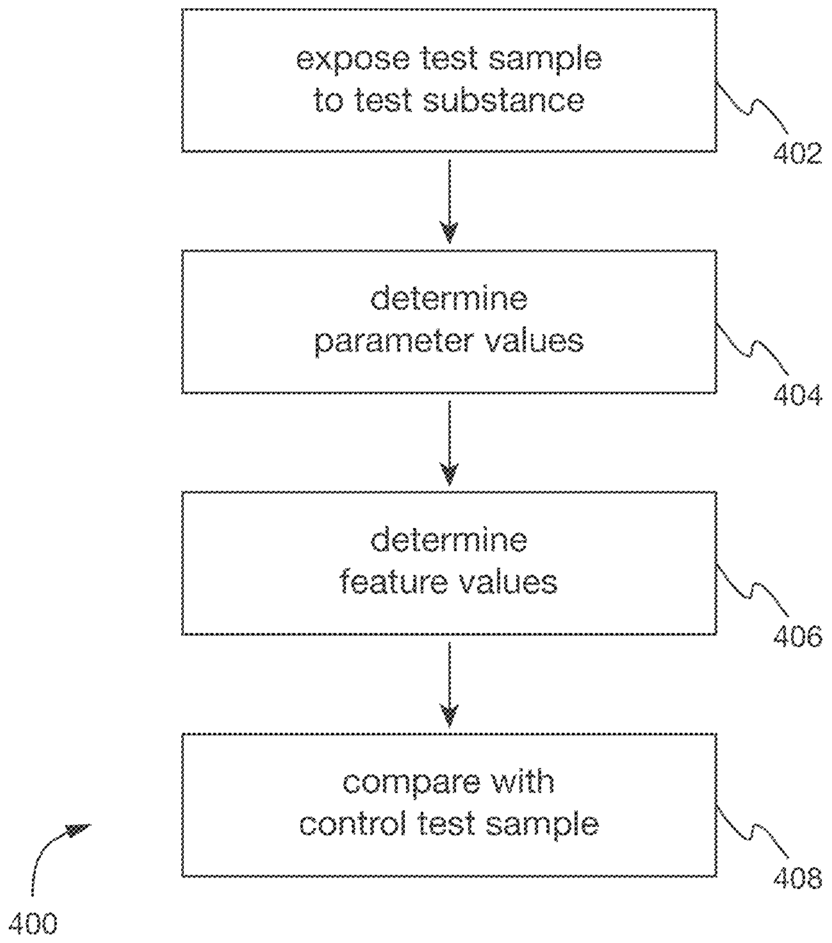
Figure 5:
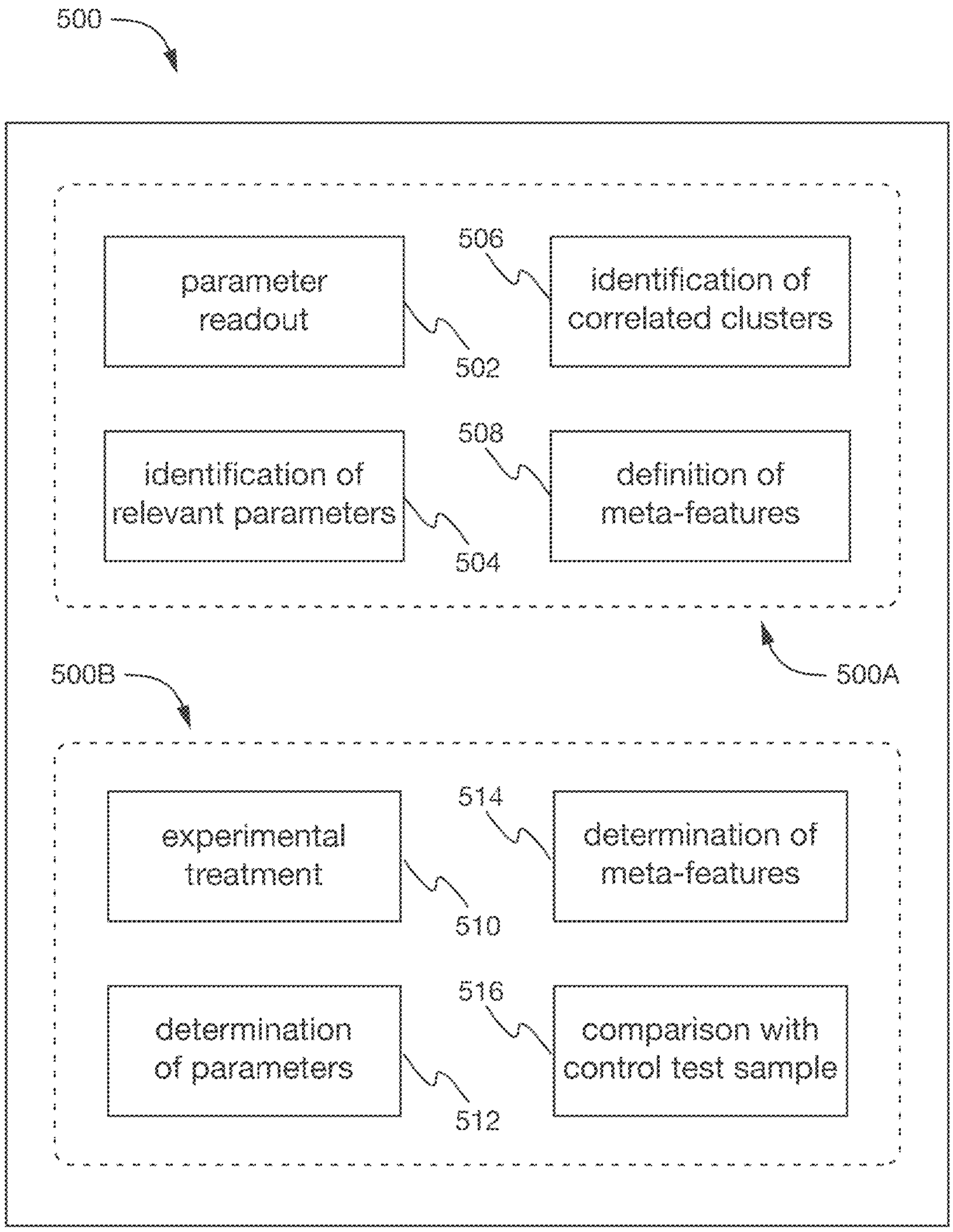
Figure 6:
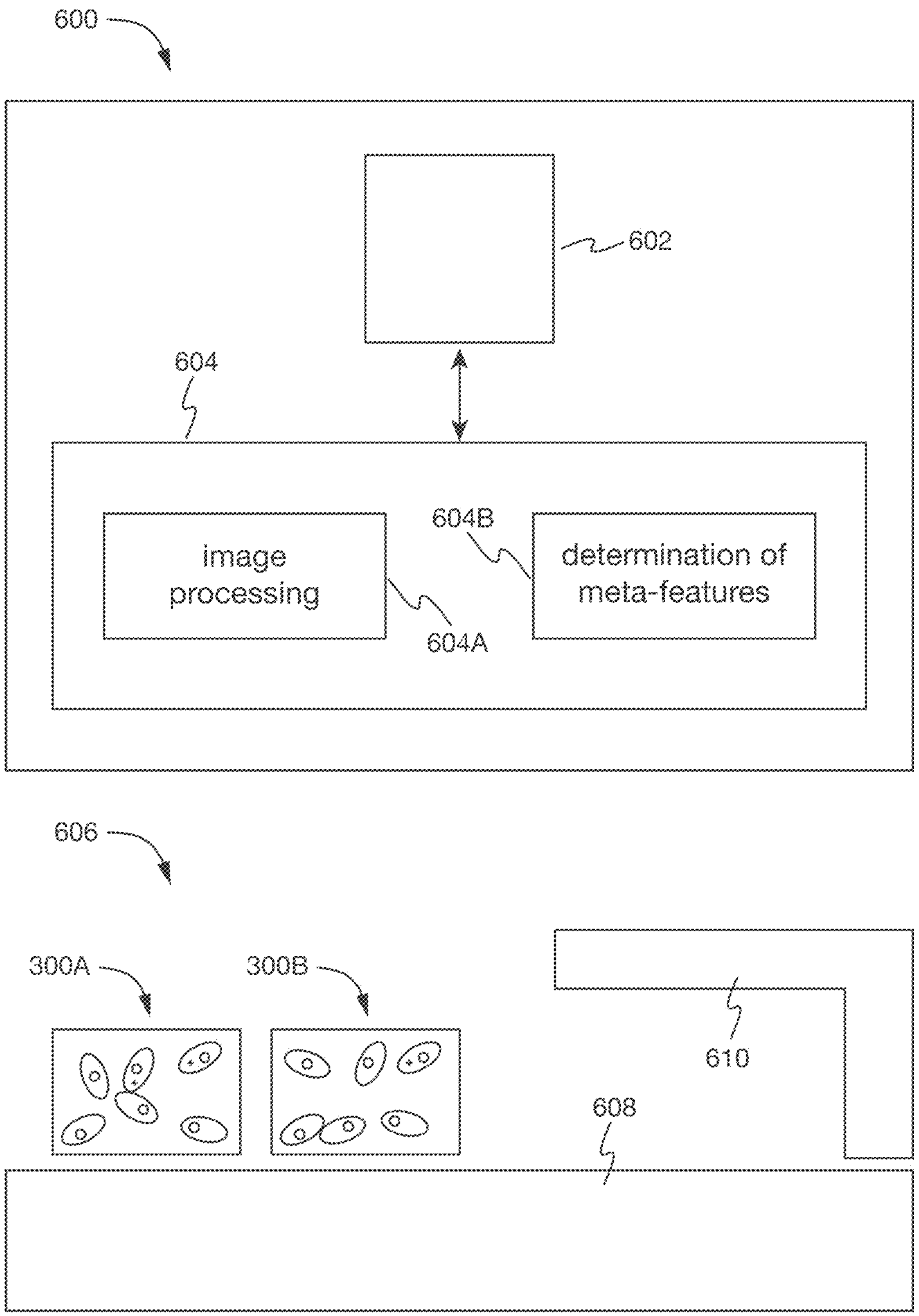
Figure 7:
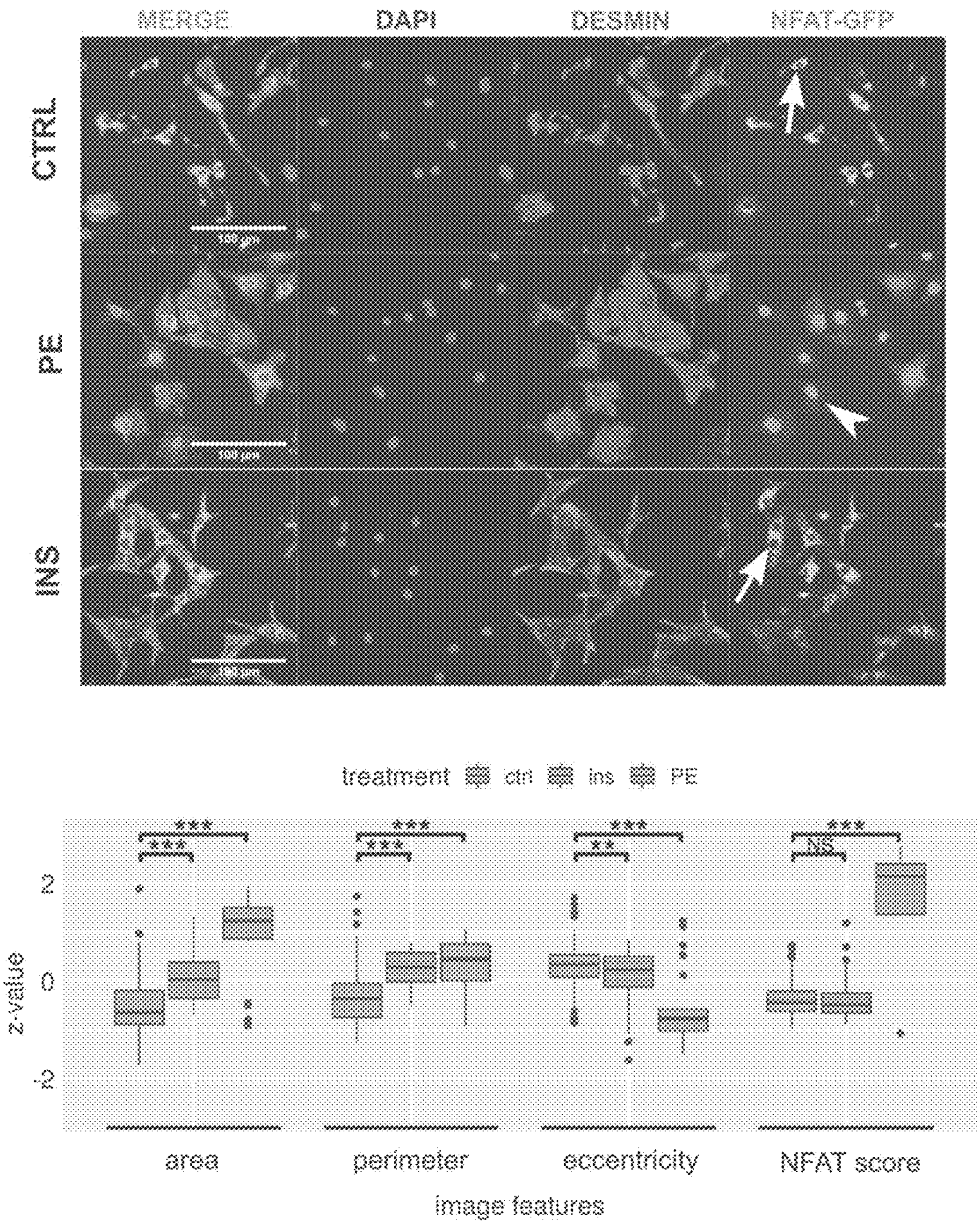
Figure 8:
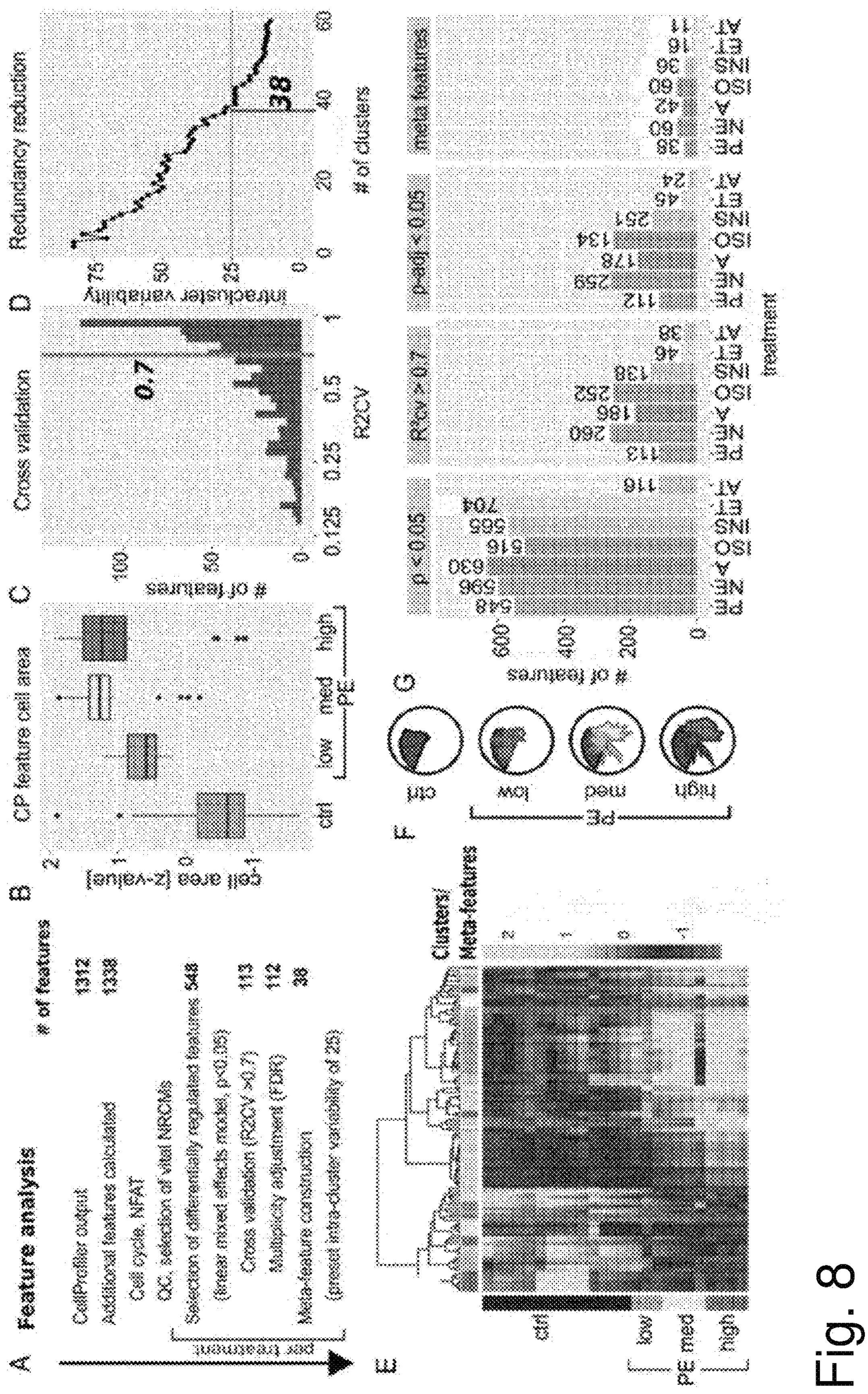
Figure 9:
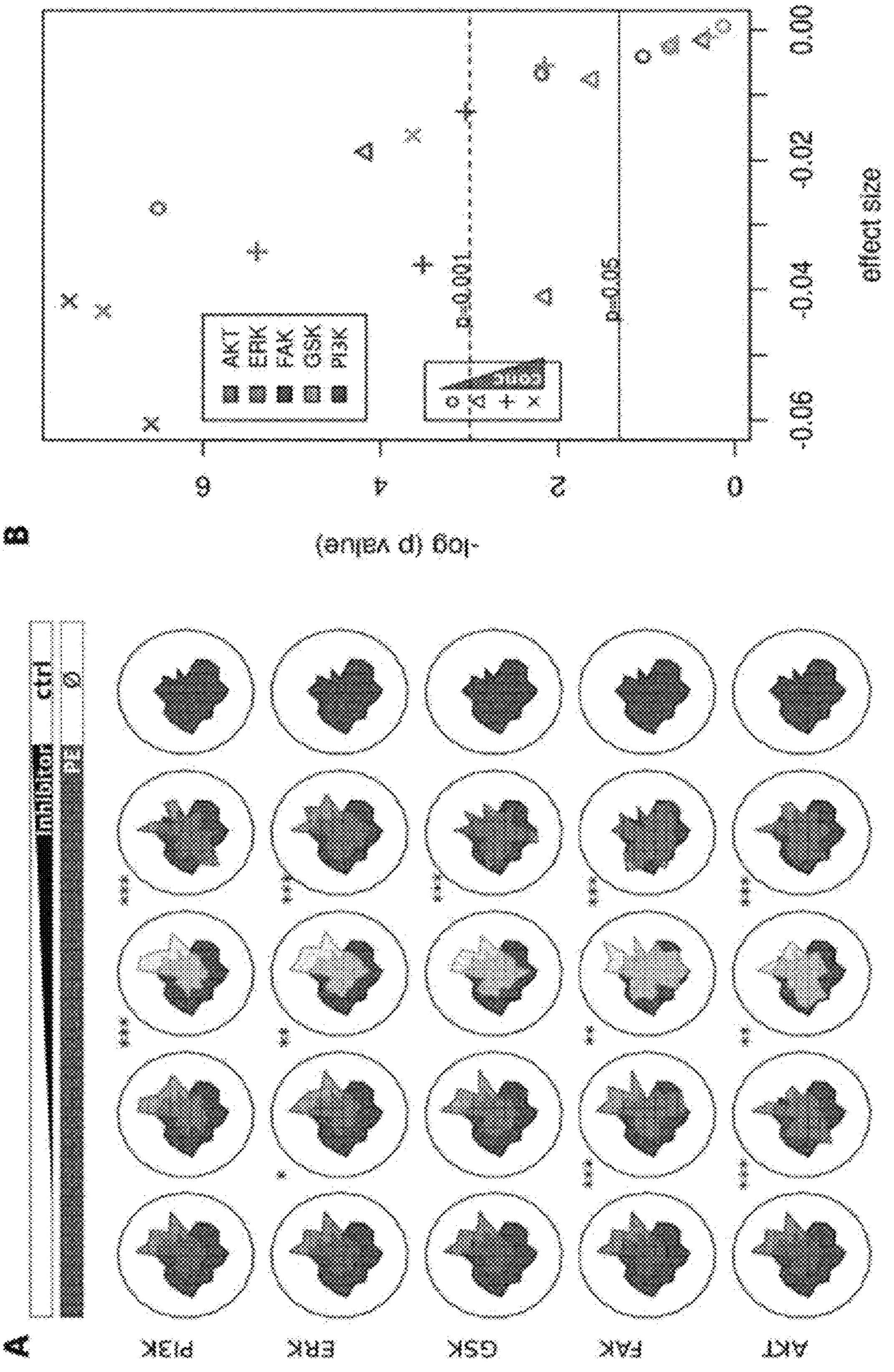
Figure 10:
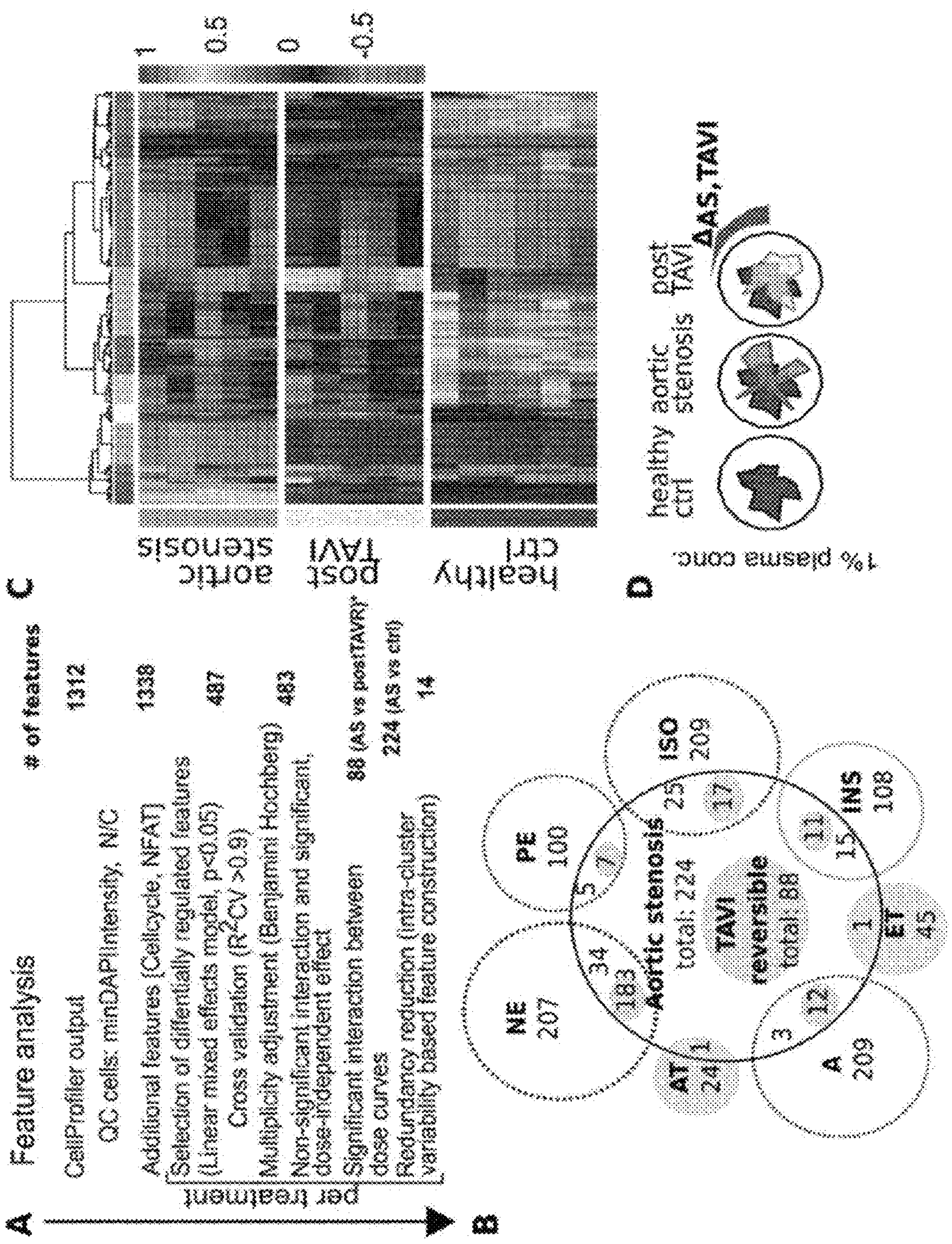
Figure 11:
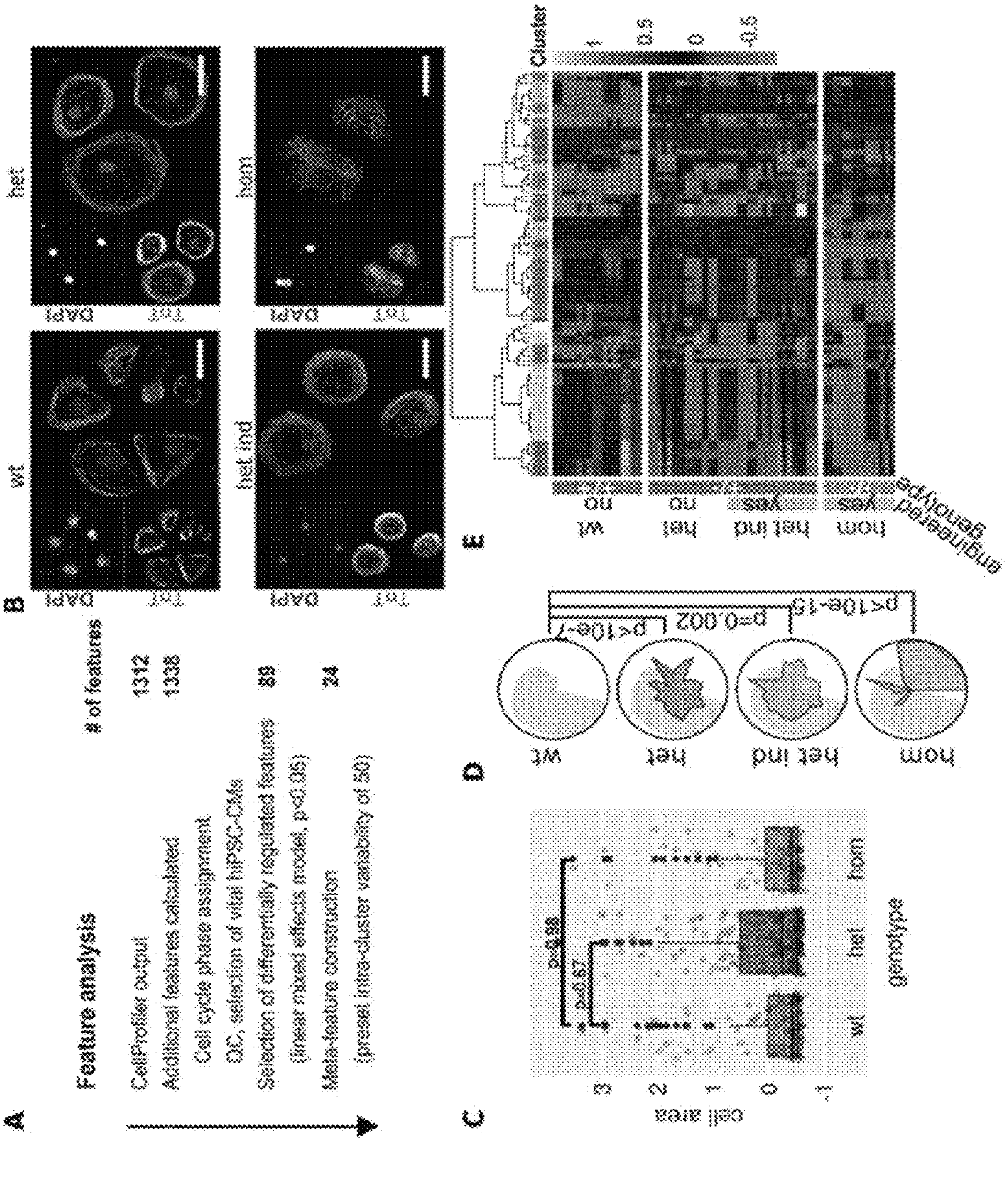
Figure 12A:
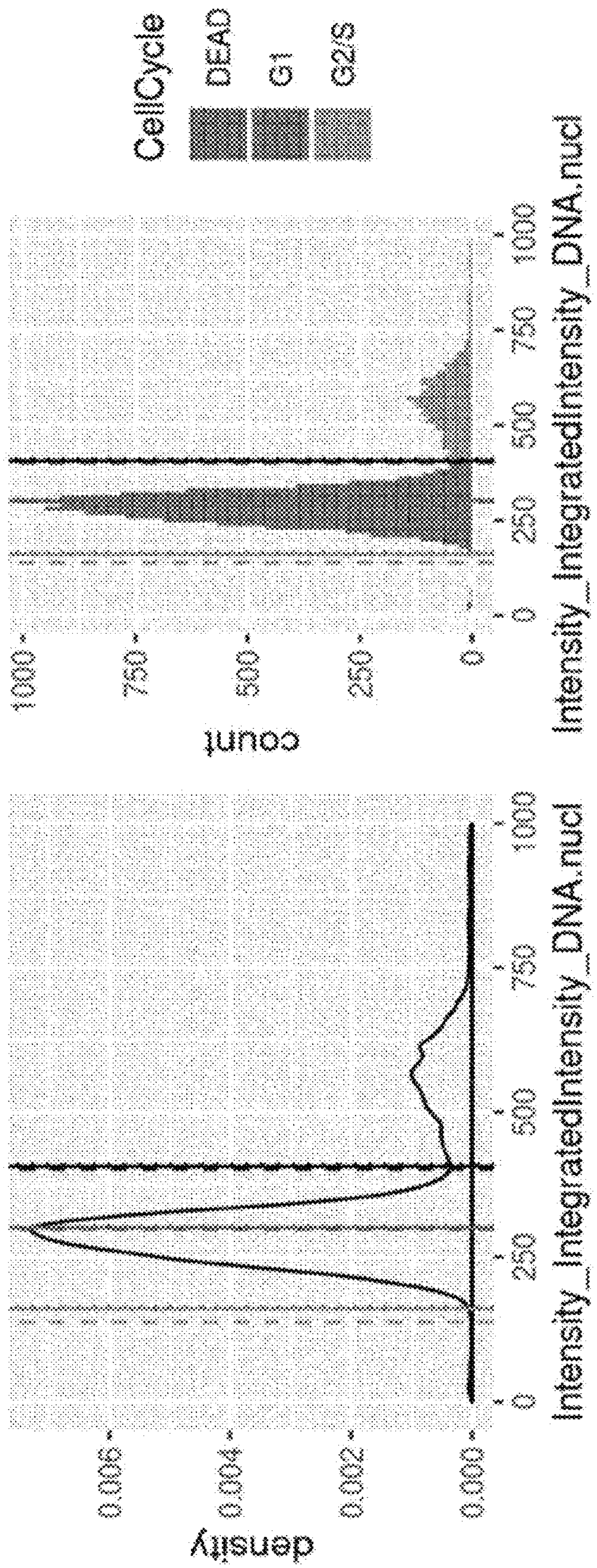
Figure 12B:
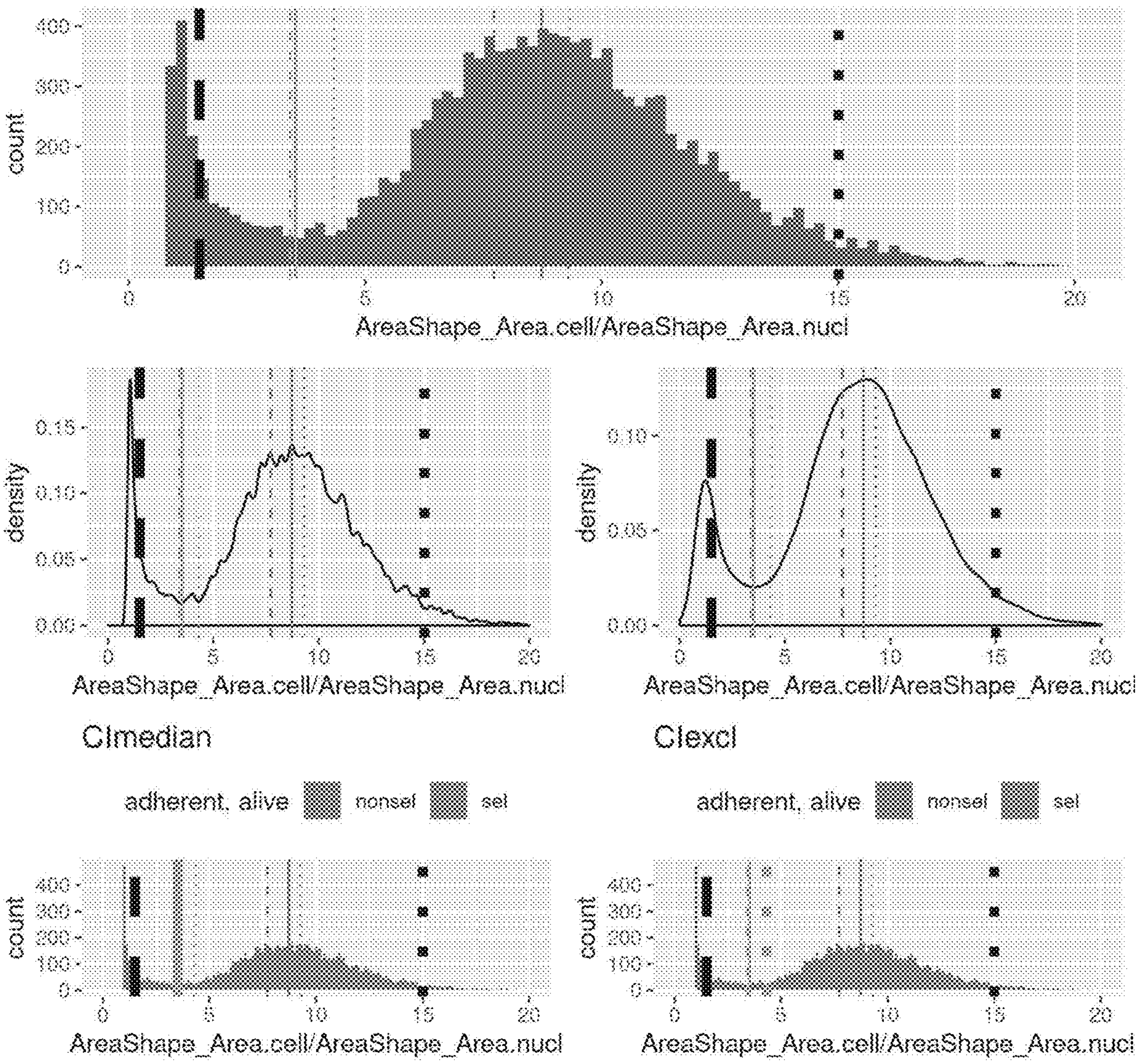
Figure 13:
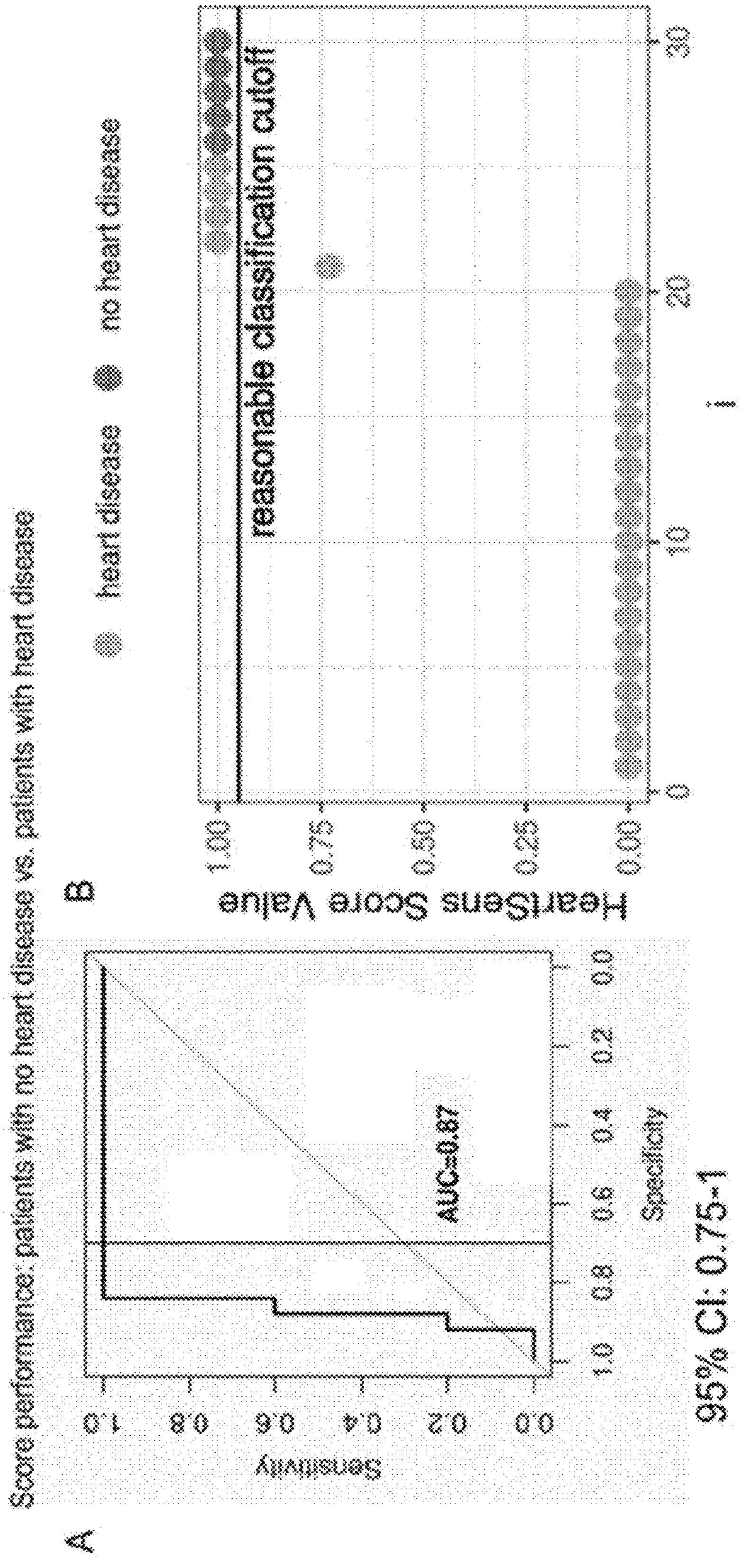

In the following, a detailed description of the invention and exemplary embodiments thereof is given with reference to the figures. The figures show schematic illustrations of FIG. 1: a sequence of steps of a method of determining a set of meta-features according to an exemplary embodiment of the invention;

FIG. 2: a flow diagram of a method of determining a set of meta-features in accordance with an exemplary embodiment of the invention;

FIG. 3: a sequence of steps of a method of studying an effect of a test substance on a test sample according to an exemplary embodiment of the invention;

FIG. 4: a flow diagram of a method of studying an effect of a test substance on a test sample in accordance with an exemplary embodiment of the invention;

FIG. 5: a computer program product according to an exemplary embodiment of the invention;

FIG. 6: a system in accordance with an exemplary embodiment of the invention;

FIG. 7: microscopic images of control and reference samples comprising cardiomyocytes and a determination of relevant parameters according to an exemplary embodiment of the invention;

FIG. 8: a determination of a set of meta-features using phenylephrine as a stimulus substance for samples of cardiomyocytes in accordance with an exemplary embodiment of the invention;

FIG. 9: a study of the effect of a plurality of hypertrophy inhibiting substances on test samples of cardiomyocytes using a method according to an exemplary embodiment of the invention;

FIG. 10: a study of the effect of blood plasma from patients with aortic stenosis on test samples of cardiomyocytes using a method in accordance with an exemplary embodiment of the invention;

FIG. 11: a study of human induced pluripotent stem cell derived cardiomyocytes (hiPSC-CMs) using a method according to an exemplary embodiment of the invention;

FIG. 12*a*: a determination of a cell cycle state using a method in accordance with an exemplary embodiment of the invention;

FIG. 12*b*: a selection of intact cells using a method according to an exemplary embodiment of the invention; and FIGS. 13 to 17 show experimental results.

Figure 18:
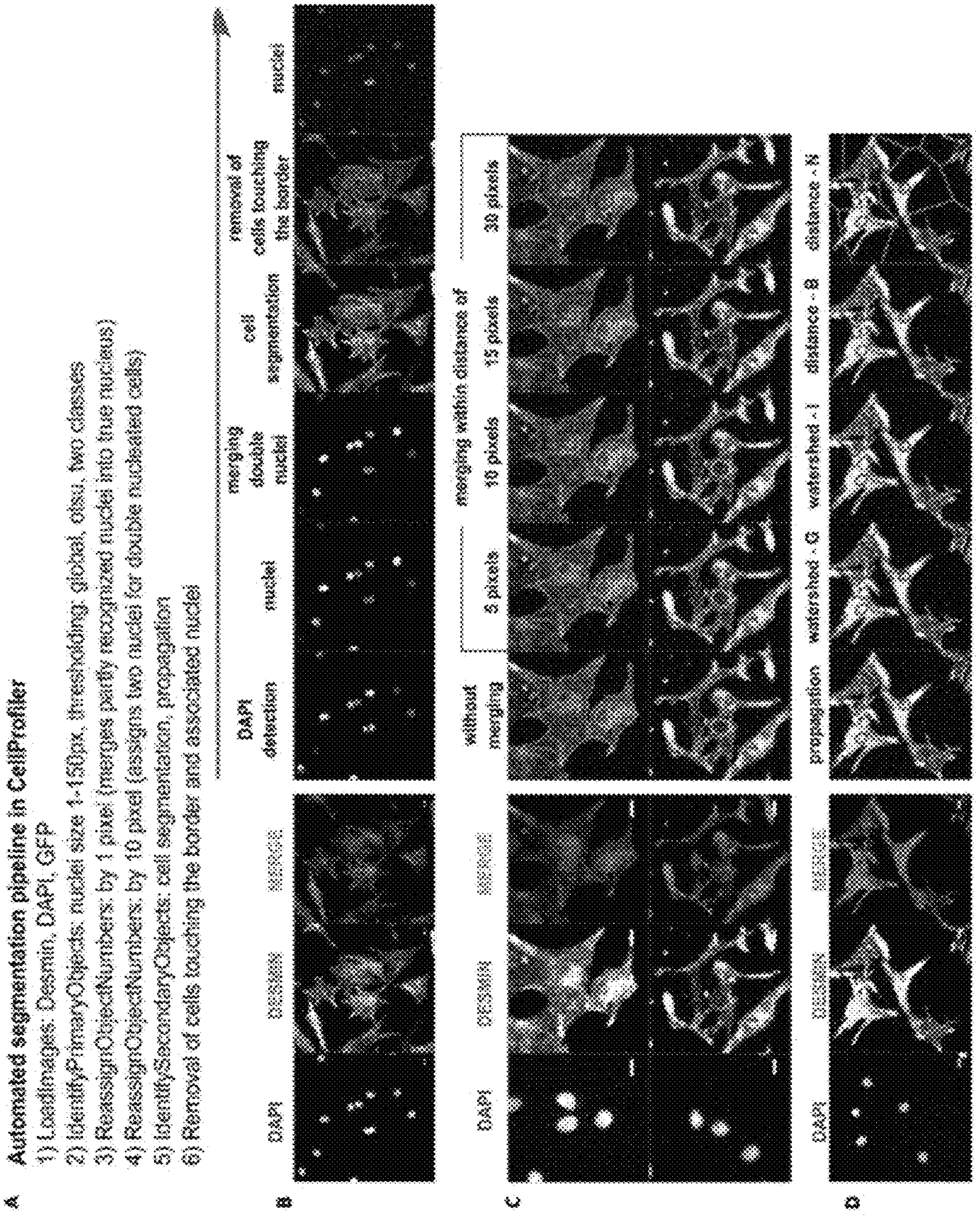
Figure 19:
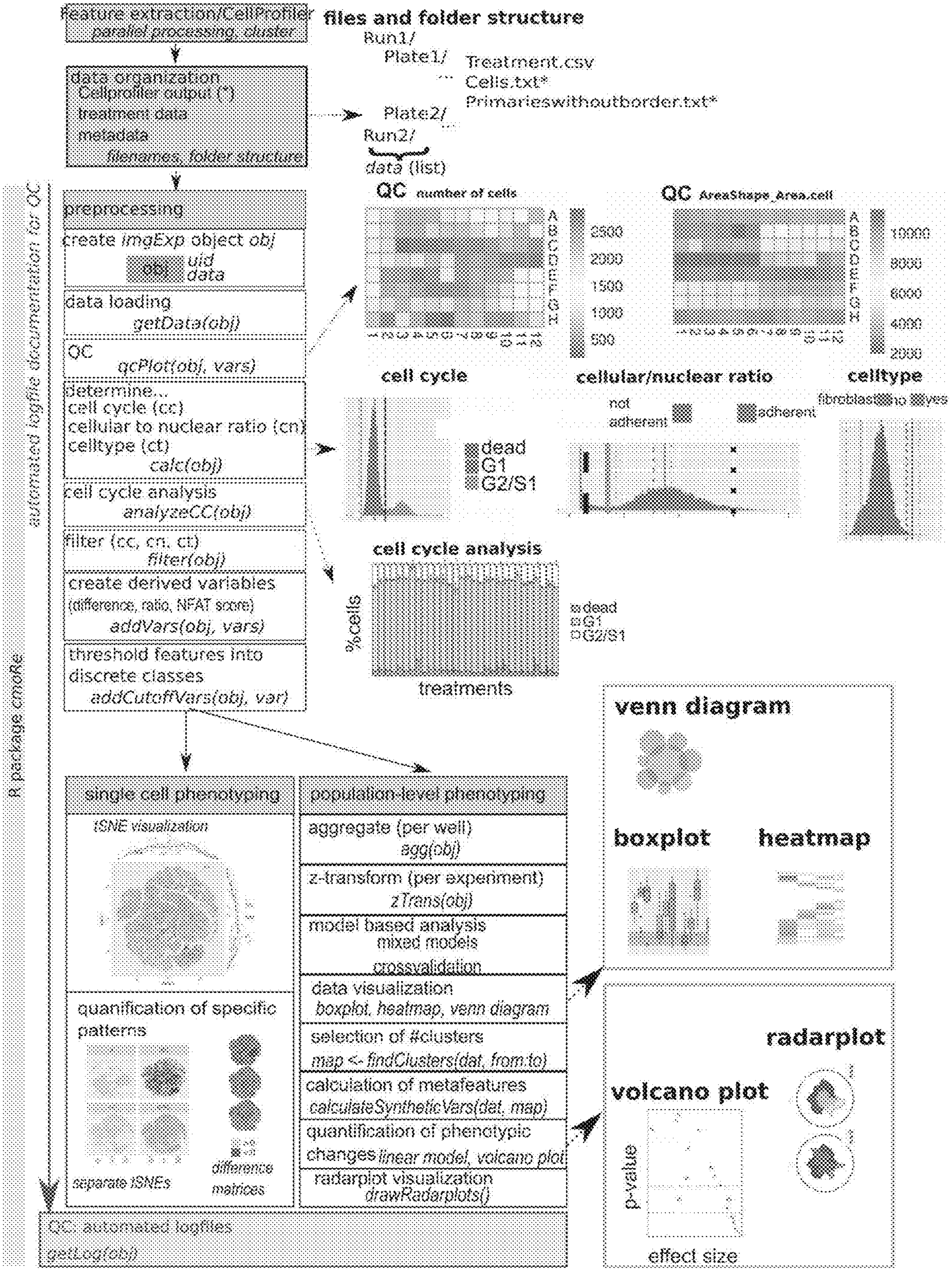

FIG. 18: CellProfiler pipeline functionality, related to FIG. 7 and STAR methods. A: Overview of the CellProfiler analysis steps performed with most important settings. B: CellProfiler step 2 is illustrated, where the detected DAPI intensity is converted into single nuclei by merging very near DAPI signal into a nucleus (1 pixel). C shows the detection of double nucleated cells by distance of two nuclei. This distance of 10 pixels was tested empirically to be optimal to identify true multi-nucleated cardiomyocytes, while minimizing misidentification of nearby single nucleated cells. For cardiomyocytes the propagation method to segment cell bodies works best as shown in D. Data information: Images were cropped for better visualization FIG. 19: Overview of the R package cmoRe and the proposed workflow, related to STAR methods. For a working example and additional information, we refer to the package vignette and package documentation. The analysis workflow can be divided in three main parts: 1) Processing of images using CellProfiler, 2) Preprocessing using the R package cmoRe for QC, cell type/state identification, data filtering, transformation, calculation of secondary derived features and 3) downstream analysis on single cell or population-level (meta feature construction, model based evaluation, visualization). Representative images of QC plots (e.g. numbers of cells in 96 well plates), DNA quantity distributions used for cell cycle determination and cellular to nuclear size ratios to filter for dead cells as shown. CellProfiler output files and a treatment assignment file need to be provided as input. In the preprocessing steps quality control for cell number distribution on the plate and filtering for vital cardiomyocytes are included. One of these filter steps is the quantification of cell cycle phases, based on which very low intense objects are filtered. Further, the calculated cell cycle phase constitutes an additional secondary feature taken up into the analysis. Via thresholding additional secondary features are calculated, e.g. NFAT Score.

Figure 20:
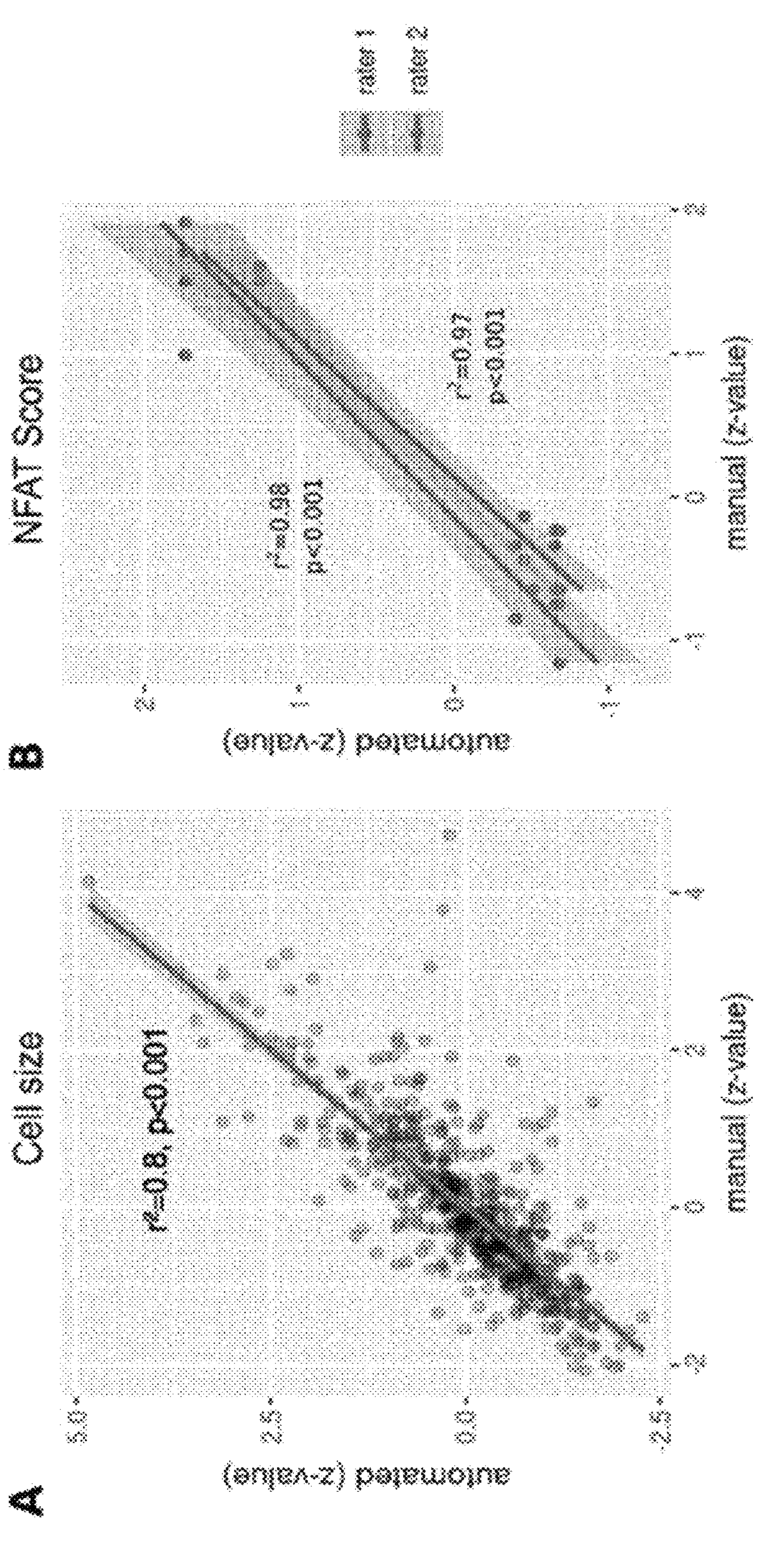

FIG. 20: Validity assessment of automated measurements, related to STAR methods. A: Correlation between manual an automatically determined cell sizes (z-transformation, spearman correlation, n=612 cells, p-value: likelihood ratio test between linear models, dependent variable: manually dependent measurements). B: Numbers of nuclear GFP positive cells as determined automatically (Fibroblast filter) and by two raters. Metrics are calculated as in A.

Figure 21:
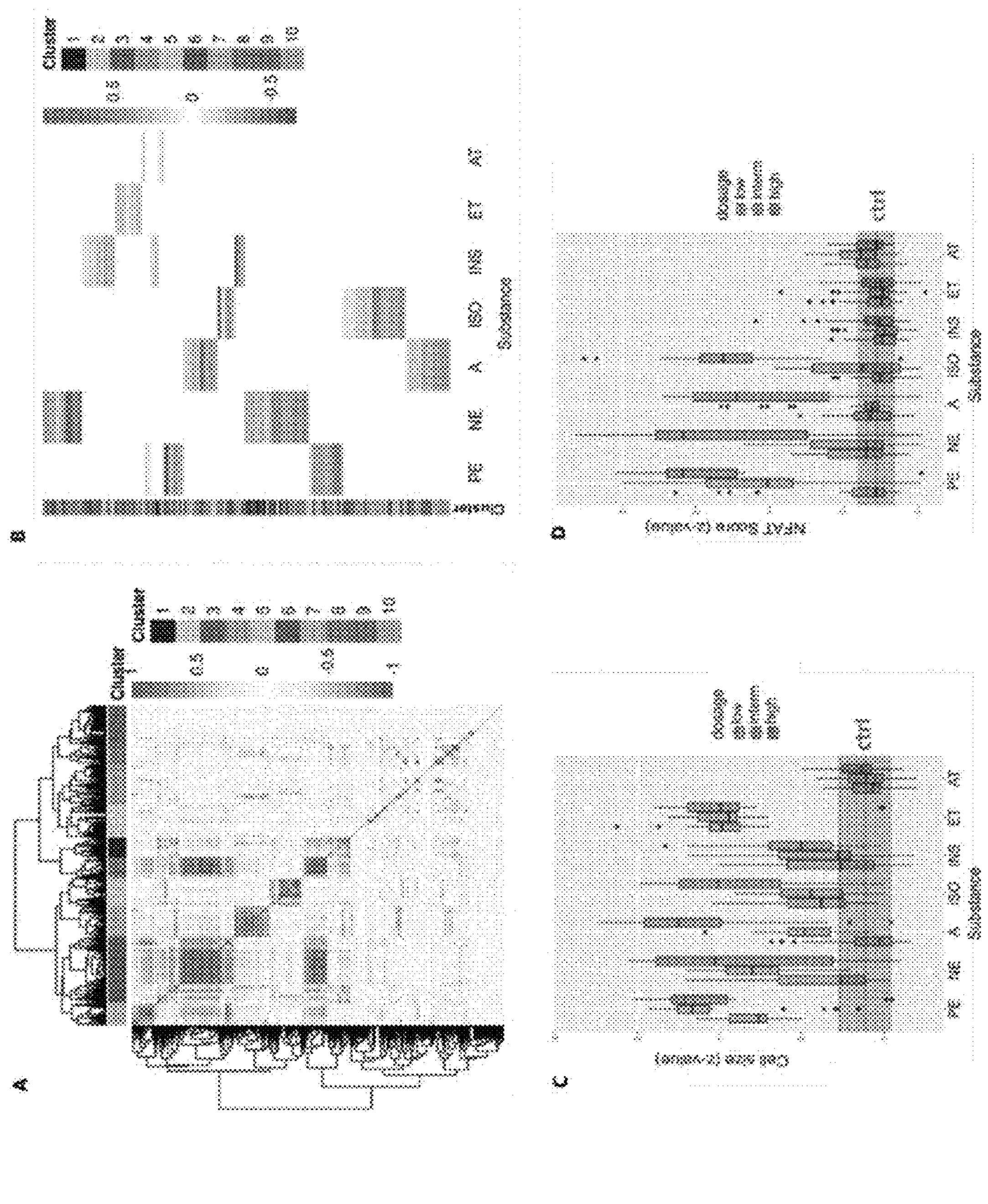

FIG. 21: Correlation of features in control cardiomyocytes, substance specific feature changes and differences in cell sizes and nuclear NFAT positive cell fractions, related to FIG. 8. A. Correlation between single variables in untreated cardiomyocytes (correlation matrix, ward.D2 distance, Pearson correlation). B Heatmap of treatment-unique features. Red for increase, blue for decrease compared to control. C: Cell size for all treatments and concentrations (z-values). D: Nuclear GFP (NFAT) positive fraction of cells (z-score) for all treatments and concentrations. For control condition the median and median absolute deviation is depicted in darker grey (C and D).

Figure 22:
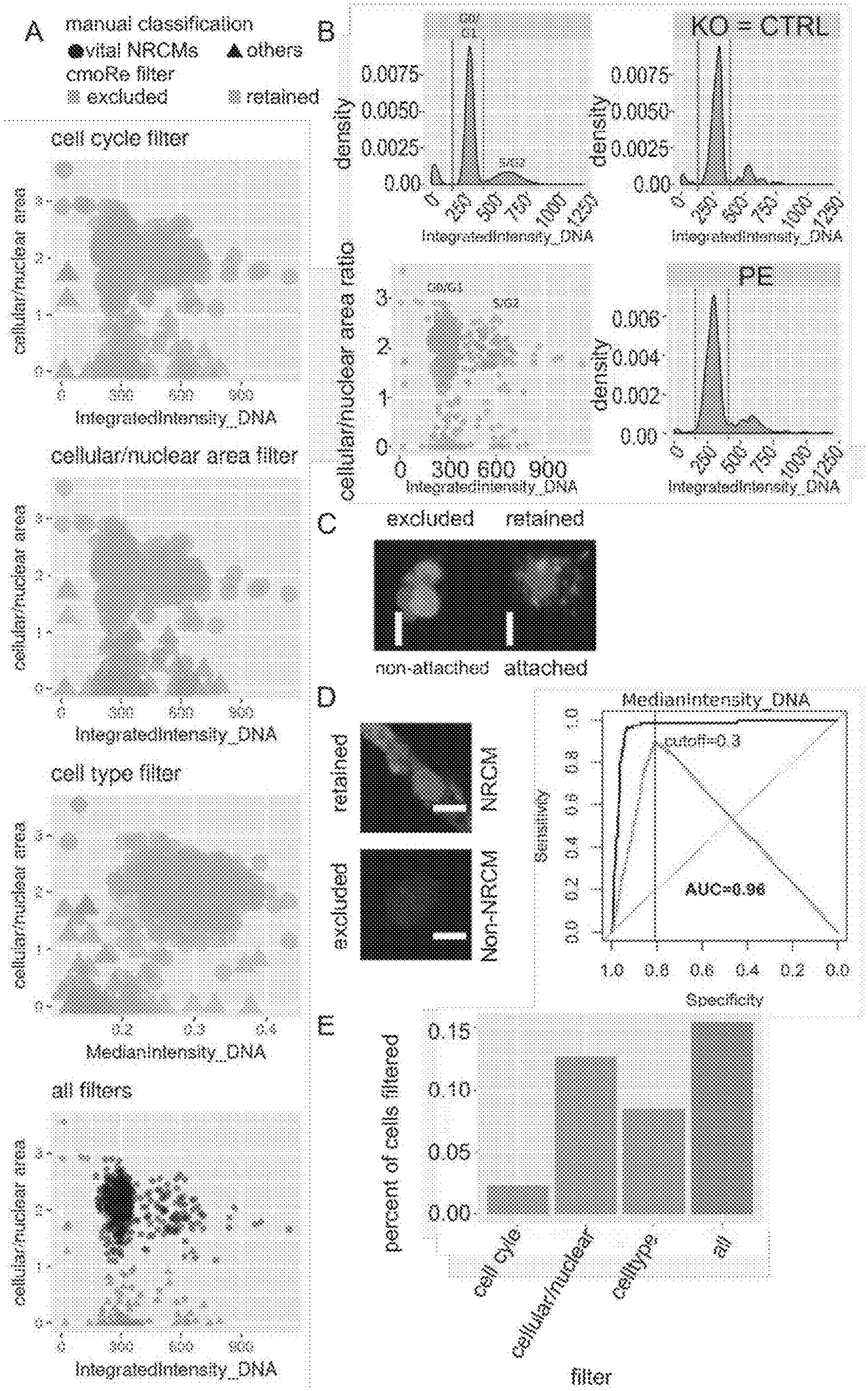

FIG. 22: Filters implemented in the C-MORE workflow, related to FIG. 8 and STAR methods. Scatter plots of single variables used for automatic thresholding to filter single cells. B: Schematic and representative measures of nuclear DNA signal used for automatic cell cycle assignment. C: exemplary retained and filtered objects by cellular/nuclear area filter to exclude debris and non-attached cells. D: Left: Exemplary retained and filtered objects by cell type filter to exclude non-cardiomyocyte cells. Right: ROC analysis of median DNA intensity allows identification of non-NRCM with high sensitivity and specificity. In black the ROC curve is shown, the red line shows the Youden index. E: Fraction of cells excluded for each single filter step and fraction of overall excluded cells.

Figure 23A:
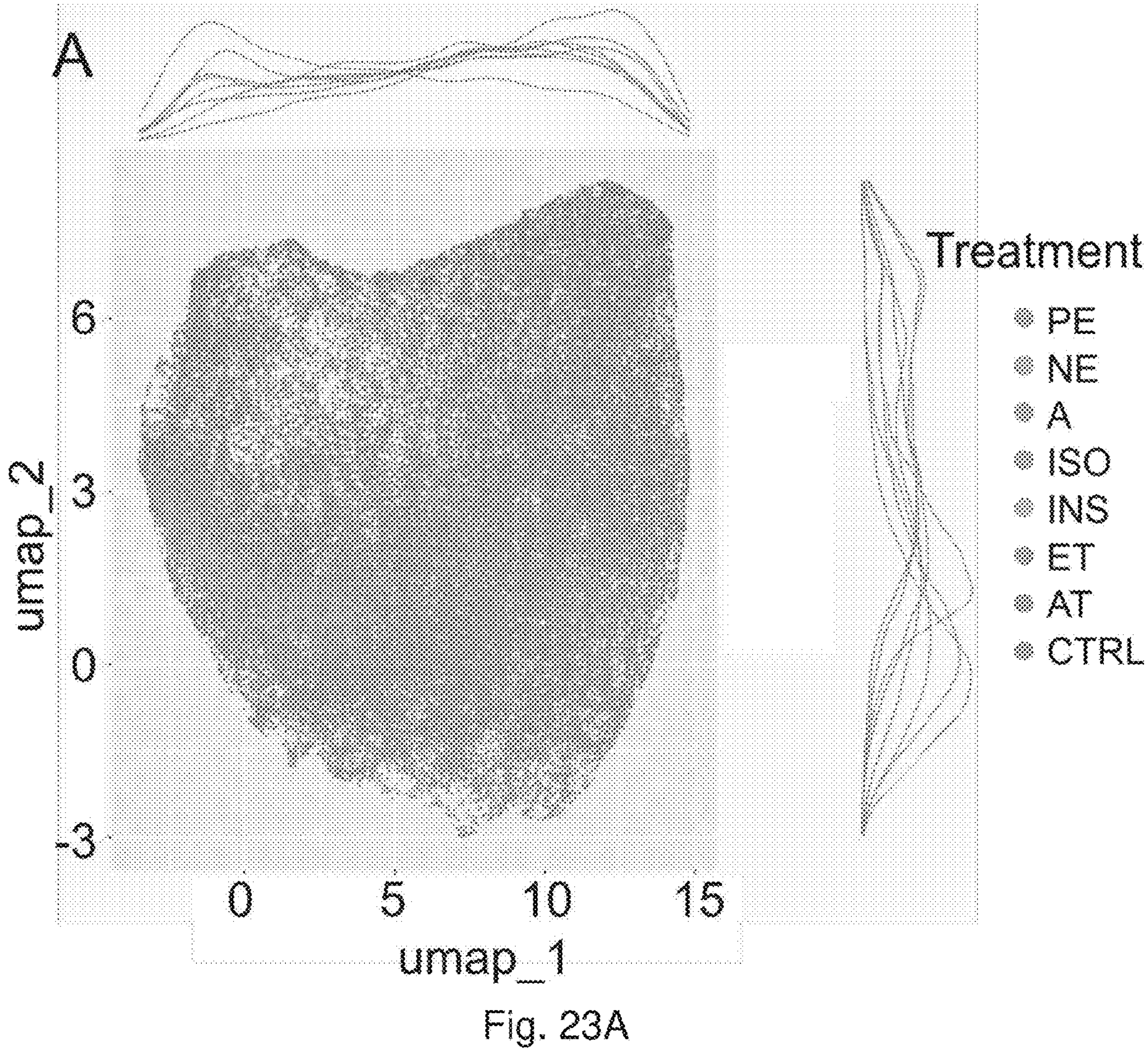

FIG. 23*a*: UMAP representation of single cell data, related to FIG. 8 and STAR methods. A: UMAP including all stimuli, with marginal distributions.

Figure 23B:
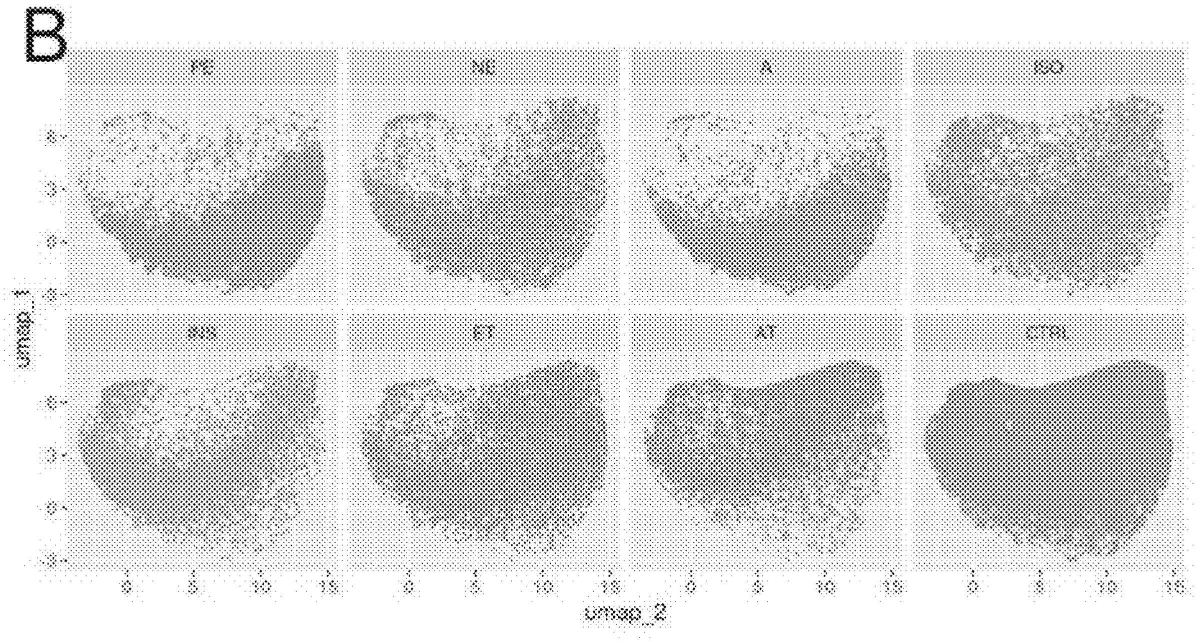
Figure 23C:
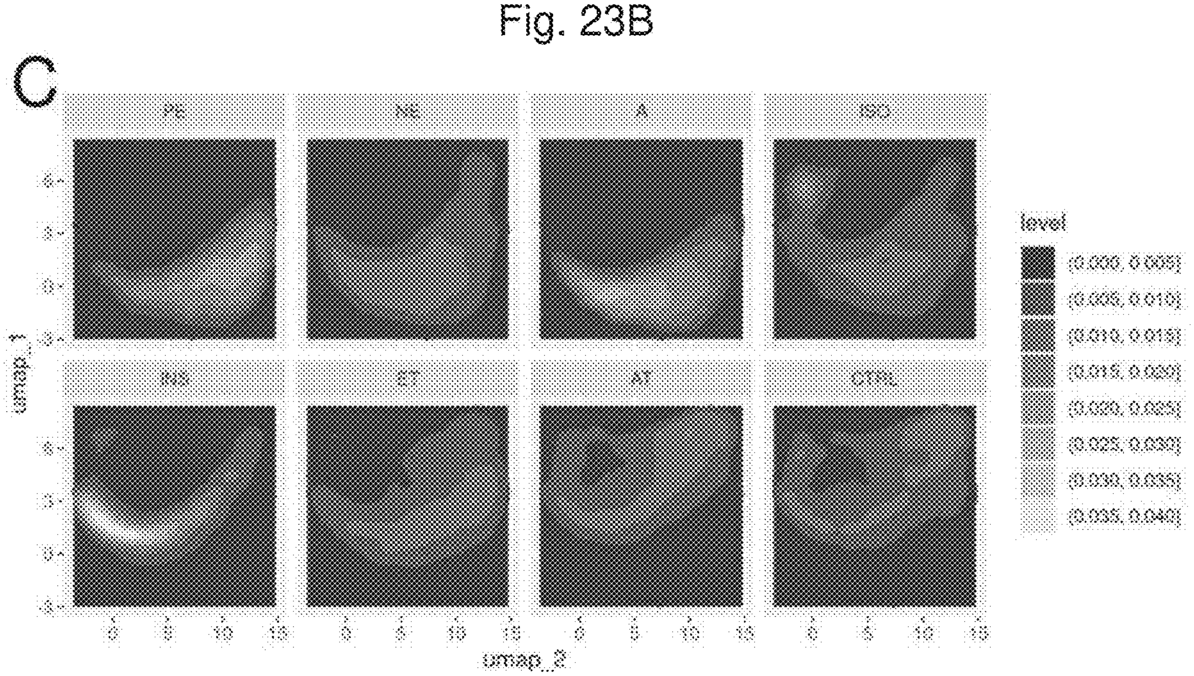

FIGS. 23*b* and 23*c*: Separate UMAPs by stimuli (B) and corresponding cellular densities (C).

Figure 23D:
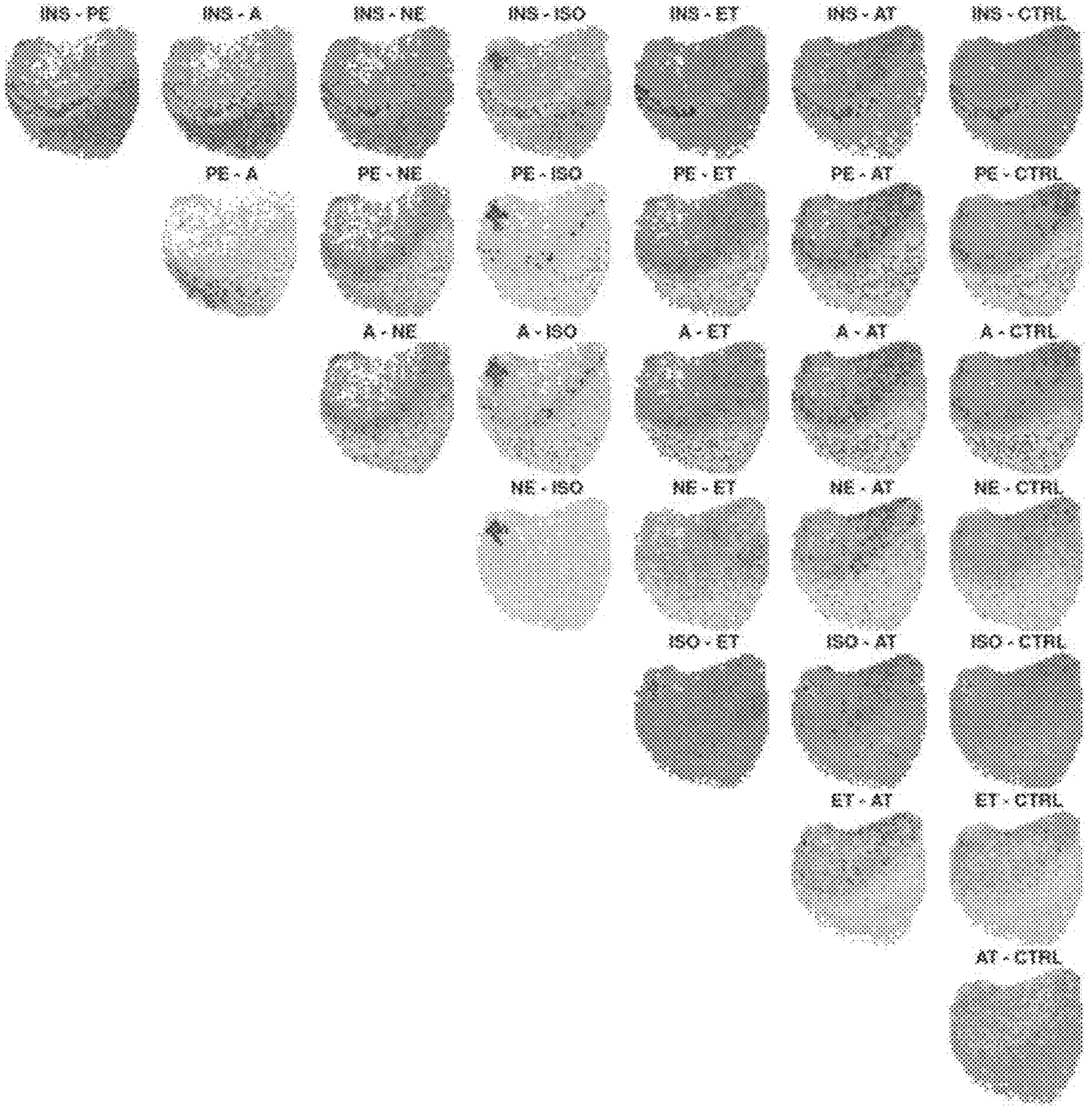

FIG. 23*d*: Pairwise differences between stimuli, in rates (50×50b bins). Quantification of stimulus induced differences, differences of binned and normalized data (50×50 grid, rate differences were calculated: x minus y axis). The r differences (upper and lower 5%) are colored in red and green. Data information: single cell data of n=1 experiment is shown.

Figure 24A:
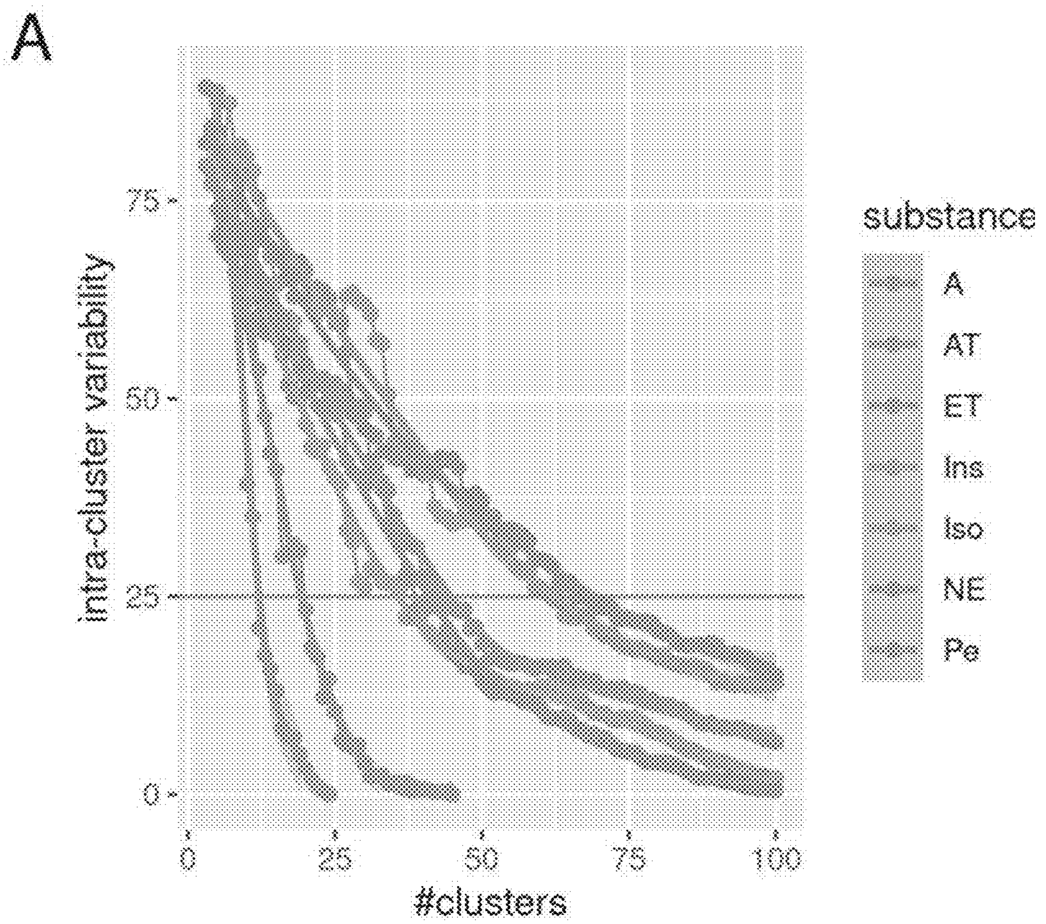

FIG. 24*a*: Selection of threshold for intracluster variability, related to FIGS. 8 and 23, and STAR methods. A: Intracluster variability for increasing number of clusters for all substances.

Figure 24B:
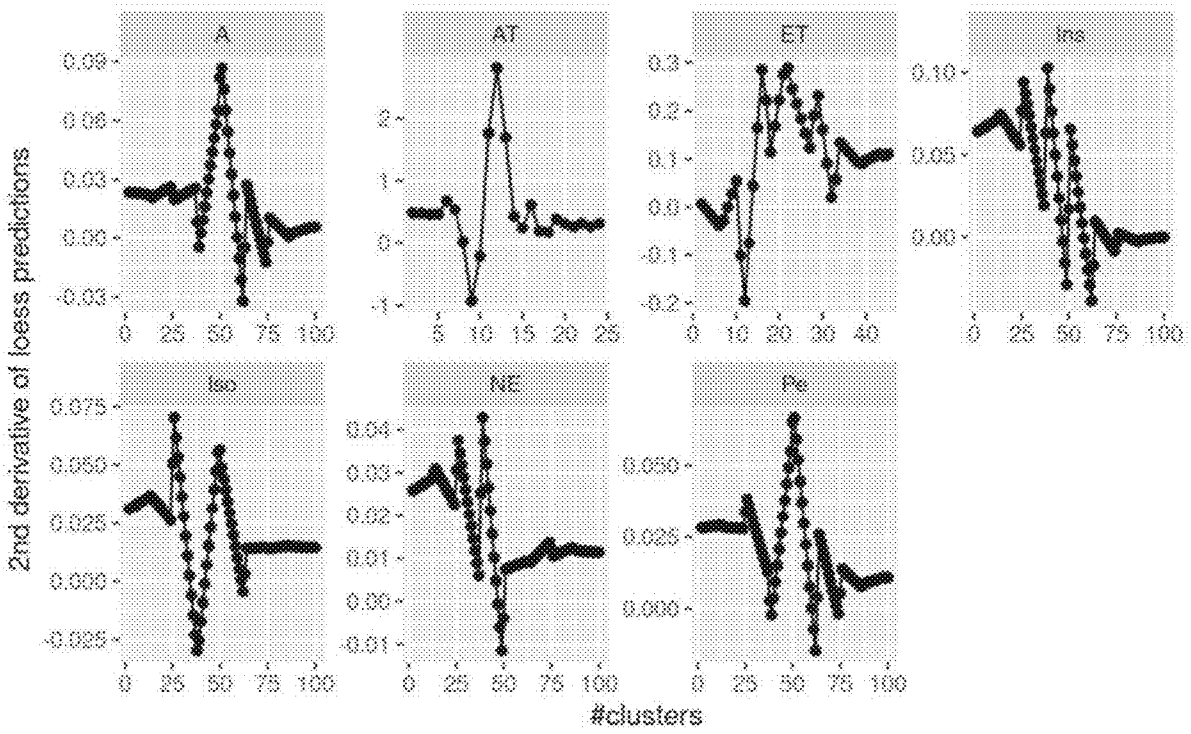

FIG. 24*b*: Second derivative of loess fits.

Figure 24C:
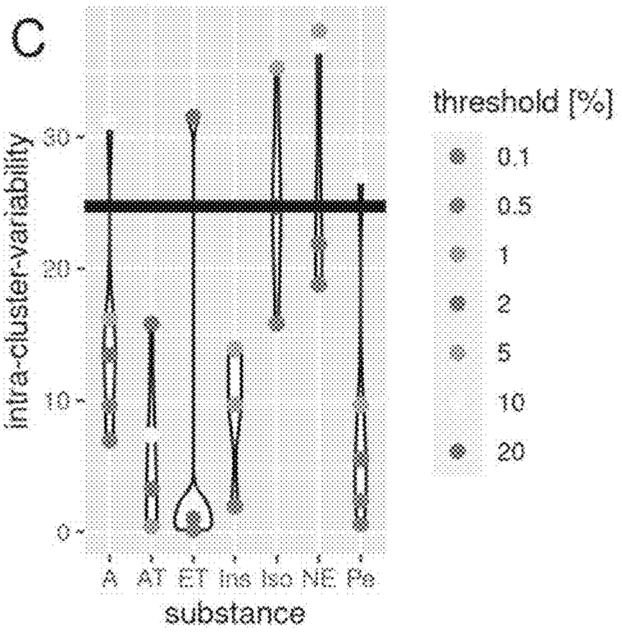

FIG. 24*c*: Maximum intracluster variability per threshold and median value of all threshold (black horizontal line).

Figure 25B:
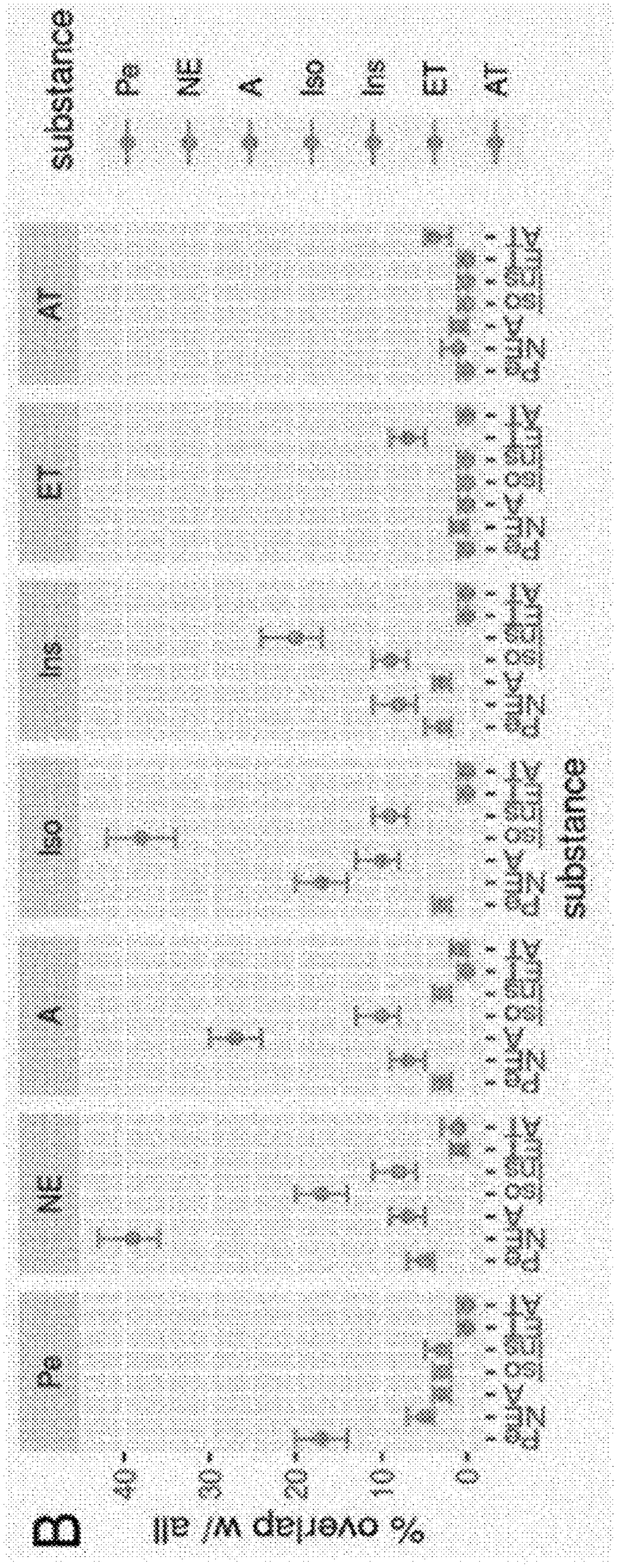

FIG. 25: Similarity of selected features, related to FIG. 23. Overlap of features between substance treatments (non-directed). Absolute number of features (A) and fractions (B) with 95% Wilson confidence intervals (number of features from all 661 unique features).

Figure 26:
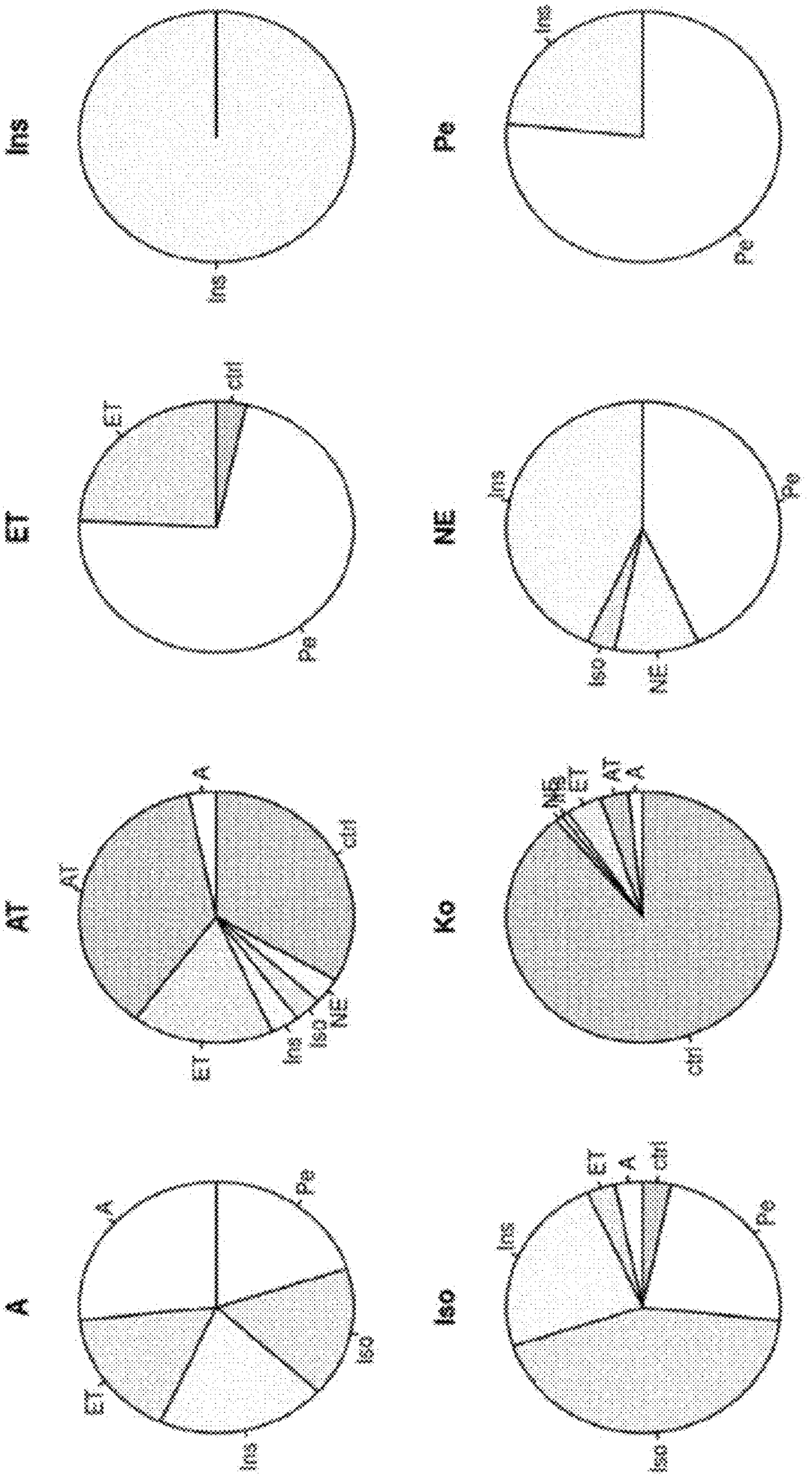

FIG. 26: Re-classification of differential hypertrophy stimuli, related to FIG. 23. Stimulus specific models were trained using Lasso regression per substance (control vs. treated per concentration, logistic regression). Then all data was classified with all models, labeling of substance (irrespective of concentration) was inferred from models with highest probability (>0.5). Fractions below 0.1% are not shown. K0=CTRL.

Figure 27:
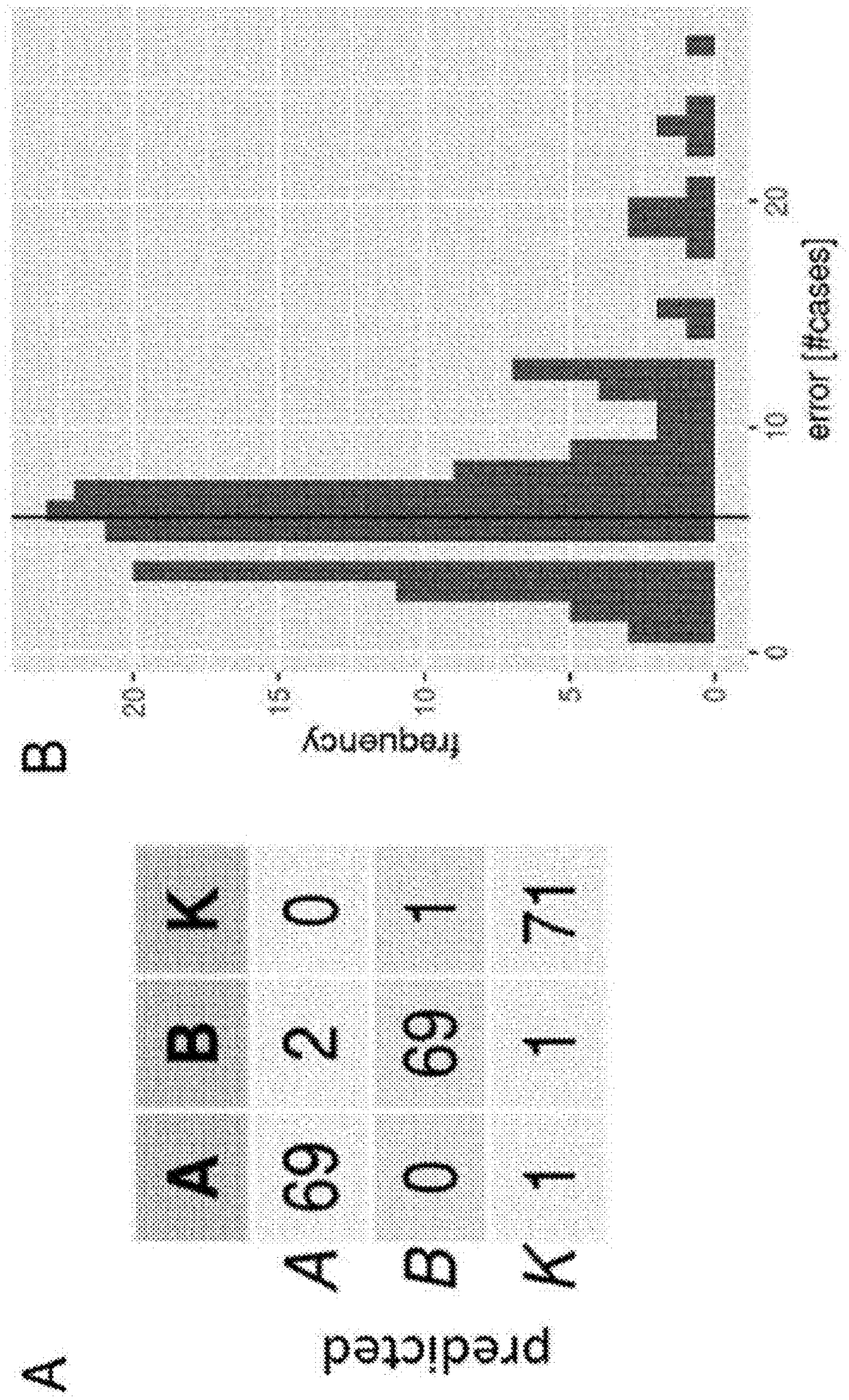

FIG. 27: Random forest classification of preTAVR (A), postTAVR (B) and healthy controls (K), related to FIG. 10. A: Accuracy of classification per well: The table shows true vs. predicted classes. B: Error for all permutations of training and test set with fixed group sizes as in A. Median number of misclassified wells are 5. Data information: Training set consisted of patient 1,2,3, K1, K2, K3, K4; test set consisted of patient 4, 5, K5, K6 for A. In B all permutations were used.

FIG. 28: Required structure of CellProfiler output data and metadata files.

Figure 29:
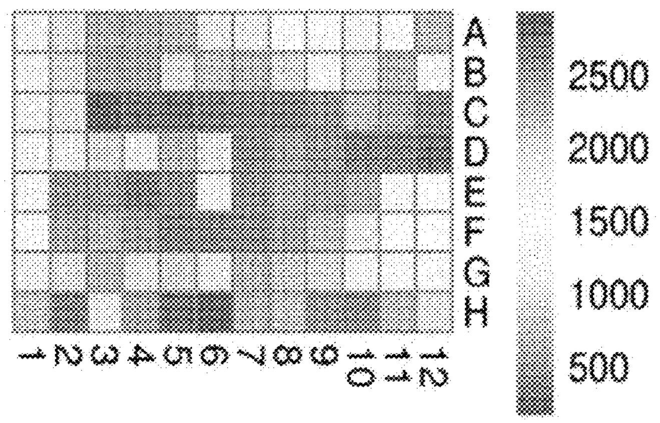
Figure 29:
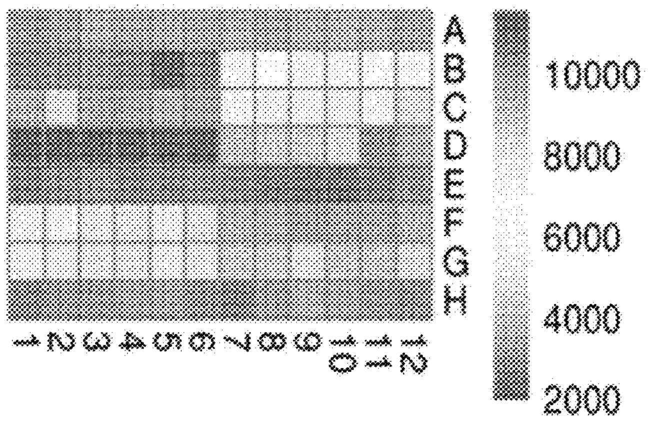

FIG. 29: QC plots for numbers of cells, cell size per well (median) and plate treatment layouts.

Figure 30:
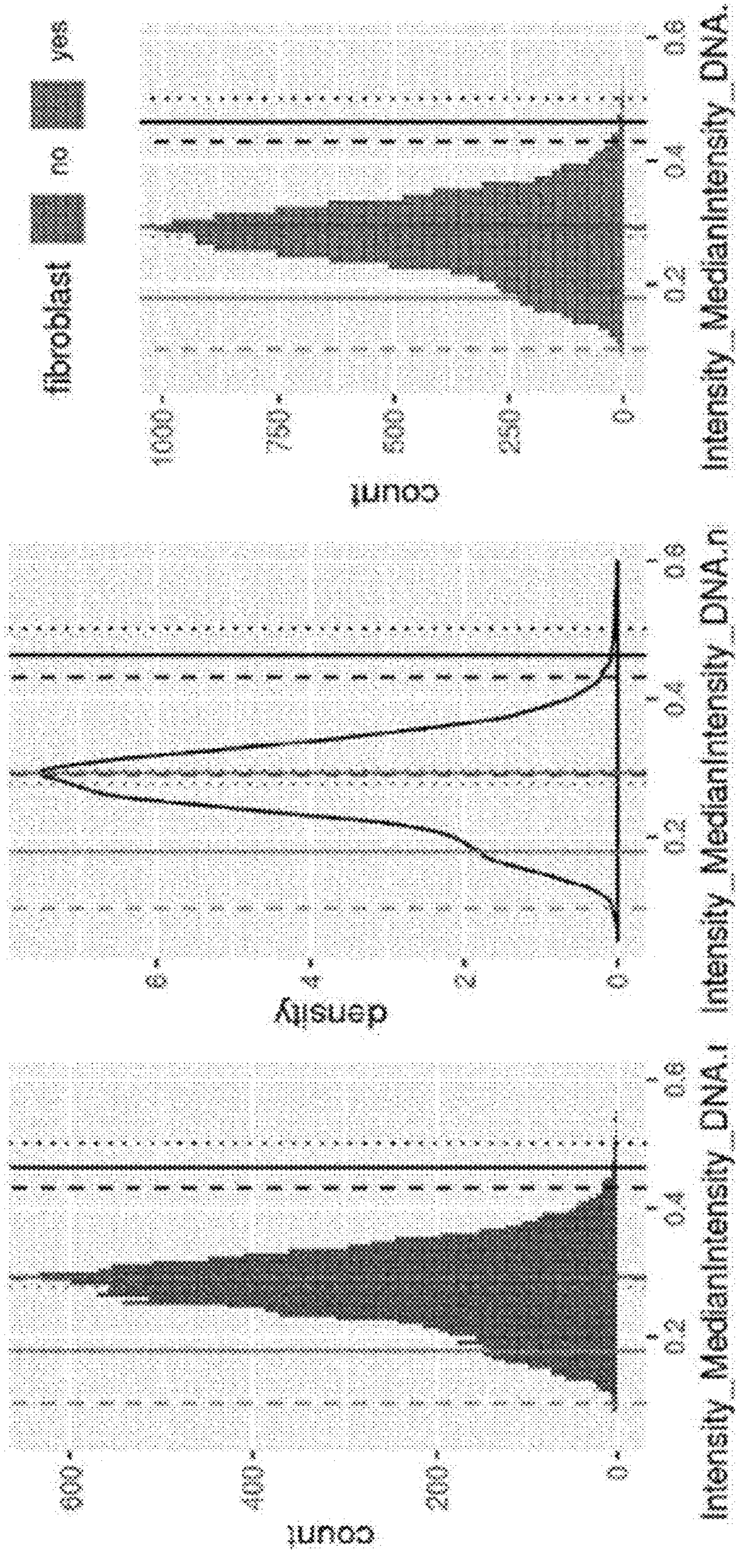

FIG. 30: Threshold identification for the differentiation between fibroblasts and cardiomyocytes. Left: histogram with calculated cutoffs (see Sec. 3.5), corresponding density (middle) and histogram with group assignments (right). Solid (median), dashed (10%) and dotted (90%) quantiles. Bold lines: Constraints on cutoff identification (xCut, xMinGlobMax).

Figure 31:
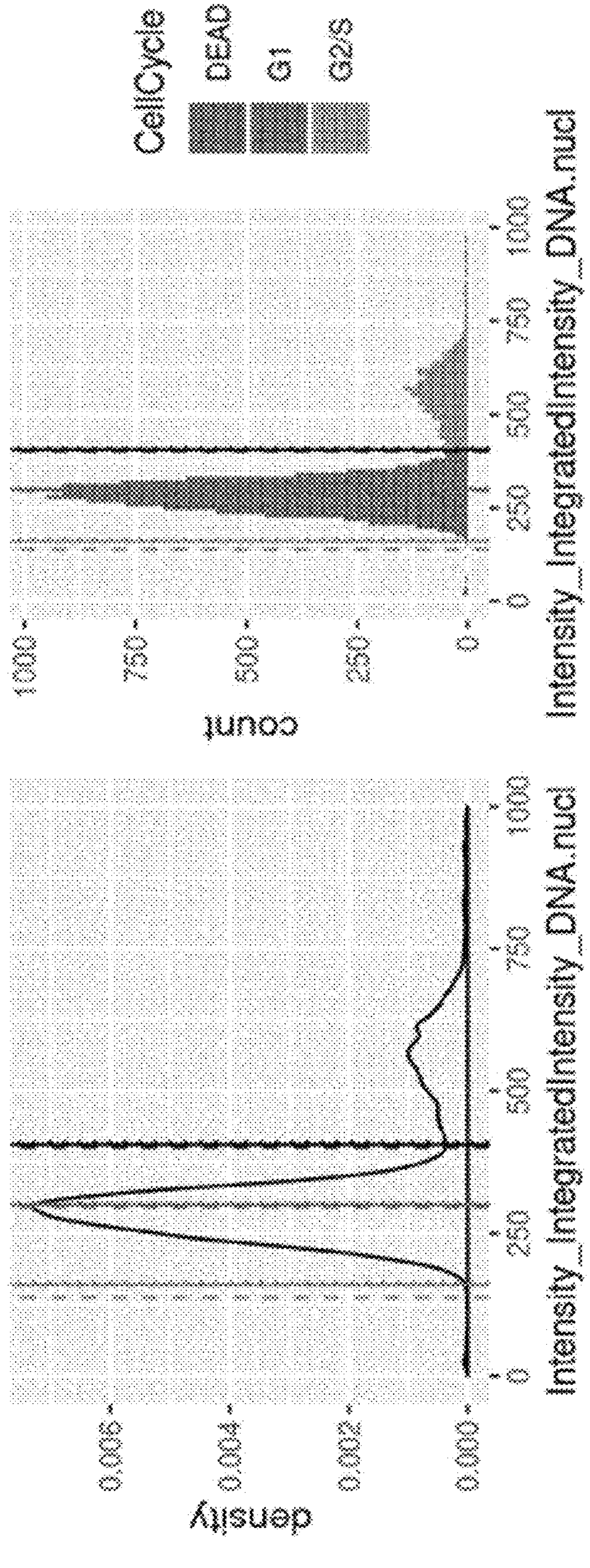

FIG. 31: Threshold identification for cell cycle assignment. Left: density with calculated cutoffs (see Sec. 3.5); solid (median), dashed (10%) and dotted (90%) quantiles and histogram of cell-cycle assigned cells (right).

Figure 32:
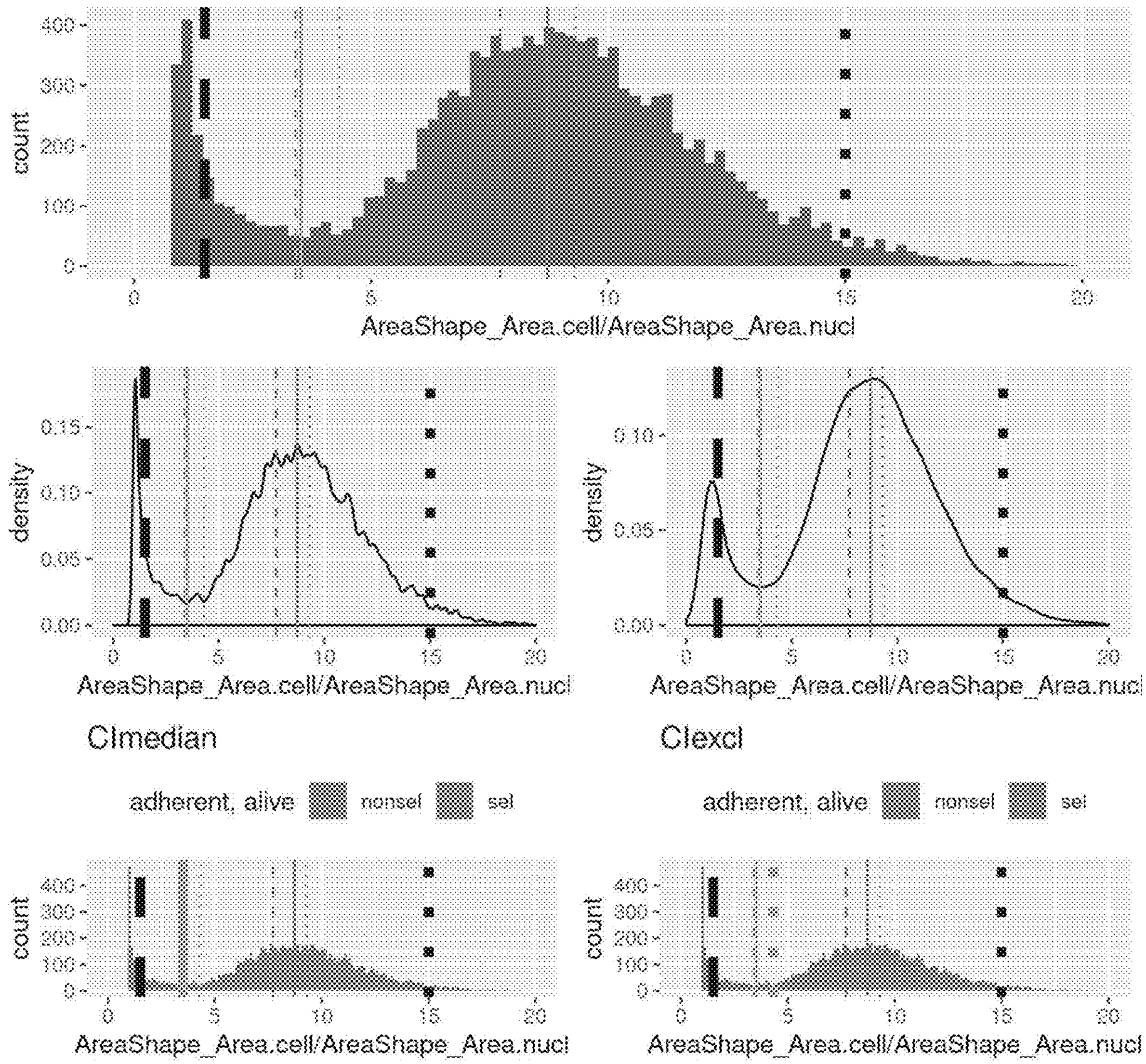

FIG. 32: Threshold identification for identification of attached, vital cardiomyocytes. Upper row: histogram of ratio distribution. Middle: different bandwidths for density estimation (left: 0.1, right: auto). Bottom: Differently selected cutoffs (left: median CImedian, right: 90% CIexcl quantile) of the left minimum. Solid (median), dashed (10%) and dotted (90%) quantiles.

Figure 33:
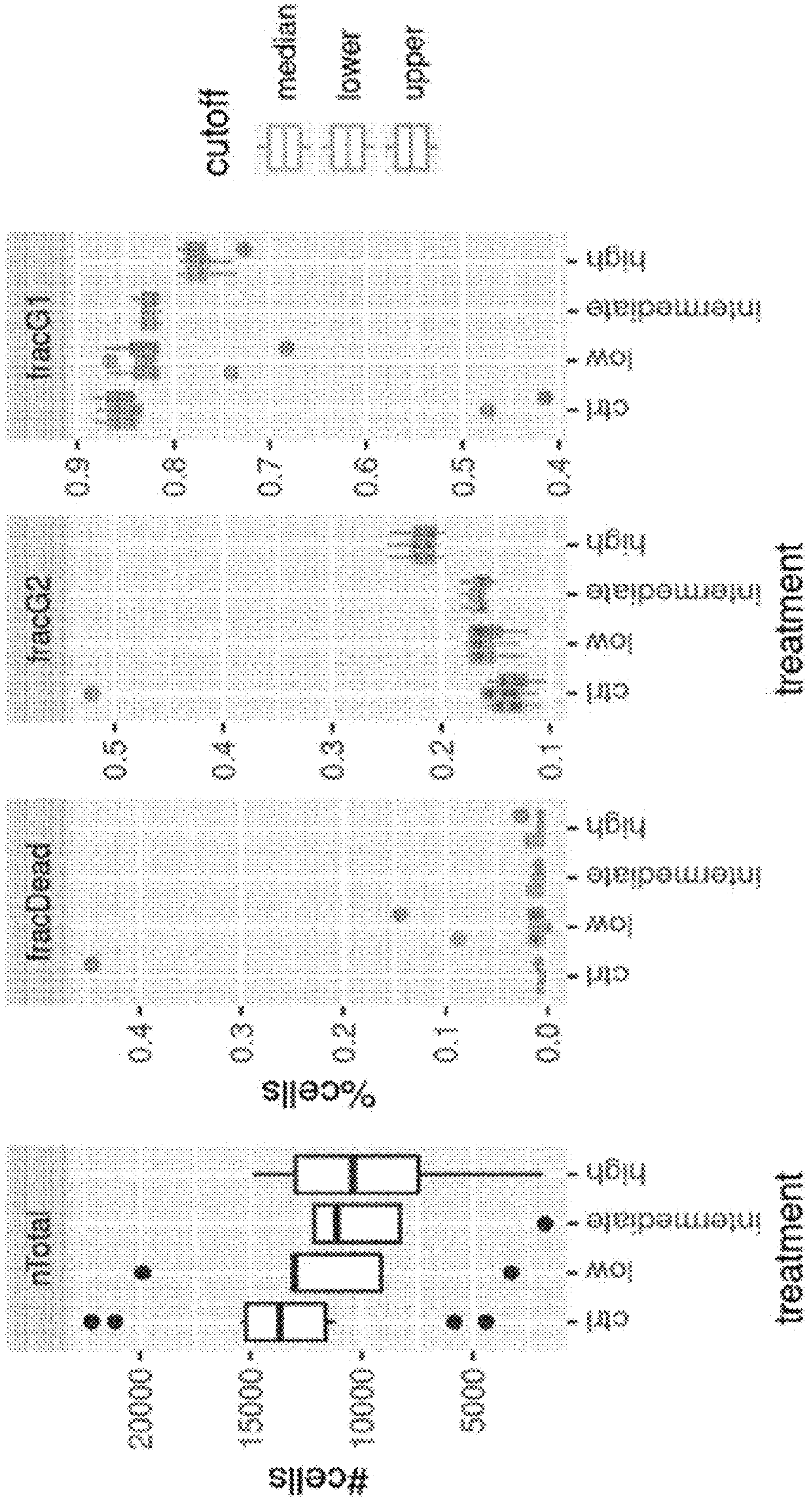

FIG. 33: Cell cycle distribution for increasing concentrations for a given treatment. Left: Numbers of cells, right: fractions of cells in the respective cell cycles with different cutoffs used to separate populations.

Figure 34:
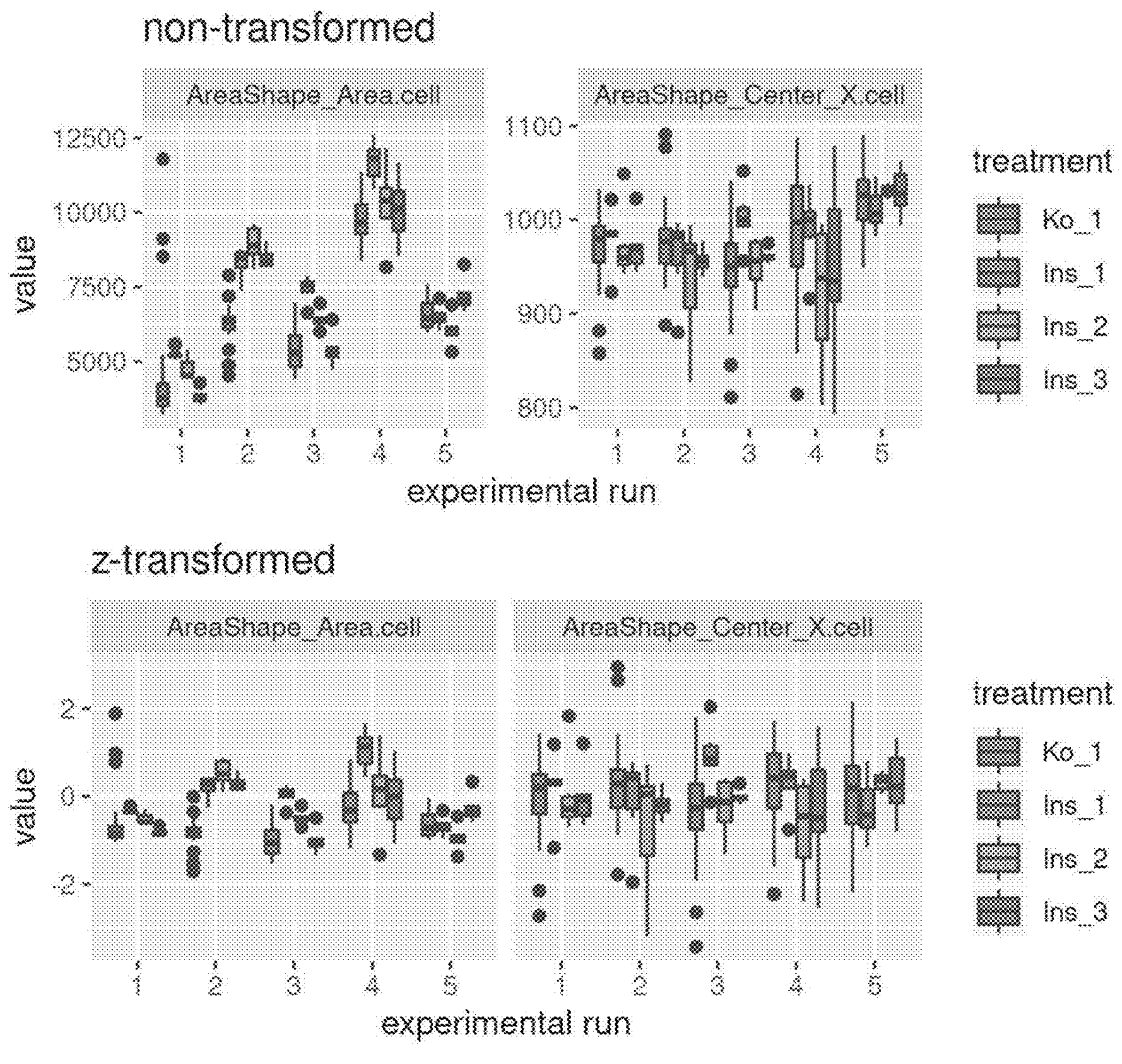

FIG. 34: Non- and z-transformed data.

Figure 35:
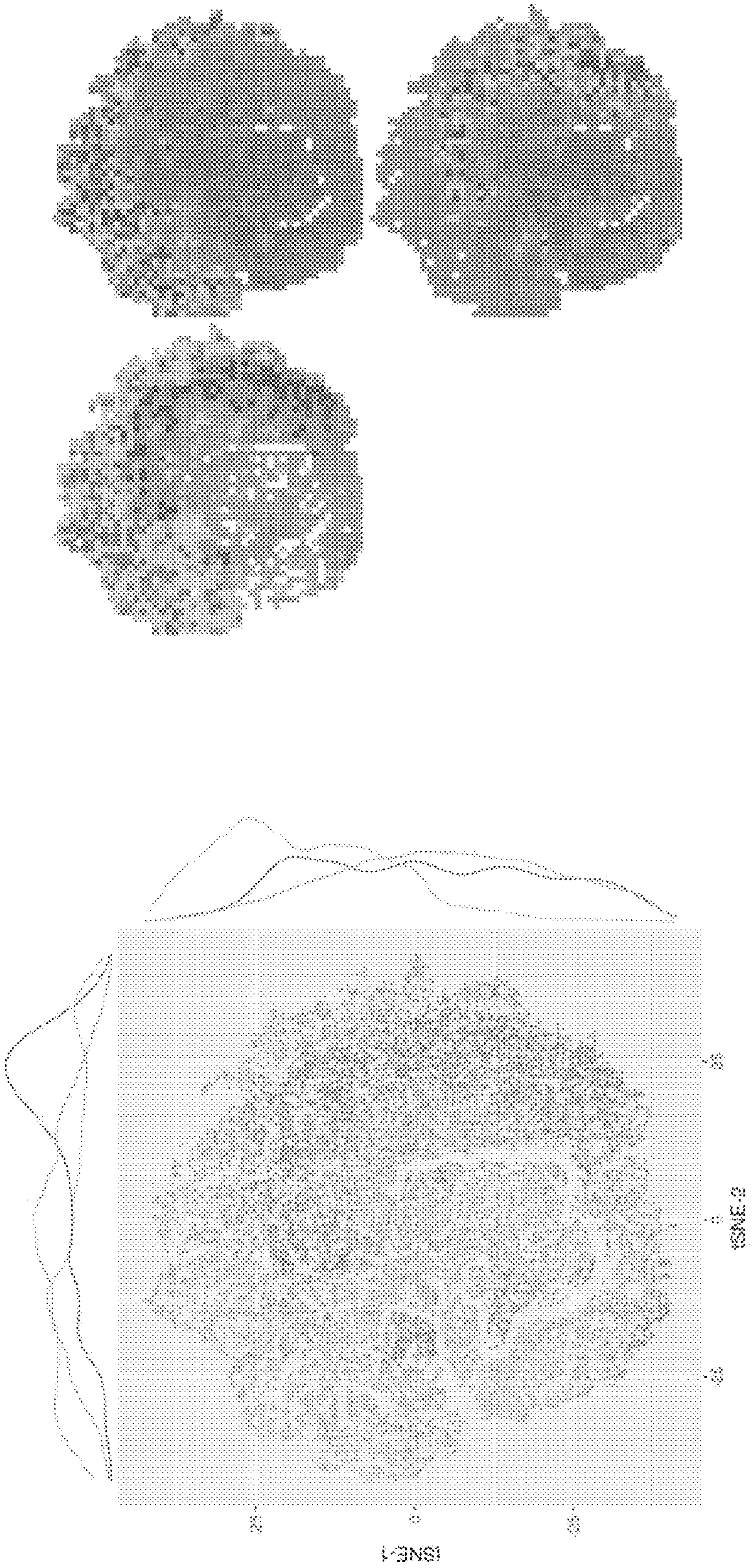

FIG. 35: Representative single-cell analysis results. Left: t-SNE of data treated with three treatments. Right: difference maps with 2.5% and 97.5% quantiles used for color code thresholding to highlight differences in population composition.

Figure 36:
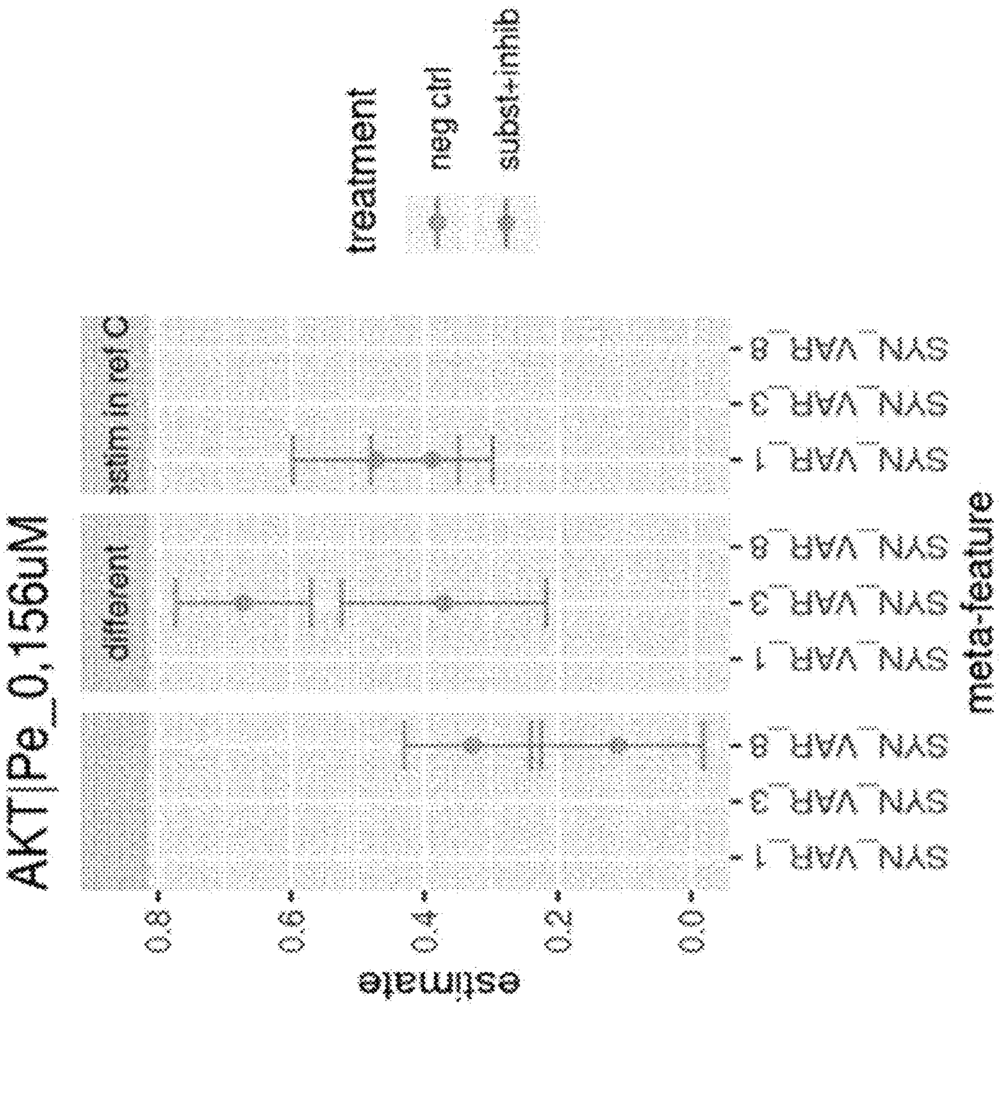

FIG. 36: Qualitatively different metrics for the evaluation of similarity between negative controls and substance+ inhibitor treated cells on meta-feature level.

Figure 37:
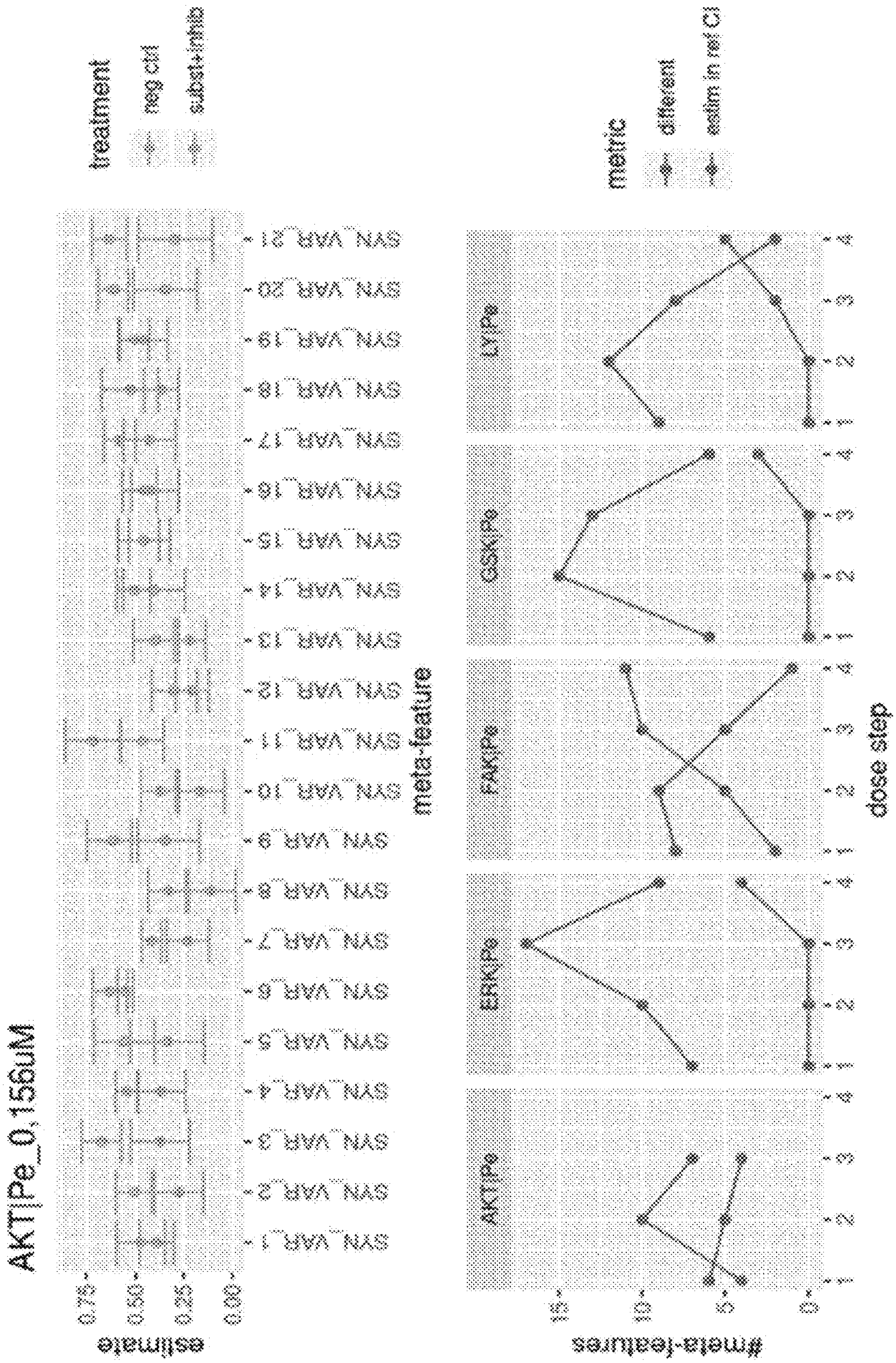

FIG. 37: Representative data showing the quantification of similarity between negative controls and substance+ inhibitor treated cells for meta-features.

Figure 38:
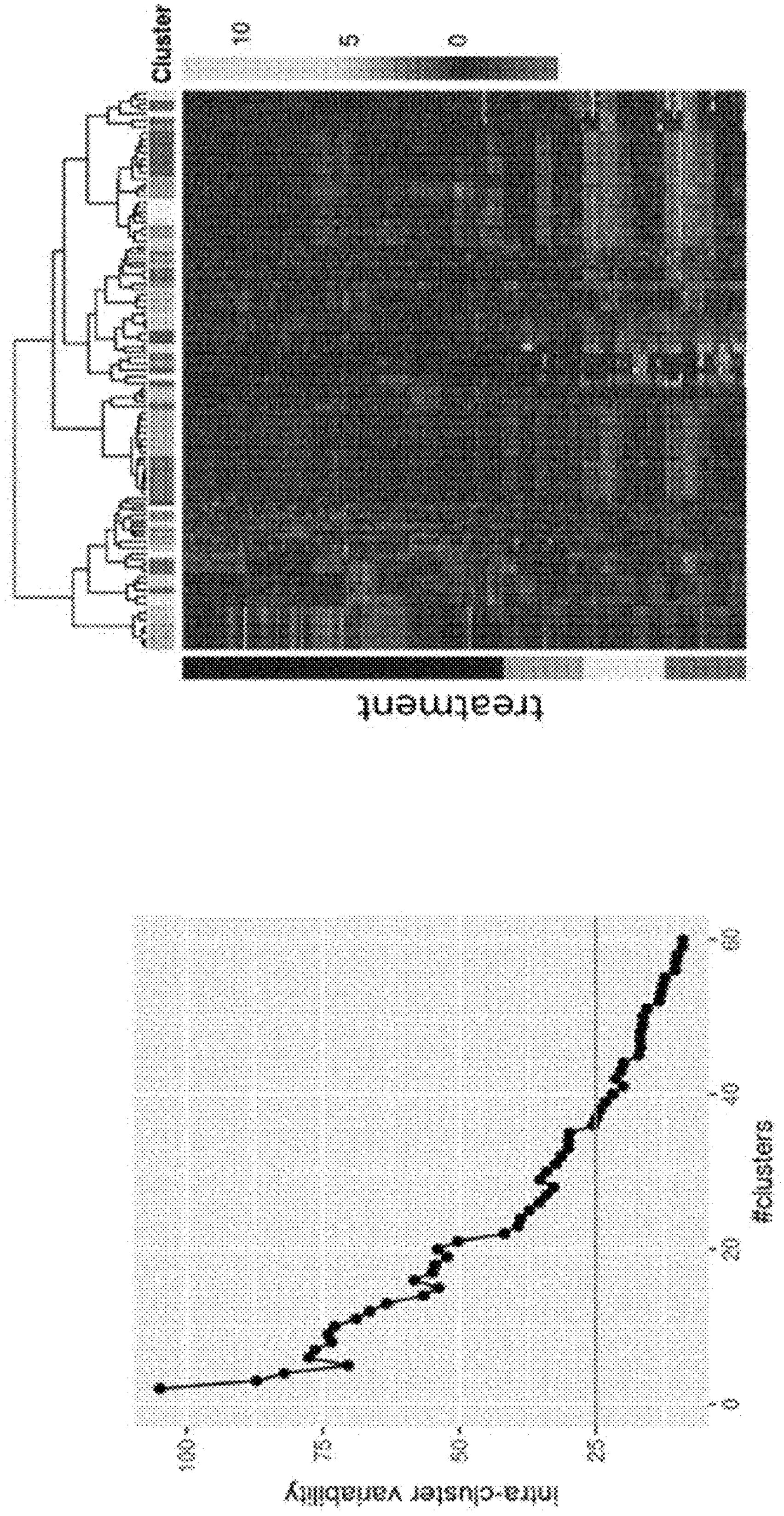

FIG. 38: Intra-cluster variability for increasing numbers of clusters (left) and heatmap of selected features with a representative clustering.

Figure 39:
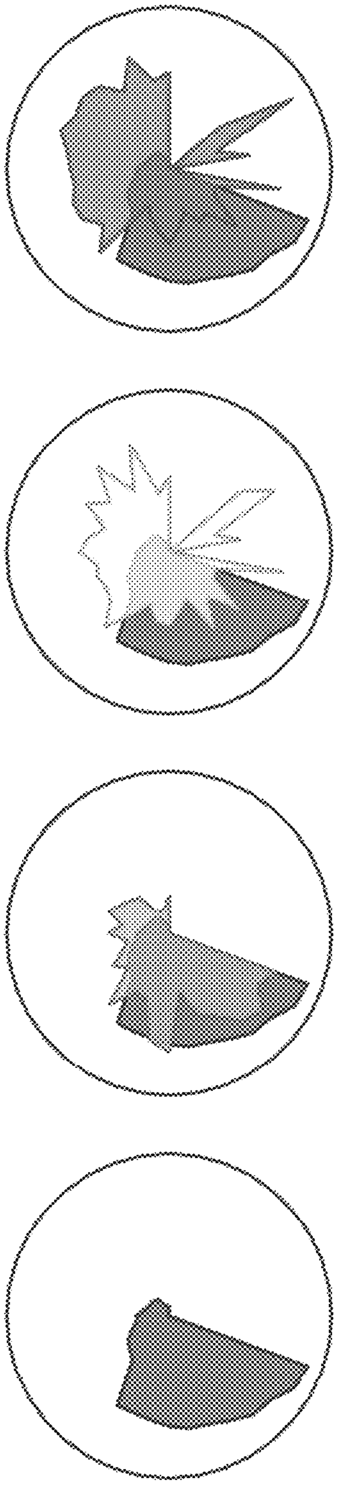

FIG. 39: Radar plots of representative data showing meta-features for increasing substance concentrations.

DESCRIPTION OF THE PREFERRED EMBODIMENTS

FIGS. 1 and 2 depict a schematic illustration of a sequence of steps and a flow diagram, respectively, for a method 200 of determining a set of meta-features for comparing samples of biological cells according to an exemplary embodiment of the invention.

In the example of FIG. 1, the method 200 is executed using a control sample 100A and a reference sample 100B. Each of the samples 100A, 100B comprises a plurality of cells 102, which are e.g. prepared in one or more wells of a multi-well plate (not shown). For illustration purposes, only a small number of cells is shown in FIG. 1. The samples 100A, 100B may contain a larger number of cells, for example between 1 000 and 10 000 cells each. In the example of FIG. 1, the cells 102 are all of the same type and may for example be heart cells, in particular cardiomyocytes such as primary neonatal rat cardiomyocytes (NRCM) or inducible progenitor derived cardiomyocytes (hiPSC-CM). In other examples, the samples 100A, 100B may comprise cells of different types, e.g. a mixture of cells for modelling a physiological environment, in particular a physiological environment in the heart. In some examples, the cells may be derived from a non-primary cell line, e.g. a HL-1, H9C2, or AC16 cardiac cell line. Each of the cells 102 comprises a nucleus 104 and may contain a biochemical substance or biomolecule 106, for example a certain protein, that is labelled with an imaging marker, e.g. a fluorescent imaging marker such as green-fluorescent protein (GFP).

The reference sample 100B was exposed to a reference substance that has a known functional, physiological, pathological, and/or morphological effect on the cells 102, e.g. a stimulus substance being a mediator in a cardiovascular condition, e.g. as detailed below. In contrast, the control sample 100A is not exposed to the reference substance, but otherwise prepared in the same way as the reference sample 100B. Preferably, the reference sample 100B comprises a plurality of individual samples (not shown), each of which may e.g. be formed by one or more wells, wherein each of the individual samples was exposed to a different dose of the reference substance, e.g. as detailed below.

The method 200 comprises, at step 202, receiving parameter values of a set of cell parameters $p_1, p_2, \ldots, p_N$, each of which quantifies a property associated with a single cell 102 in one of the samples 100A, 100B. A first set of parameter values 108A is received, which comprises the values of the cell parameters $p_1, p_2, \ldots, p_N$ for each of a plurality of cells $a_1, a_2, \ldots, a_{mA}$ in the control sample 100A. A second set of parameter values 108B is received, which comprises the values of the cell parameters $p_1, p_2, \ldots, p_N$ for each of a plurality of cells $b_1, b_2, \ldots, b_{mB}$ in the reference sample 100B.

The parameter values may for example have been determined from one or more microscopic images of the respective sample 100A, 100B, e.g. using an automated image analysis tool such as CellProfiler, see A. E. Carpenter et al., *Genome Biol.,* 7(10):R100 (2006). In particular, a plurality of images may have been taken for each sample 100A, 100B at different wavelengths, e.g. at wavelengths associated with certain imaging markers or stains, and/or using different microscopy techniques, in particular different illumination techniques. Additionally or alternatively, the parameter values may have been determined using other cell analysis techniques such as mass cytometry and/or using assays for determining one or more specific cell properties, e.g. the myocardial contractility. The number of parameters N may for example be between 500 and 2000. In some examples, the parameter values 108A, 108B may have been extracted beforehand and may e.g. be provided on a machine-readable storage medium. In other examples, the method 200 may also comprise extracting the parameter values and in some cases also performing the corresponding measurements, e.g. taking the one or more microscopic images. Preferably, the parameter values 108A, 108B are normalized and/or standardized, e.g. by computing the corresponding standard scores (z-scores) in step 202 or beforehand.

The set of cell parameters $p_1, p_2, \ldots, p_N$ comprises a plurality of geometrical cell parameters characterizing a size and/or shape of the respective cell 102 or a part thereof. The geometrical cell parameters may for example comprise the cross-sectional area of the cell 102, the perimeter of the cell 102, the aspect ratio of the cell 102, and the cross-sectional area of the nucleus 104.

The set of cell parameters further comprises a plurality of structural parameters characterizing a structure and/or topography of the respective cell 102 or a part thereof. The structural parameters may for example comprise a roughness of the membrane of the cell 102, a variance of the measured intensity in the cytoplasm of the cell 102, a correlation length of the measured intensity in the cytoplasm, a mean or median intensity associated with the cell 102, and a contrast associated with the cell 102. The structural parameters may in particular comprise Haralick features obtained from a co-occurrence matrix of the one or more microscopic images or a part thereof.

In addition, the set of cell parameters comprises a plurality of functional parameters characterizing a concentration and/or a distribution of a biomolecule or a biochemical substance in the respective cell 102. In some examples, the functional parameters may comprise structural parameters associated with the biomolecule or biochemical substance, e.g. structural parameters extracted from a microscopic image taken at an emission wavelength of an imaging marker that the biomolecule or biochemical substance is labeled or stained with. The functional parameters may for example comprise parameters associated with the biomolecule 106, e.g. a mean or median fluorescence intensity and parameters pertaining to a distribution of the fluorescence intensity within the cell. The functional parameters may further comprise parameters associated with another biochemical substance or biomolecule in the cell 102 such as nuclear DNA, which may e.g. have been stained prior to taking the one or more microscopic images. The functional parameters may for example comprise a mean intensity and parameters pertaining to a distribution of the intensity within the cell 102 at the respective wavelength.

Furthermore, the set of cell parameters comprises a plurality of proximity parameters associated with one or more cells in the vicinity of the respective cell 102. The proximity parameters may for example comprise a number of cells in a pre-defined radius around the cell 102, a number of cells touching the cell 102, and a percentage of the border of the cell 102 in contact with other cells.

The method 200 may also comprise determining parameter values for one or more secondary cell parameters for each of the cells $a_1, \ldots, a_{mA}$ and $b_1, \ldots, b_{mA}$. The parameter values for the secondary cell parameters are determined from the received parameter values 108A, 108B of the set of cell parameters $p_1, \ldots, p_N$, which may thus also be referred to as the primary cell parameters. Subsequently, the secondary cell parameters are added to the set of cell parameters, i.e. the respective parameter values are added to the set of parameter values 108A and 108B, respectively (not shown).

The secondary cell parameters may for example comprise a plurality of relative parameters such as ratios and differences between primary cell parameters. The secondary cell parameters may in particular comprise a plurality of categorization parameters assigning the respective cell 102 to a category based on the primary cell parameters, wherein the category may e.g. be a type of the cell 102, state of the cell 102, or a subpopulation that the cell 102 is assigned to. The assignment of the respective cell may for example be based on thresholds for one or more primary cell parameters. Preferably, the respective thresholds are determined dynamically based on the respective primary cell parameter, e.g. by identifying modes of a multimodal distribution and defining a corresponding threshold separating the modes. For example, a minimum in the distribution of the respective parameter values may be identified. Cells with a parameter value below the minimum or below a lower confidence bound for the minimum may be assigned to a first category, whereas cells with a parameter value above the minimum or above an upper confidence bound for the minimum may be assigned to a second category. This may further be generalized to multi-modal distributions with more than two categories as well as more elaborate methods for defining the thresholds, e.g. by a fit to the distribution. By way of example, this may e.g. allow for distinguishing fibroblasts and cardiomyocytes based on a median intensity associated with stained nuclear DNA, determining a cell cycle state of the cells (e.g. apoptotic, $G_1$ phase, S phase/$G_2$ phase) based on an integrated intensity associated with stained nuclear DNA as illustrated in FIG. 12*a*, and identifying non-intact cells or debris based on a ratio of the cross-sectional areas of the cell 102 and its nucleus 106 as illustrated in FIG. 12*b*.

In some embodiments, the method 200 may also comprise selecting a subset of cells from the plurality of cells 102 in the control sample 100A and/or in the reference sample 100B and performing the steps described in the following only for the selected subset. For example, apoptotic cells, non-intact cells and/or cells not matching a predetermined cell type may be excluded.

In step 204, the parameter values 108A, 108B of the two samples 100A, 100B are compared to each other, yielding a plurality of comparison metrics 110, each of which is associated with one of the cell parameters $p_1, \ldots, p_N$. The comparison may be performed for a subset of the cell parameters or for each of the cell parameters as illustrated in FIG. 1. Based on the comparison metrics 110, a set of relevant parameters 112 is selected from the set of cell parameters $p_1, \ldots, p_N$. In FIG. 1, the cell parameters 112 identified as relevant are marked with an "X", whereas the cell parameters 114 identified as not relevant are represented by empty squares.

The comparison metric 110 may for example indicate whether the parameter values of the respective cell parameter differ between the control and reference samples 100A, 100B. In one example, the comparison metric is the difference between the mean or median of the parameter values for the cells 102 in the control sample 100A and the mean or median of the parameter values for the cells 102 in the reference sample 100B. The corresponding cell parameter may be identified as relevant if the difference is larger than a predetermined threshold.

Preferably, the comparison metric 110 comprises a significance measure that characterizes the statistical significance of the difference or equivalence between the parameter values for the control and reference samples 100A, 100B. The significance measure may for example be an error of the difference of the mean or median or may be based thereon, wherein the error may comprise a statistical and/or systematic error. The significance measure may in particular be a measure for null hypothesis testing, e.g. a p-value. The corresponding cell parameter may be identified as relevant if the significance measure fulfills a pre-defined conditions e.g. if the significance measure indicates at least a pre-defined significance, e.g. a p-value below 0.01 or below 0.001.

In some embodiments, the comparison metric 110 may comprise additional measures, for example a validity measure based on a statistical cross-validation of a statistical model for the respective cell parameter, e.g. using subsets of cells in the sample 100A, 100B. In one example, each of the samples 100A, 100B comprises a plurality of wells and a k-fold cross validation is performed by partitioning the samples 100A, 100B into k subsets, wherein each subset comprises e.g. between one and four wells of each sample 100A, 100B. The validity measure may for example quantify a mean prediction error of the cross-validation, e.g. when comparing the mean or median difference of the parameter values in one subset with the mean or median difference of the parameter values in the remaining k−1 subsets for each permutation of subsets. The corresponding cell parameter may only be identified as relevant if the validity measure fulfills a pre-defined condition, e.g. if the mean prediction error of the cross-validation is smaller than a pre-defined threshold.

In step 206, the set of relevant parameters 112 is grouped into a plurality of clusters $C_1, C_2, \ldots, C_L$ of correlated parameters. For this, correlations between the parameter values of the relevant parameters 112 are assessed, e.g. in the parameter values 108A of the control sample 100A and/or in the parameter values 108B of the reference sample 100B, or a subset thereof. For example, a pairwise similarity metric may be determined for each pair of relevant parameters 112, wherein the similarity metric quantifies the degree of correlation between the respective parameters. The similarity metric may for example be the Euclidean distance between the parameter values of the two parameters.

Relevant parameters exhibiting a high degree of correlation may then be grouped into a cluster using a clustering algorithm. Preferably, each relevant parameter is only contained in a single cluster. The clustering algorithm may in particular be an iterative algorithm for hierarchical cluster analysis based on a linkage criterion specifying one or more conditions for merging parameters or clusters. In one example, the clustering method is Ward's minimum variance method, wherein clusters are formed by successively merging clusters exhibiting the minimum increase of the intra-cluster variance after merging. The number of iterations may be limited by a cutoff, which may e.g. specify a maximum number of iterations, a maximum number of clusters or preferably a threshold for the intra-cluster variability, e.g. a cutoff for the intra-cluster variance. In one example, this cutoff may be determined dynamically in step 206, e.g. based on a slope of the average or maximum inter-cluster variance as a function of the number of clusters.

As a result of the clustering based on correlations, the clusters $C_1, \ldots, C_L$ may comprise different numbers of relevant parameters. In particular, one or more clusters may only comprise a single relevant parameter in some cases. On the other hand, some clusters may also comprise a large number of parameters, e.g. more than 20, in some cases more than 50. The cutoff for the clustering algorithm may for example be chosen such that the number of clusters is in the range between 5 and 100.

In step 206, meta-features $f_1, f_2, \ldots, f_L$ are defined, wherein each meta-feature is associated with one of the clusters $C_1, \ldots, C_L$. Preferably, one meta-feature is defined for each of the clusters. Each meta-feature is a mathematical function of the parameters in the respective cluster such that for each cell a feature value of the meta-feature can be calculated from the parameter values of the respective relevant parameters. In one example, the meta-feature is the mean or median of the parameters associated with the meta-feature. In other examples, the meta-feature may e.g. be a weighted average of the respective parameters. The weight of a parameter may for example be based on a similarity metric between the parameter and the other parameters of the cluster.

The meta-features defined in step 206 may later on be used for characterizing other samples of cells, e.g. for studying the effect of a test substance on a test sample using the method 400 described below with reference to FIGS. 3 and 4. For this, the method 200 may e.g. comprise storing information pertaining to the relevant parameters 112 identified in step 204 and to the meta-features defined in step 208 on a machine-readable storage medium. The information may for example comprise the mathematical functions defining the meta-features or rules for obtaining these functions as well as identifiers of the relevant parameters 112 for selecting the relevant parameters 112 from the set of cell parameters.

FIGS. 3 and 4 depict a schematic illustration of a sequence of steps and a flow diagram, respectively, for a method 400 of studying an effect of a test substance on a test sample of biological cells according to an exemplary embodiment of the invention.

In the example of FIG. 3, the method 400 is executed using a control test sample 300A and a test sample 300B. The samples 300A, 300B are similar to the control and reference samples 100A, 100B of FIG. 1. In particular, the samples 300A, 300B contain cells 102 of the type as the sample 100A, 100B, e.g. cardiomyocytes, and are prepared in the same way, e.g. by staining parts of the cells 102 and/or labelling one or more biomolecules or biochemical substances in the cells 102 as described above.

In step 402, the test sample 300B is exposed to the test substance. The test substance may for example be a candidate substance that is to be tested as a potential inhibitor for a medical condition, e.g. for a cardiovascular condition. Alternatively, the test substance may be a sample of a patient, e.g. blood serum or blood plasma, that is for example to be tested to assess the risk of developing a certain medical condition. In one example, the blood plasma may e.g. contain one or more hypotrophy inducing substances, which may lead to a growth of the cardiomyocytes upon exposure as illustrated in FIG. 3. This may e.g. indicate that the patient is at risk of developing a cardiovascular condition such as hypertrophic cardiomyopathy, amyloidosis and/or aortic stenosis. In some examples, the test substance may comprise two or more substances, e.g. a patient's sample and a stimulus substance being a mediator for the medical condition or a patient's sample and a known inhibitor for a mediator for the medical condition. The test control sample 300A is not exposed to the test substance. In some examples, the test control sample 300A may not be exposed to any substance or may instead be exposed to a different substance, e.g. only the stimulus substance or the known inhibitor.

For studying the effect of the test substance, the method 400 uses a set of relevant parameters 112 and a set of meta-features $f_1, \ldots, f_L$ that are determined with a method of determining a set of meta-features according to any one of the embodiments described herein, e.g. the method 200. In some examples, the method 400 may also comprise executing the corresponding method in its entirety or at least in part, e.g. the method 200. In other examples, this may have been done beforehand and the method 400 may comprise receiving the corresponding information, e.g. information stored on a machine-readable medium by the method 200.

Preferably, the reference substance to which the reference sample 100B was exposed is chosen based on the effect to be studied using the method 400. In particular, if the effect of the test substance is to be assessed with regard to a certain medical condition, the reference substance comprises a stimulus substance being a mediator involved in the medical condition.

The method 400 further comprises, in step 404, determining parameter values y(pi) of the set of relevant parameters 112 for each of a plurality of cells 102 in the test sample 300B. The parameter values may for example be determined as described above, e.g. from one or more microscopic images of the respective sample. In some examples, this may comprise determining parameter values for the entire set of cell parameters $p_1, \ldots, p_N$ and/or determining parameter values of secondary cell parameters. In some embodiments, the method 400 may also comprise selecting a subset of the plurality of cells 102 for further analysis, e.g. as described above.

In step 406, the feature values $z(f_i)$ of the set of meta-features $f_1, \ldots, f_L$ are determined for the test sample 300B, e.g. for each of the plurality of cells 102 or a selected subset thereof. Each of the feature values is calculated from the parameter values of the relevant parameters contained in the cluster $C_1, \ldots, C_L$ associated with the respective meta-feature $f_1, \ldots, f_L$, e.g. as described above.

In step 408, the feature values for the test sample 300B are compared to the feature values for the control test sample 300A, which may e.g. have been obtained in the same way by determining the relevant parameters values for each of a plurality of cells 102 in the test control sample 300A in step 404 and by determining the features values for the test control sample 300A in step 406 from the relevant parameter values as described above.

An example for this is depicted in FIG. 3, which shows schematic illustrations of parameter values 302A for the set of cell parameters for one of the cells 102 in the test control sample 300A and of parameter values 302B for the set of cell parameters for one of the cells 102 in the test sample 300B. In addition, FIG. 3 also depicts schematic illustrations of feature values 304A for the set of meta features for the test control sample 300A and of feature values 304B for the set of meta features in the test sample 300B, wherein the feature values may e.g. be feature values associated with a single cell or may be averaged values of a plurality of cells. Due to the large number of parameters and variations between individual cells, it may be challenging to extract meaningful information from data such as the parameter values 302A, 302B. In contrast, the feature values 304A, 304B are based on data identified as relevant and provide an additional averaging as a result of the aggregation in clustered meta-features. This may facilitate assessing the effect of the test substance substantially, e.g. by quantifying a difference in the feature values between the test sample 300B and the test control sample 300A.

FIG. 5 shows a schematic illustration of a computer program product 500 according to an exemplary embodiment of the invention. The computer program product 500 comprises two sets of machine-readable instructions 500A, 500B that are executable by a processing device, e.g. the processing device 602 of the system 600 described below, which is used as an illustrative examples in the following. The instructions 500A, 500B may for example be stored on a machine-readable storage medium such as the data storage 604 of the system 600.

The first set of instructions 500A causes the processing device 602 to execute a method of determining a set of meta-features according to any one of the embodiments described herein. The set of instructions 500A may in particular cause the processing device 602 to execute the method 200.

For this, the set of instructions 500A comprises instructions 502 to receive the parameter values 108A, 108B of the set of cell parameters $p_1, \ldots, p_N$ for each of a plurality of cells 102 in the control sample 100A and for each of a plurality of cells 102 in the reference sample 100B, e.g. as described above for step 202 of the method 200. The set of instructions 500A further comprises instructions 504 to identify the set of relevant parameters 112 from the set of cell parameters $p_1, \ldots, p_N$ by comparing the parameter values 108A from the control sample 100A and the parameter values 108B from the reference sample 100B for at least one of the cell parameters, e.g. as described above for step 204 of the method 200. The set of instructions 500B further comprises instructions 506 to identify the clusters $C_1, \ldots, C_L$ of correlated parameters within the set of relevant parameters 112 based on correlations between the parameter values of the relevant parameters 112, e.g. as described above for step 206 of the method 200. The set of instructions 500A further comprises instructions 508 to define a meta-feature $f_1, \ldots, f_L$ for at least one of the clusters $C_1, \ldots, C_L$ as a mathematical function of the parameters of the respective cluster, e.g. as described above for step 208 of the method 200.

The second set of instructions 500B causes the processing device 602 to execute a method of studying an effect of a test substance on a test sample according to any one of the embodiments described herein. The set of instructions 500A may in particular cause the processing device 602 to execute the method 400.

For this, the set of instructions 500B comprises instructions 510 to expose the test sample 300B to the test substance, e.g. as described above for step 402 of the method 400. The set of instructions 500B further comprises instructions 512 to determine parameter values of the set of relevant parameters 112 for each of a plurality of cells 102 in the test sample 300B, e.g. as described above for step 404 of the method 400. The set of instructions 500B further comprises instructions 514 to determine feature values of the set of meta-features $f_1, \ldots, f_L$ for the test sample 300B, e.g. as described above for step 406 of the method 400. The set of instructions 500B further comprises instructions 516 to compare feature values of meta-features $f_1, \ldots, f_L$ for the test sample 300B to feature values of meta-features $f_1, \ldots, f_L$ for the control test sample 300A, e.g. as described above for step 408 of the method 400.

FIG. 6 depicts a schematic illustration of a system 600 in accordance with an exemplary embodiment of the invention. The system 600 comprises a processing device 602 and a data storage 602 coupled to the processing device 600. The processing device 602 may for example comprise one or more central processing units (CPU), one or more graphics processing unit (GPU), one or more field-programmable gate arrays (FPGA), one or more application-specific integrated circuits (ASIC), or combinations thereof. The data storage 602 may for example comprise a non-volatile memory such as a hard drive or flash memory and/or volatile memory such as random-access memory (RAM).

The data storage 604 stores a set of machine-readable instructions 604A, 604B for execution by the processing device 602. The instructions 604A, when executed by the processing device 602, cause the processing device 602 to receive at least one microscopic image of the test sample 300B of biological cells 102 and at least one microscopic image of the control test sample 300A of biological cells 102. The instructions 604A further cause the processing device 602 to determine parameter values of a set of relevant parameters 112 for each of a plurality of cells 102 in the test sample 300B and for each of a plurality of cells 102 in the control test sample 300A from the at least one microscopic image of the respective sample 300A, 300B, e.g. as described above for the method 400.

The instructions 604B, when executed by the processing device 602, cause the processing device 602 to determine feature values of the set of meta-features $f_1, \ldots, f_L$ from the parameter values of the set of relevant parameters 112 for the test sample 300B. The instructions 604A further cause the processing device 602 to determine feature values for the set of meta-features $f_1, \ldots, f_L$ from the parameter values of the set of relevant parameters 112 for the control test sample 300A.

The set of relevant parameters 112 and the set of meta-features $f_1, \ldots, f_L$ were determined using the method of determining a set of meta-features according to any one of the embodiments described herein, e.g. the method 200. Information pertaining to the set of relevant parameters 112 and to the set of meta-features $f_1, \ldots, f_L$ may for example be stored in the data storage 604. In some embodiments, the data storage 602 may also comprise instructions that cause the processing device 602 to execute a corresponding method. The data storage 602 may in particular store the instructions of the computer program product 500 described above or at least a part thereof.

In some examples, the system 600 may comprise additional components as illustrated in FIG. 6. The system 600 may for example comprise one or more test control samples 300A and/or one or more test samples 300B, wherein the test samples 300B are to be exposed to a test substance. Moreover, the system 600 may be configured to take the microscopic images of the test control sample 300A and of the test sample 300B. For this, the system 600 may be configured to control a sample preparation system 608, which may e.g.

comprise a pipetting robot configured to prepare the samples 300A, 300B in wells on one or more multi-well plates. The system 600 may further be configured to control a microscope 610, e.g. a high-throughput microscope that is configured to take microscopic images of a sample, preferably at multiple wavelengths. The sample preparation system 608 and the microscope 610 may be provided as independent units or may be part of the system 600 in some embodiments.

In the following, a few experimental results obtained with methods according to embodiments described herein are presented. For this data, the open-source software "CellProfiler" (Version 3.1.8, see A. E. Carpenter et al., *Genome Biol.,* 7(10):R100 (2006)) was used to extract parameter values of cell parameters from microscopic images. Methods of determining a set of meta-features and of studying an effect of a test substance on a test sample in accordance with embodiments described herein were implemented using the programming language "R" (Version 3.4.1), see www.r-project.org.

FIG. 7 shows microscopic images of a control samples (CTRL) and reference samples (PE, INS) and a determination of relevant parameters according to an exemplary embodiment of the invention. The control and reference samples comprise neonatal rat cardiomyocytes (NRCM) prepared on imaging optimized 96-well plates. To transfect the cells with green fluorescent protein-labelled nuclear factor of activated T cells (NFAT-GFP), the samples were incubated in a serum medium comprising eGFP-NFAT adenovirus. The cytoskeleton of the cells was stained by applying desmin antibodies. Nuclear DNA was stained using 4',6-Diamidin-2-phenylindol (DAPI). One of the control samples (PE) was exposed to a stimulus substance comprising phenylephrine, the other control sample (INS) was exposed to a stimulus substance comprising insulin. Subsequently, microscopic images of the samples were taken using three wavelength channels for separate imaging of the DAPI-stained nuclear DNA, the desmin-stained cytoskeleton and the GFP-labelled NFAT.

The parameter values of a set of cell parameters were extracted for each sample using CellProfiler. Subsequently, relevant parameters were identified as exemplified by the lower plot of FIG. 7. Here, the standardized score (z-value) of four exemplary parameters ("area", "perimeter", "eccentricity" and "NFAT score") is shown for the control sample (left), the insulin-treated reference sample (center) and the phenylephrine-treated reference sample (right). The corresponding p-values were calculated for each reference sample as a significance measure with "*" indicating a p-value below 0.001, "" a p-value below 0.01 and "NS" a p-value above 0.05. The "NFAT score" is an example of a secondary cell parameter. The "NFAT score" is calculated from the mean intensity in the GFP channel in the cytoplasm and in the nucleus and quantifies a translocation of eGFP-NFAT from the cytoplasm compartment into the nuclear compartment. As can be seen from FIG. 7, the selection of relevant parameters depends on the reference or stimulus substance to which the respective reference sample was exposed. In one example, only parameters with a p-value below 0.001 are selected as relevant parameters.

FIG. 8 shows a determination of a set of meta-features using phenylephrine as a stimulus substance for samples of NRCMs in accordance with an exemplary embodiment of the invention. FIG. 8A lists steps of the procedure together with the number of parameters/meta-features at the respective step. The set of cell parameters comprises a set of primary cell parameters extracted using CellProfiler and a set of secondary cell parameters including the NFAT score and a cell cycle state parameter. The total number of cell parameters is 1338. In this example, the reference sample comprises three individual samples, each of which is exposed to a different dose of phenylephrine. In FIG. 2B, the measured cell area is shown as an exemplary cell parameter for the control sample ("ctrl") and the individual samples of the reference sample ("PE low", "PE interm" and "PE high"). For comparing the parameter values of the control and reference samples, the dose dependency of the respective parameter is modeled using a mixed error-component model, in this example using the R packages "lme4" and "nlme". Each of the samples comprises a plurality of wells on multiple multi-well plates. The dose is used as a fixed variable assuming a linear dependency and a well identifier is used as a random variable.

The relevance of each parameter was assessed using the p-value of the mixed error-component model as a significance measure, wherein a threshold of $p<0.05$ was used for identifying relevant parameters. Subsequently, a validity measure for the parameters is determined by performing a statistical cross-validation. For this, the R function "R2CV" is used, which returns a cross-validated coefficient of determination $R^2CV$ of the statistical model for each parameter, wherein wells exposed to the same substance and concentration (i.e. the same concentration of phenylephrine in this example) were left out per plate for cross-validation. A threshold of $R^2CV>0.7$ was used for identifying relevant parameters as illustrated in FIG. 8C. In addition, a multiplicity adjustment based on the false discovery rate was performed. This resulted in a total of 112 relevant parameters.

The clusters of correlated parameters were identified from the set of relevant parameters by performing a hierarchical cluster analysis using Ward's minimum variance method, see FIG. 8E. For this, the R function "ward.D2" was used with the Euclidean distance between parameters as a similarity metric. The intra-cluster variability is quantified by averaging the mean absolute deviation of the parameters within each cluster over all clusters. A cutoff for the intra-cluster variability is used to determine the number of cluster as illustrated in FIG. 8D. In the example of FIG. 8, this yielded 38 clusters for the phenylephrine-treated reference sample.

For each cluster, a meta-feature was defined as the median of the relevant parameters contained in the respective cluster. Median feature values were calculated for the control sample and the individual samples of the reference sample and are illustrated as radar charts in FIG. 8F. Alternatively, the meta-feature could e.g. be defined as the mean of the relevant parameters contained in the respective feature.

The same procedure was repeated using different reference substances to determine substance-specific sets of meta-features. The corresponding numbers of parameters at certain steps of the procedure are shown in FIG. 8G, where "PE" indicates phenylephrine, "A", adrenaline, "NA" noradrenaline, "ISO" isoproterenol, "INS" insulin, "ET" endothelin, and "AT" Angiotensin. Each of these reference substances is a hypertrophy inducing substance and a potential mediator for cardiovascular conditions such as hypertrophic cardiomyopathy, amyloidosis and aortic stenosis.

FIG. 9 shows the results of a study of the effect of a plurality of hypertrophy inhibiting substances on test samples of NRCMs using a method according to an exemplary embodiment of the invention. In this example, meta-features were determined by comparing a reference sample exposed to phenylephrine to a control sample using the procedure illustrated in FIG. 8. Subsequently, these meta-features were used to assess the effect of a variety of hypertrophy inhibiting substances in different concentrations on phenylephrine-treated test samples. Mean feature values were calculated for the test samples and two test control samples, one of which was only exposed to phenylephrine (PE), whereas the other test control sample ("Ctrl") was neither exposed to PE nor to a test substance. The results are illustrated as radar plots in the left plot of FIG. 9. Here, "PI3K" denotes phosphoinositide 3-kinase, "ERK" extracellular signal-regulated kinase, "GSK" glycogen synthase kinase 3, "FAK" focal adhesion kinase/PTK2 protein tyrosine kinase 2, and "AKT" protein kinase B. Concentration of the test substances increases from left to right, wherein the leftmost row depicts the results for the PE-treated test control sample that was not exposed to any of the test substances. Significance of the absolute differences of the feature values compared to the PE-treated test control sample was quantified by calculating a p-value using a linear mixed effects model. The results are shown in the right plot of FIG. 9. In the left plot, "*" indicates a p-value below 0.05, "" below 0.01, and "*" below 0.001. This illustrates the potential of the invention for high-throughput screening of candidate substances to be tested as a potential inhibitor of a medical condition.

FIG. 10 shows the results of a study of the effect of blood plasma from patients with aortic stenosis on test samples of NRCMs using a method in accordance with an exemplary embodiment of the invention. For this, blood plasma of patients with aortic stenosis prior to (AS) and within one week after transfemoral valve replacement (TAVR) was used. The former was used as a reference substance to determine a set of relevant parameters and a set of meta-features (FIG. 10A, 10C). Feature values of the meta-features were determined for test samples exposed to blood plasma of patients with aortic stenosis prior to (AS) and within one week after transfemoral valve replacement (TAVR) as a test substance and compared to the respective feature values of a control test sample exposed to blood plasma of healthy patients (FIG. 10D). The results indicate partial reversibility of certain meta-features by TAVR. Furthermore, relevant parameters for TAVR-exposed samples were determined and compared to relevant parameters of AS-exposed samples as well as those of samples exposed to the hypertrophy inducing substances of FIG. 8G. Varying degrees of overlap between the sets of relevant parameters and partial reversibility of relevant parameters by TAVR were observed (see FIG. 10D). These results illustrate how the invention can be used to analyze the effect of a patient's blood plasma on a test sample, in particular to assess the progress of a treatment against a medical condition, in this examples transfemoral valve replacement for patients with aortic stenosis.

FIG. 11 depicts the results of a study of human induced pluripotent stem cell derived cardiomyocytes (hiPSC-CMs) using a method according to an exemplary embodiment of the invention. hiPSC-CMs are typically highly heterogeneous in their appearance and it is thus challenging to extract meaningful information from morphological cell parameters. In this study, hiPSC-CMs with the mutation R943x of the myosin binding protein C3 (MYBPC3) were analyzed. This mutation is known to induce hypertrophic cardiomyopathy without an impact on the cell size. A control sample comprising healthy wildtype hiPSC-CMs (wt) was used and compared to reference samples comprising homozygous (hom), non-induced heterozygous (het), or induced heterozygous (het ind) mutated cells. FIG. 11A illustrates the determination of a set of meta-features and FIG. 11B contains representative images of the respective samples. FIG. 11C shows parameter values for the z-transformed cell area of the cells in the samples, which indicates no significant difference between heterozygous, homozygous, and wildtype cells. FIG. 11D shows the feature values of the set of meta-features for the samples. Homozygous mutated cells exhibit a prominent morphological pattern compared to wildtype cells, which is attenuated in heterozygous cells. One of the relevant parameters is the Haralick correlation feature associated with sarcomere organization. FIG. 11E illustrates the hierarchical cluster analysis used for determining the meta-features.

FIGS. 12*a* and 12*b* illustrate the determination of secondary cell parameters and the identification of subsets of cells or cell populations in a sample using methods according to exemplary embodiments of the invention.

FIG. 12*a* shows a cell-cycle analysis for determining the cell cycle state of the cells in a sample. For this, a functional cell parameter characterizing the density of DNA in the nucleus is used, wherein the respective parameter value is given by the integrated intensity in the nucleus in a microscopic image of stained nuclear DNA. The right plot shows a histogram of the parameter values for the cells in the sample and the left plot shows the corresponding density calculated using the density function in R. The resulting distribution exhibits a multi-modal structure, which can be associated with three different cell cycle states: dead (low intensity), G1 phase (intermediate intensity), and G2/S phases (high intensity). From the distribution, thresholds are determined for assigning each cell to one of the three categories. Here, the solid lines depict the median of the respective threshold and dashed and dotted lines depict the 10% and 90% quantiles, respectively, each of which may be used for assigning the categories. The cell cycle state is an example of a categorization parameter, which may be added to the set of cell parameters. In some embodiments, only cells with certain cell cycle states may be selected as a subset for further analysis, e.g. only cells that are not dead.

FIG. 12*b* shows the identification of attached, vital cardiomyocytes in a sample. For this, a secondary parameter is determined that quantifies the ratio of the cross-sectional areas of the cells and their nucleus. A small ratio may indicate that the respective cell is not intact and/or detached from the substrate. The upper plot shows a histogram of the parameter values of this secondary parameter for the cells in the sample, the center plots shows the corresponding density calculated using the density function in R with different bandwidths (left: 0.1, right: "auto"). The bottom plots show the selection of attached, vital cardiomyocytes using different cutoffs determined based on the first minimum to the left of the maximum of the distribution (left: median, right: 90% quantile). In some embodiments, only attached and vital cells may be taken into account for further analysis, i.e. cells with a ratio of cell area to nucleus area above the threshold.

In the following, preferred embodiments of the above-described method of studying an effect of a test substance on a test sample of biological cells are described:

In an experimental part, any cardiac cells can be used. Preferably, these cardiac cells are combined with blood plasma, blood serum and/or other pharmacological substances.

Image acquisition can be performed with a microscope. Preferably, this is performed at the end of the experiment. In other embodiments, the image acquisition is performed during the course of the experiment to analyze the cell response over time (video, live cell imaging).

Parameter extraction can be performed using freeware software such as CellProfiler.

Embodiments of the presented pattern recognition approach can have the following advantages: It copes with very heterogeneous cells, but can also be applied to homogeneous cells. It can perform pattern recognition (in particular recognition of patterns of the meta-features) for any cardiac disease. Embodiments can achieve a high reproducibility. Special feature of single cell analysis allows subpopulation analysis, thus also allowing cell type analysis. The detected patterns can have different clinical relevance, thus allowing diagnosis, prognosis, grading, assessing severity, and/or individualized therapy options.

In some embodiments, cell morphology analysis (parameter evaluation) integrates e.g. gene activity and protein localization into the parameter evaluation by using reporters for: e.g. fluorescent labelling of specific proteins. Via imaging, fluorescence can be used as a surrogate for processes at the genetic, epigenetic, transcriptional, post-transcriptional, and protein levels and can be incorporated into the presented method. In a preferred embodiment, the protein NFAT is labelled with eGFP because the protein NFAT plays an important role in growth processes and experiments have shown that localization of NFAT is a valuable parameter.

In order to perform time series analysis, imaging of cells can happen multiple times with live cell fluorescent dyes. This allows visualizing the dynamics of cell morphological changes over time. Experiments have shown that certain dynamics leads to a characteristic set of meta-features associated with certain diagnoses, prognoses, and/or individualized therapy.

Preferably, the plurality of images is acquired at different time points.

The presented methods can diagnose the presence of a cardiovascular disease and not only the risk of developing a cardiovascular disease in the future (risk of developing a disease, risk profile). Furthermore, the presented methods can derive prognosis from the diagnosis and could characterize therapy correlates (interventional: aortic stenosis before and after TAVR, drug: stimulus+inhibitor).

In another preferred aspect the presented method can be used to determine most effective therapy. Therefore, predication of individual therapy success (drug or interventional therapy) by the following experiment: cell+blood+one or more test substances compared with at least one positive control or negative control. (e.g. Positive control: cell+blood+test substance, negative control: cell+blood from healthy individual or cell without blood).

In particular, the following practical procedure can be performed: The patient is tested for several possible drug therapies (test substances) before starting the therapy, then the presented method is performed and the most effective therapy is selected. (Inhibitor Experiment)

In another preferred aspect, the presented method can be used for monitoring the treatment: The patient comes in regular intervals and the presented method is performed with his or her blood. The dosage of the drug can be adjusted based on the presented methods, or it can be recognized that the patient benefits from another combination of drugs compared to monotherapy, or it can be recognized that another therapy is more effective.

In an other aspect, the presented method can be used to predict therapy side effects: Herein a similar process as above can be used.

The presented method can be used for different patient populations, which can be selected as follows: Healthy patients, patients with suspected cardiovascular disease (Data heart healthy vs heart diseased), patients with diagnosed cardiovascular disease (preferably amyloidosis, aortic stenosis, dilated cardiomyopathy, ischemic cardiomyopathy, hypertrophic cardiomyopathy, reanimated patients).

The presented method is applicable to heterogeneous cells. In addition to neonatal mammalian cardiomyocytes, stem cell-derived cardiomyocytes, which have high heterogeneity, the presented methods can also be applied to whole heart lysates. Cardiac cell lines, muscle cell lines, vascular cell lines (endothelial cells), cells from neonatal and adult mammalian hearts, human cardiomyocytes, human and mammalian cardiomyocytes from tissue sections, histological preparations can be used. Furthermore, not only cardiovascular cells, but also other cells related to other diseases can be used.

Single cell analyses: Since cardiac cells are often very heterogeneous, single cell analyses are particularly useful to gain additional insights with respect to cell subpopulations (Diagnostic/prognostic/therapeutic subpopulation). A subpopulation is defined as one or more single cells with some morphological similarity to each other.

Experiments have shown that sometimes it is not the totality of cells that indicates a disease, but the disease can be identified by the presence or amount of a certain subpopulation of cells. Applications that were shown on the averaged morphology of cells can also be performed at the single cell level.

With the presented methods it is possible to calculate the individual composition of cardiac cells from e.g. whole heart lysates and look at the morphology per cell type separately.

Diagnosis/prognosis/individual therapy can be based on the composition of cell types or composition of individual cells. Sometimes not the totality of cells indicates a disease, but the disease can be detected by a typical composition at subpopulations or cell types (Diagnosis/Prediction/Indiv. Therapy). The presented applications on the averaged morphology of the cells can also be performed per cell type.

The presented method can work with blood plasma and blood serum: Experiments have shown that the biologically very similarly composed blood serum is also suitable for use with the presented method. Preferably, concentrations of the blood serum between 1% and 20% are used.

Lasso regressions with cross-validation of data preprocessed with cmoRe (filtering and median aggregation per well) can be trained to classify the samples. In particular, this can be used for an amyloidosis and heart failure diagnosis classifier.

For Transcatheter aortic valve replacement, a random forest can be used for classification.

Reanimation: An analysis of similarity of temporal changes can be performed (delta feature matrix: time 0 and 24 h after admission), as well as hierarchical clustering of the correlation matrix (Kendall correlation coefficient).

Application of an adenovirus construct allows the quantification and intracellular localisation of the NFAT (Nuclear Factor of Activated Tcells) protein. NFAT was chosen as an example here because this protein concentrates in the cell nucleus (localisation) in certain forms of cardiac cell growth (activation of the calcineurin-NFAT signalling pathway). Using image data, one can thus indirectly obtain information on protein quantities and protein localisation and recognise the switching on/off of known signalling pathways.

The presented methods can be used for Diagnosis classification and prognosis stratification of patients, as well as assessing severity of a disease:

The "HeartSens" component allows prediction/classification of healthy vs. diseased hearts (heart failure, amyloidosis/aortic stenosis, DCM, ICMP, hypertensive heart disease, hypertrophic cardiomyopathy).

A collective of 16 heart-healthy patients and 93 patients with heart disease (amyloidosis, aortic stenosis, dilated cardiomyopathy (DCM), ischaemic cardiomyopathy (ICMP), hypertensive heart disease, hypertrophic cardiomyopathy (most common heart diseases)) was used.

FIG. 13C shows a breakdown of patient numbers in training set and test set.

We extracted morphological data per cell (CellProfiler and preprocessing steps as described) and aggregated them per well (median) based on images obtained with our assay (concentration 1% blood plasma in medium, no PE stimulation). This results in a specific constellation of morphological features per cell as well as per well, which are used for further analysis.

The data was divided into a training set (70% of the patients; 11 healthy heart patients and 49 heart patients) and a test set (30% of the patients). The training set was used to develop HeartSens and the test set was used in a second step only to evaluate the performance of HeartSens.

A logistic regression to distinguish between healthy and diseased hearts was trained using the training set with the modelBuildR package (HeartSens), see Knoll M, Furkel J, Debus J, Abdollahi A. modelBuildR: an R package for model building and feature selection with erroneous classifications. PeerJ. 2021 Feb. 9; 9:e10849. doi: 10.7717/peerj.10849. PMID: 33614290; PMCID: PMC7879945.

We investigated performance using ROC analysis (AUC=87%, 95% confidence interval: 0.75-1, p. FIG. 13A) on the test set data. Overall, we found good sensitivity and specificity in discriminating between healthy and ill heart patients in our collective. The test set data were not used to train HeartSens and represented unknown data for HeartSens.

To classify a new patient, the assay is performed as usual and the morphological data aggregated per well (median) are entered into HeartSens (logistic model). HeartSens predicts the probability of the presence of heart disease.

FIG. 13B shows the predictive score values of HeartSens, which represent the probability that a heart disease is present. Depending on the intended application (screening e.g. very high sensitivity, or for validation e.g. very high specificity) the cut-off can be adjusted according to the ROC analysis FIG. 13A.

The HeartProfiler Component Presents a Diagnosis Classifier for Heart Disease (Heart Failure)

Heart diseases include a large number of different diagnoses. The aim of HeartProfiler is to differentiate between them. This can be used for the new diagnosis of patients (e.g. at the first contact in the clinic/practice or in unclear cases to avoid invasive diagnostics) or to check an already existing cardiac diagnosis (misdiagnosis) or to detect the parallel presence of two cardiac diseases.

Patient population: 16 heart healthy patients and 93 heart diseased patients (amyloidosis, aortic stenosis, DCM, ICMP, hypertensive heart disease, hypertrophic cardiomyopathy (most common heart diseases)).

NRVCMAssayData: NRVCMs with 1.25% patient serum, 5% patient serum, each with and without simultaneous growth stimulation with phenylephrine. 4 wells per condition.

Analogous to HeartSens, we divided the collective of 16 heart-healthy patients and 93 heart patients into a training set and a test set. The training set was used to develop HeartProfiler and the test set was used in a second step only to evaluate the performance of HeartProfiler.

HeartProfiler comprises different logistic models (pairwise comparisons, logistic regression, lasso), each of which calculates the probability of the presence of a specific heart disease.

Figure 14:
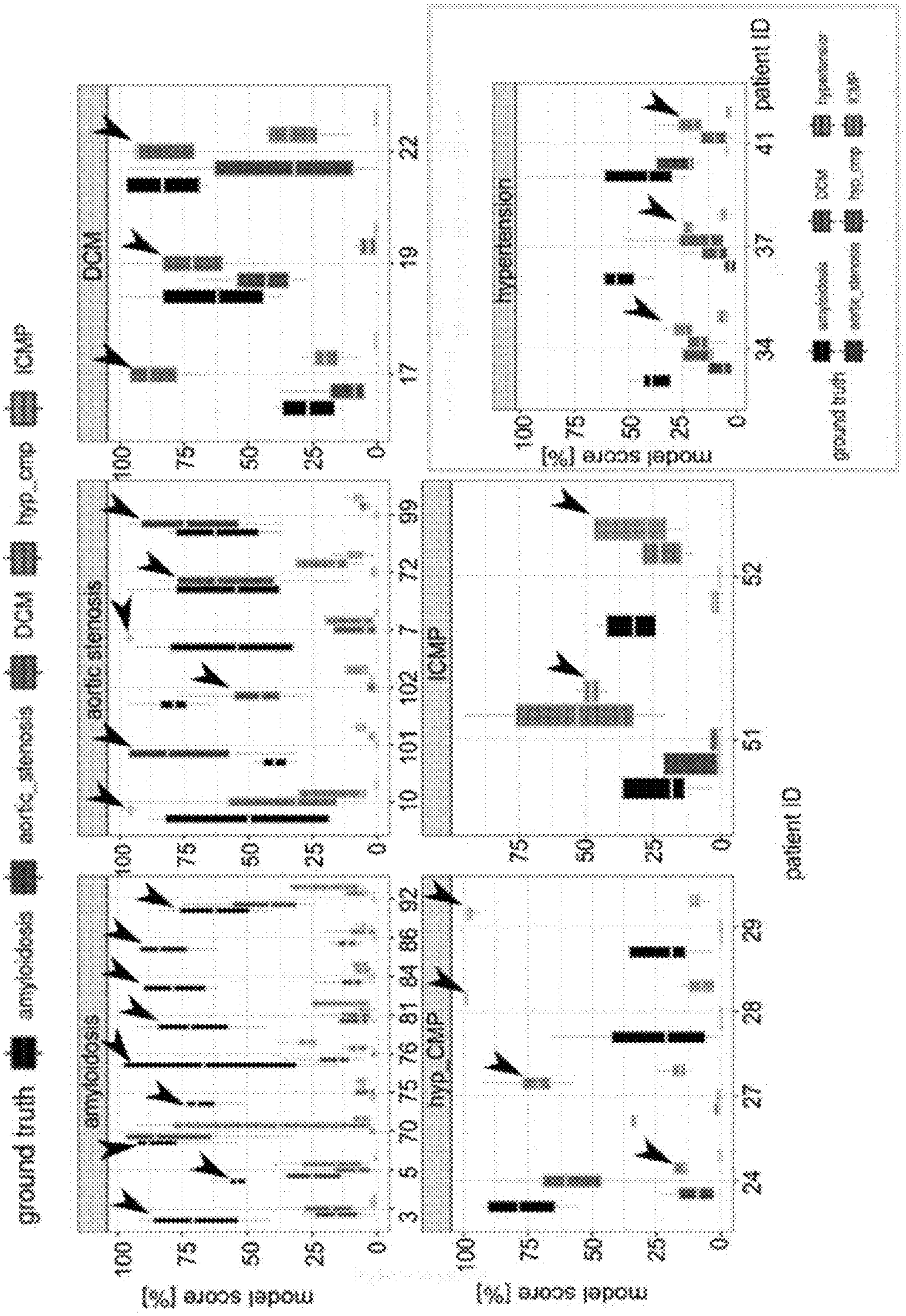

For each NRVCM assay condition, a separate model is trained that predicts the probability of heart disease per well. For each assay condition, the maximum score achieved by the 4 wells is stored. In the next step, the maximum score values of the 4 assay conditions are summarised, which are used for clinical classification (FIG. 14: Median+/−Quantiles). Thus HeartProfiler outputs one score value per patient (shown here as median). In a second step, we evaluated the performance of HeartProfiler on a test set that was still unknown to HeartProfiler. In doing so, we tested the probabilities of the presence of the heart diseases per patient. In FIG. 14, the patients (numbers) are shown on the x-axis and grouped according to their underlying disease (subheadings). The medians and quantiles of the probability values (score values) of the presence of heart disease calculated by HeartProfiler are shown. These can be sorted by score value and thus result in a most probable diagnosis (1st rank of the score value sorting, marked with arrowheads in FIG. 14).

In patient 70, for example, this would be: 1. amyloidosis, 2. aortic stenosis, 3. hypertrophic cardiomyopathy, 4. ICMP, 5. DCM.

Correct classifications of the most likely diagnosis calculated by HeartProfiler for the following heart conditions: Amyloidosis 9/9, Aortic stenosis 5/6, DCM 3/3, Hypertrophy Cardiomyopathy 3/4, ICMP 0/2.

Overall, the experiments have shown a very good performance of the correct classification. For aortic stenosis, the one misclassified patient was assigned to aortic stenosis with at least second highest probability, likewise for the two misclassifications for ICMP. ICMP is a disease based on increased calcification of the arteries of the heart. As this is not unique to ICMP patients, but also occurs to a lesser extent in everyone as they age, components of ICMP may also be found in other heart diseases, which may naturally affect the sensitivity of ICMP classification. In the case of hypertrophic cardiomyopathy, a misclassification occurs in which hypertrophic cardiomyopathy is only rated in 3rd place by HeartProfiler.

Review of Existing Diagnoses

HeartProfiler can also be used to check an initial diagnosis (possibly a misdiagnosis) or to detect a parallel, previously undetected second cardiac disease. This is relevant e.g. for aortic stenosis patients who often have undiagnosed amyloidosis at the same time and who may have additional therapeutic options.

FIG. 14 also shows a tendency for aortic stenosis patients to also have high amyloidosis scores.

Forecast: The diagnosis is accompanied by a certain prognosis for the respective heart diseases in question, so that a prognosis can be derived from the HeartProfiler profile and thus a risk stratification of the patients can be carried out.

Deeper analysis of individual disease entities: Amyloidosis is a rare disease and is often diagnosed very late or completely overlooked. The clinical course including prognosis (affected organs, severity of the course of the disease and time of onset in the case of hereditary amyloidoses) is also subject to very great uncertainty at the present time. The very limited diagnosis and prognosis prediction using state-of-the-art methods and the high sample availability result in a great potential for this disease.

In addition, experimental data on the diagnosis of amyloidosis using our technique has been evaluated. Two different analysis approaches for this can be used:

AmyloidosisProfiler1

The score calculated with the presented method including all morphological parameters shows gradations according to the diagnostic subclasses of amyloidosis patients (FIG. 15A). The calculation of the scores is analogous to HeartProfiler (but here with 5% and 20% blood plasma+/−PE) based on a training set that includes AL amyloidoses, wt TTR amyloidoses, aTTR FAC amyloidoses, aTTR FAP amyloidoses and healthy hearts.

Correct classification of amyloidosis subtypes on the test set, shown in FIG. 15A, is consistently seen.

AmyloidosisProfiler2

The calculation of the scores is analogous to HeartProfiler (but here with 5% and 20% blood plasma+/−PE) based on a training set containing only wtTTR amyloidosis heart healthy individuals characterised by clear cardiac involvement, as can be seen in FIG. 15B.

Amyloidosis Subpopulation

Figure 15:
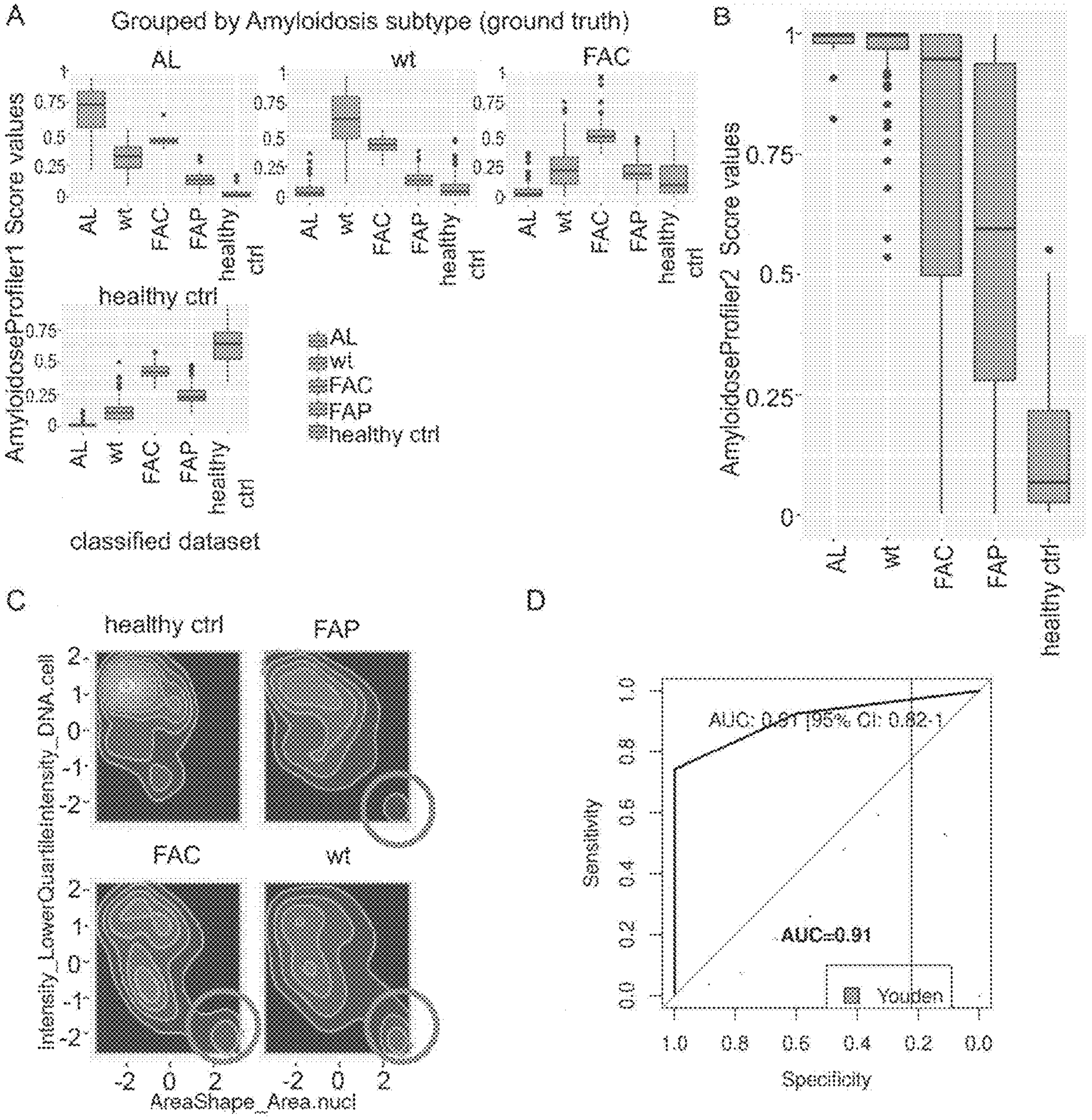
Figure 16:
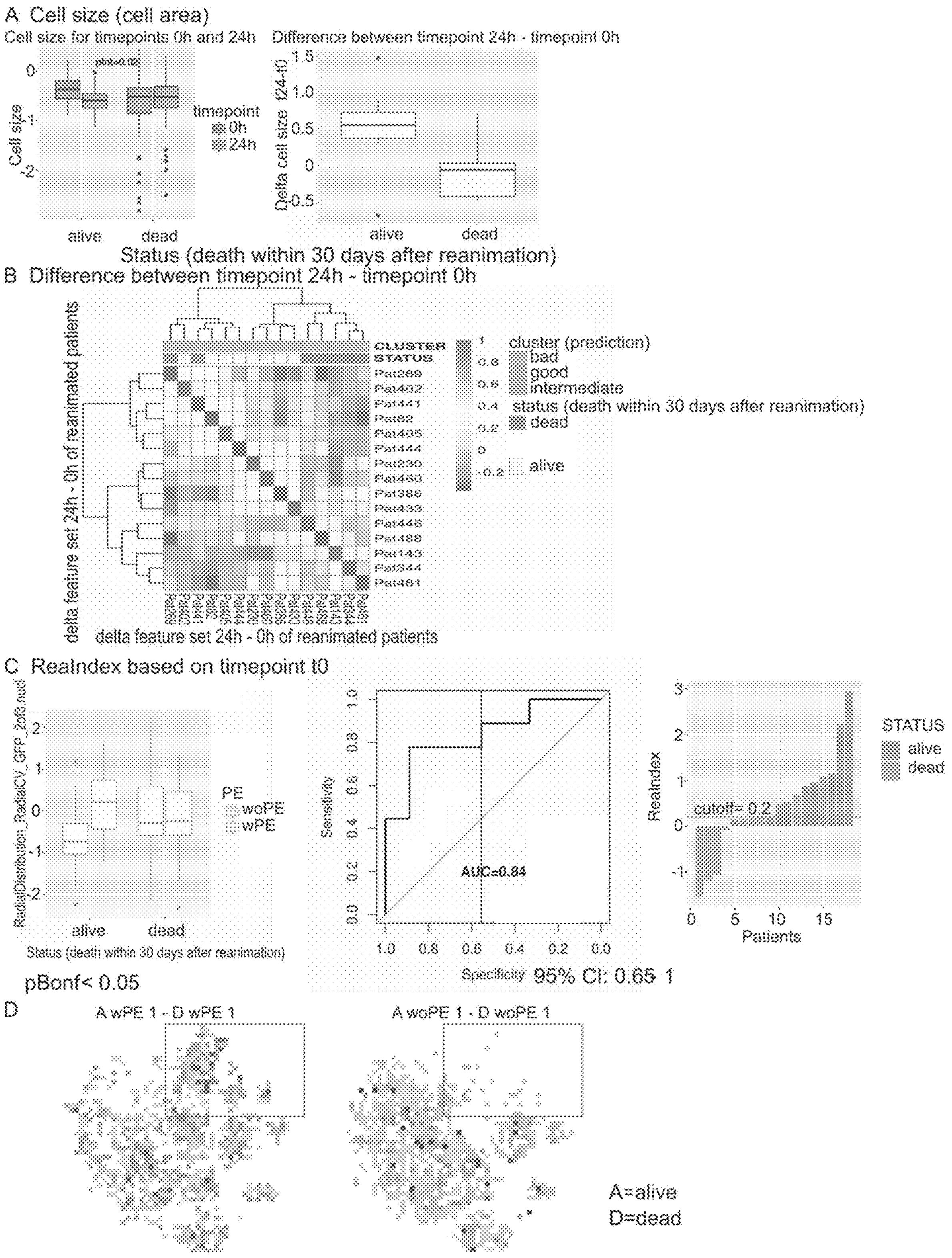

On the basis of two features (see FIG. 15 C), we were able to discover a subpopulation associated with the cardiac involvement of the patients (subpopulation circled in red in FIG. 15 C, Ctrl and FAP have no cardiac involvement, wt and FAC have cardiac involvement). In Ctrl the subpopulation does not exist at all, in FAP only very weakly. In diseases with cardiac involvement FAC and wt amyloidosis this subpopulation is very pronounced.

Even with transthyretin mutations initially classified as FAP, i.e. rather polyneuropathic, cardiac involvement sometimes becomes apparent in the course of the disease. Therefore, it is not implausible that in some patients the subpopulation indicating cardiac involvement can also be detected or is present at an attenuated level.

In FIG. 15 D, the classification of patients is evaluated based on the presence of the subpopulation (at least 10%) for cardiac involvement yes/no.

From the experiments it can be seen that aortic stenosis patients also show a specific pattern.

Morphological phenotype (specific constellation of morphological features) of aortic stenosis. This phenotype reverts to the phenotype of healthy controls after interventional therapy (transcatheter aortic valve replacement (TAVR)).

In a reclassification, image data are mostly correctly assigned to the categories “aortic stenosis before TAVR” and “aortic stenosis after TAVR”.

Hypertrophic Cardiomyopathy

The performed experiments show that with the help of the presented method, a cardiomyocyte genetically altered in the direction of hypertrophic cardiomyopathy can be detected in comparison to a genetically healthy cardiomyocyte.

Reanimated patients: The extreme case of cardiac insufficiency is shock, e.g. of cardiogenic or septic origin, which leads to cardiovascular arrest and death if resuscitation is not performed.

After resuscitation, it is still unclear what the patient’s prognosis is. Some patients survive a cardiovascular arrest requiring resuscitation without long-term damage, i.e. with good cardiac pumping strength and without neurological damage. Other patients, however, develop severe heart failure or brain damage due to oxygen deprivation (hypoxic brain damage), which can lead to death within 30 days of resuscitation, or they die within 30 days of resuscitation for other reasons (e.g. aspiration pneumonia, multiple organ failure). Death within 30 days of resuscitation has become the accepted endpoint in the literature.

Blood samples were taken from 20 resuscitated patients at the time of admission (0 h) and, if possible, in the further course (24 h, 48 h, 72 h), the serum was processed and the samples were stored at −80° C. The blood samples were taken at the time of admission (0 h). For 5 patients, there were only blood samples from 0 h, as they subsequently died. Together with 10 heart-healthy controls, we applied the patient sera according to our experimental method. 1% and 10% blood serum, each with and without simultaneous stimulation with PE were applied to the NRVCMs.

FIG. 16A shows the cell size at 0 h and 24 h after resuscitation: In the group of patients who die within the first 30 days after resuscitation, there is no significant difference in cell size between the time points 0 h and 24 h. In contrast, the other patients (alive) showed a decrease in cell size compared to time point 0 h.

Discussion: Since the body’s own catecholamines such as adrenaline etc. are released during resuscitation and catecholamines are applied medicinally during resuscitation and are known to initiate cell growth of cardiomyocytes, it is plausible that at time 0 h the blood plasma causes hypertrophy of the NRVCMs in our assay.

ReaCluster: In FIG. 16B, the change in all morphological features between time 0 h and 24 h is quantified. In the next step, these changes between patients are plotted in a correlation matrix (blue means that the changes are opposite. Red means that the patients have similar feature dynamics). Using hierarchical clustering, morphologically similar patient samples are grouped together (clusters). One cluster is associated with a poor prognosis (100% dead), one cluster with a good prognosis (100% alive) and a third cluster is mixed (intermediate).

ReaIndex: FIG. 16C: In order to enable a prognosis assessment already at the time t=0 h, i.e. directly after admission of the patient, we have developed the ReaIndex, which takes the change of a NFAT-GFP feature with and without PE stimulation (blood serum concentration 1%) as a basis. The corresponding ROC analysis shows an AUC of 84% (confidence interval 65%-100%). In C on the right, the patients of our collective were reclassified with a cutoff=0.2 (optimal cutoff according to Youden Index) (below the cutoff line as dead and above the cutoff line as alive). The ground truth (real status) is shown in colour. Only 3 patients were misclassified.

A new patient could be prognostically stratified with blood samples from time t=0 h using the ReaIndex. If blood samples are available for 0 h and 14 h, the patient can be subjected to hierarchical clustering together with the existing collective to determine their group membership and thus provide a rough prognosis estimate (ReaCluster).

ReaSingleCell: At the single cell level, we found a subpopulation that differs between the dead and alive groups under PE stimulation. (time point 24 h, conc 1% blood serum). The amount of cells in the PE-inducible subpopulation can be used as another parameter to predict 30-day mortality. (FIG. 16D left: Difference in cell density distributions (tSNE) between alive and dead under PE stimulation, right without PE stimulation. Differences in density are only seen under PE stimulation in the area of the red box.

HeartSubpopulation: Identification of pathognomonic cell populations that are specific to a disease entity and might hint to potential target cells for therapies It could be that certain heart diseases cause specific states in cardiomyocytes that are characteristic for this heart disease (diagnostically relevant) and/or that these specific cardiomyocytes even contribute causally to the development or maintenance of the heart disease. At the level of aggregate cell analysis, disease-specific cell subpopulations might not be detected, but at the level of the individual cell they are. Therefore, we searched for disease-specific or substance-specific cell populations in the amyloidosis and resuscitated patient collectives.

In amyloidosis, on well aggregated data we could already detect a subpopulation associated with cardiac involvement of patients (Ctrl and FAP have no cardiac involvement, wt and FAC have cardiac involvement).

Figure 17A:
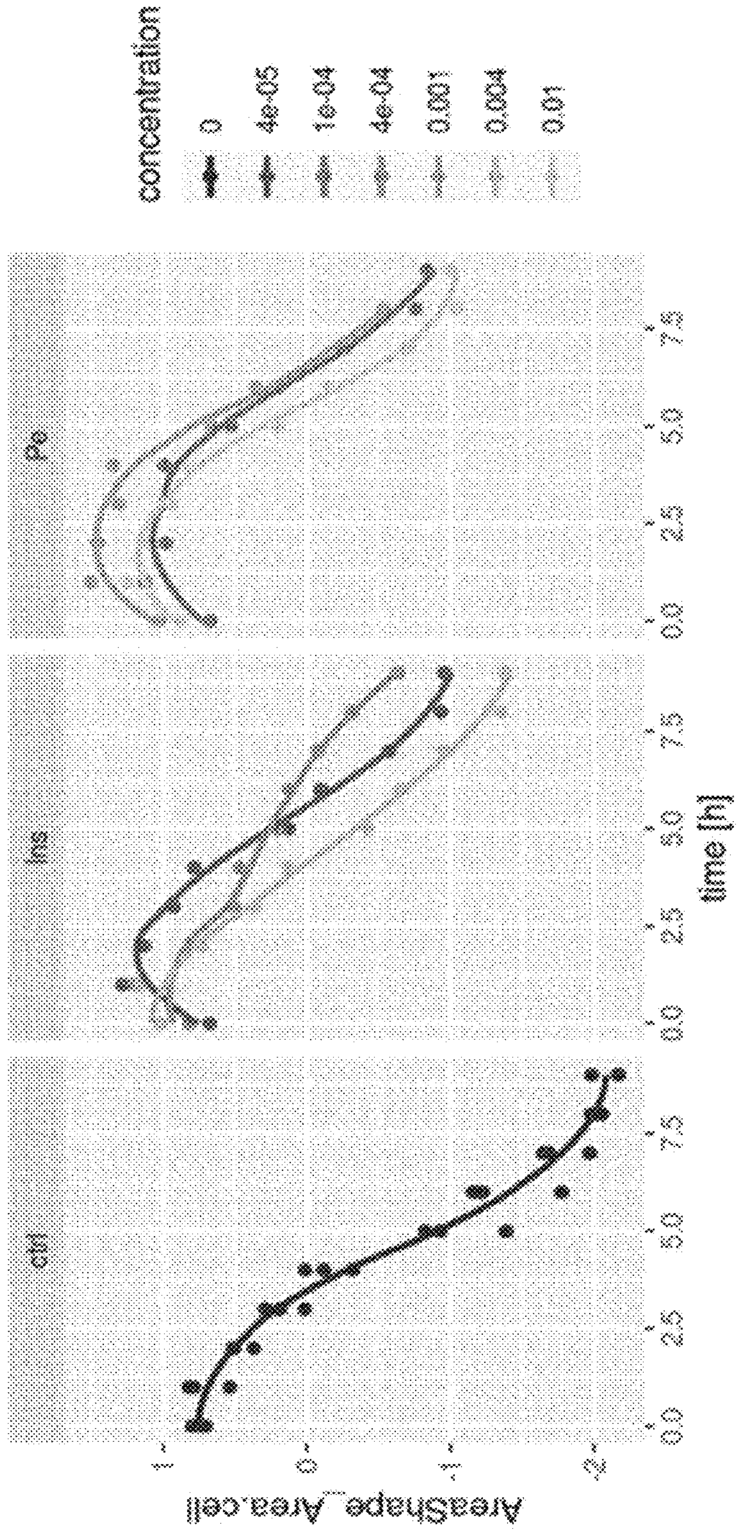

FIG. 17A shows changes in cell areas within a 9 h window (live cell imaging), where differences following stimulation can be observed after 9 h (Ctrl vs PE/Ins), but also the early dynamics (<2.5 h) allow a differentiation of substance (steep increase for PE, less steep increase for Ins, no increase for ctrl).

Figure 17B:
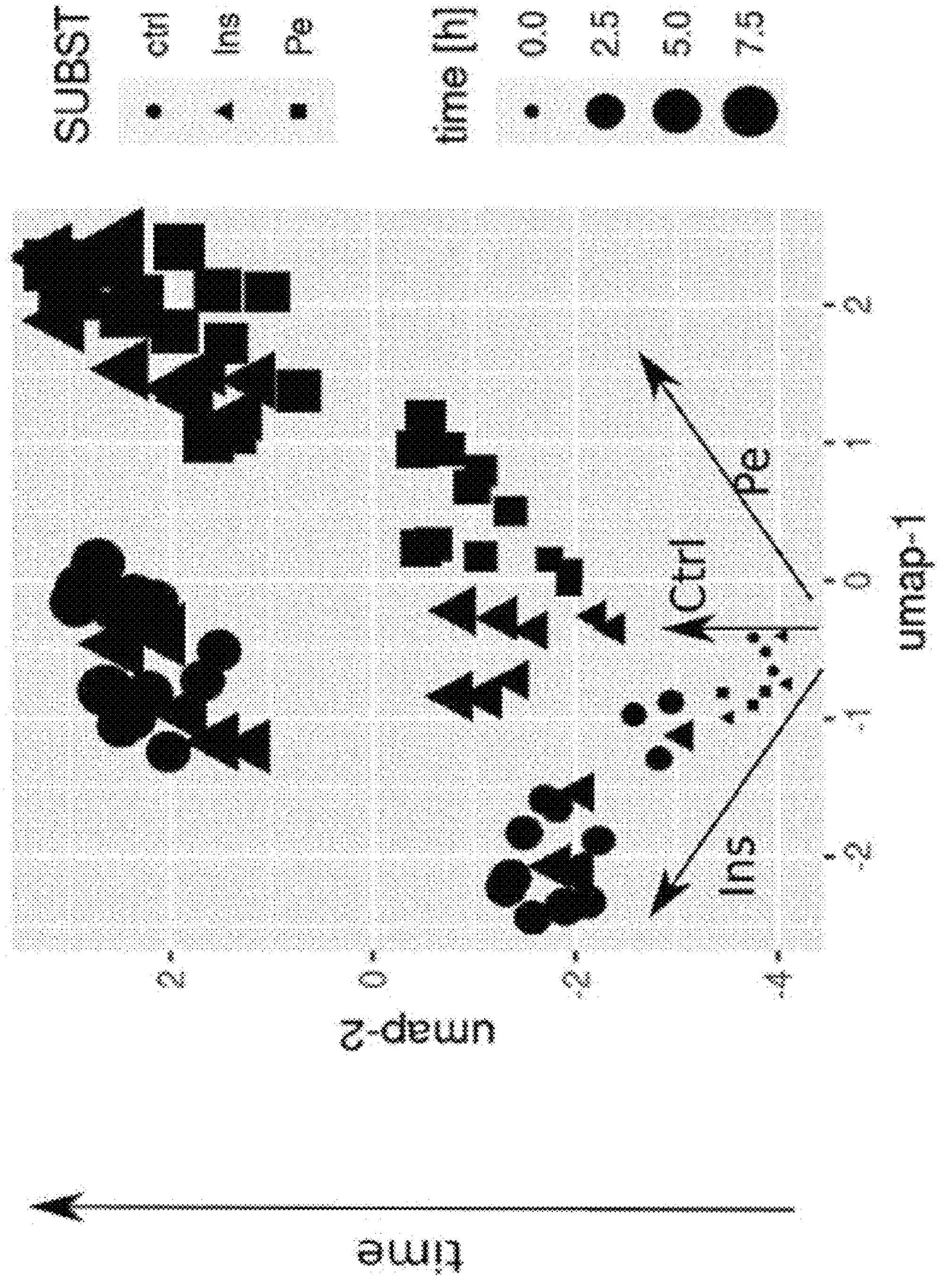

FIG. 17B shows a umap representation of morphological features of longitudinal livecell data. Starting from a similar morphological phenotye (timepoint 0), main cell developmental trajectories can be differentiated The embodiments of the present invention disclosed herein only constitute specific examples for illustration purposes. The present invention can be implemented in various ways and with many modifications without altering the underlying basic properties. Therefore, the present invention is only defined by the claims as stated below.

The present invention also provides the following examples:

Example 1: A method of determining a set of meta-features for comparing samples of biological cells, the method comprising:

- receiving parameter values of a set of cell parameters for each of a plurality of cells in a control sample and for each of a plurality of cells in a reference sample;
- identifying a set of relevant parameters from the set of cell parameters by comparing the parameter values from the control sample and the parameter values from the reference sample for at least one of the cell parameters;
- identifying clusters of correlated parameters within the set of relevant parameters based on correlations between the parameter values of the relevant parameters; and
- defining a meta-feature for at least one of the clusters as a mathematical function of the parameters of the respective cluster.

Example 2: The method of example 1, wherein the cells comprise heart cells.

Example 3: The method of examples 1 or 2, wherein the reference sample was exposed to a reference substance having a functional, physiological, pathological, and/or morphological effect on cells in the reference sample, wherein preferably the reference substance comprises a stimulus substance being a mediator involved in one or more cardiovascular conditions, in particular wherein:

- the reference sample comprises a plurality of individual samples, each of which was exposed to a different dose of the reference substance; and
- comparing the parameter values from the control sample and the parameter values from the reference sample comprises modelling a dose dependency of an effect of the reference substance on the respective parameter using a statistical model, in particular a mixed error-component model.

Example 4: The method of any one of the preceding examples, wherein:

- comparing the parameter values from the control sample and the parameter values from the reference sample comprises determining a significance measure for at least one of the cell parameters, wherein the significance measure characterizes a statistical significance of a difference or equivalence between the respective parameter values in the control sample and in the reference sample; and
- relevant parameters are identified based on the significance measure of the at least one cell parameter, in particular wherein:

- comparing the parameter values from the control sample and the parameter values from the reference sample further comprises determining a validity measure for the at least one cell parameter by performing a statistical cross-validation of a statistical model for the respective cell parameter; and
- relevant parameters are identified based on the significance measure and the validity measure of the at least one cell parameter.

Example 5: The method of any one of the preceding examples, wherein the clusters of correlated parameters are identified by performing a hierarchical cluster analysis, a centroid-based clustering, a density-based clustering and/or a neuronal network-based clustering.

Example 6: The method of any one of the preceding examples, wherein the set of cell parameters comprises one or more of:

- at least one geometrical cell parameter characterizing a size and/or shape of the respective cell or of a part thereof;
- at least one structural parameter characterizing a structure and/or topography of the respective cell or of a part thereof;
- at least one functional parameter characterizing a concentration and/or a distribution of a biomolecule or of a biochemical substance in the respective cell or in a part thereof;
- at least one proximity parameter associated with one or more cells in the vicinity of the respective cell; and
- at least one machine vision parameter extracted from an image of the respective cell or of a part thereof using a neural network.

Example 7: The method of any one of the preceding examples, further comprising:

- determining a parameter value of a secondary cell parameter for each of the plurality cells in the control sample and for each of the plurality of cells in the reference sample based on the parameter values of the set of cell parameters for the respective cell; and
- adding the secondary cell parameter to the set of cell parameters,
- wherein the secondary parameter preferably characterizes a cell type or a state of the cell.

Example 8: The method of any one of the preceding examples, further comprising:

- selecting a subset of cells from the plurality of cells in the control sample and/or in the reference sample based on the parameter values, wherein selecting the subset of cells preferably comprises identifying apoptotic cells, non-intact cells and/or cells not matching a predetermined cell type based on the parameter values and excluding the respective cells from the selected subset; and/or identifying cell populations within the plurality of cells in the control sample and/or in the reference sample based on the parameter values and/or on values of the meta-features.

Example 9: The method of any one of the preceding examples, wherein receiving the parameter values for the control sample and/or for the reference sample comprises receiving one or more microscopic images of the respective sample, identifying individual cells in the one or more microscopic images and extracting the parameter values for each of the identified individual cells from the one or more microscopic images, in particular wherein receiving the one or more microscopic images comprises:

staining one or more parts of the cells in the control sample and/or in the reference sample and/or labelling one or more biomolecules or biochemical substances in the cells in the control sample and/or in the reference sample with an imaging marker; and taking the one or more microscopic images of the respective sample.

Example 10: A method of studying an effect of a test substance on a test sample of biological cells using a set of relevant parameters and a set of meta-features determined with a method according to any one of the preceding examples, the method comprising:

exposing the test sample to the test substance;

determining parameter values of the set of relevant parameters for each of a plurality of cells in the test sample; and determining feature values of the set of meta-features for the test sample, wherein each of the feature values is calculated from the parameter values of a cluster of correlated parameters from the set of relevant parameters that is associated with the respective meta-feature.

Example 11: The method of example 10, further comprising:

determining parameter values of the set of relevant parameters for each of a plurality of cells in a control test sample;

determining feature values of the set of meta-features from the parameter values of the set of relevant parameters for the control test sample; and comparing feature values of meta-features for the test sample and feature values of meta-features for the control test sample to assess the effect of the test substance.

Example 12: The method of example 10 or 11, wherein:

the reference sample for determining the set of meta-features was exposed to a stimulus substance, the stimulus substance being a mediator involved in one or more medical conditions, in particular in one or more cardiovascular conditions, wherein the stimulus substance preferably comprises a hypertrophy inducing substance, in particular at least one of phenylephrine, adrenaline, noradrenaline, isoproterenol, insulin, endothelin, and angiotensin, and/or wherein the test substance preferably comprises a candidate substance to be tested as a potential inhibitor of the medical condition; and/or the test substance comprises a sample of a patient, in particular a blood sample of the patient, preferably blood serum or blood plasma of the patient, wherein the method preferably further comprises diagnosing a medical condition, assessing a risk of developing the medical condition, and/or assessing a progress of a therapeutic treatment against the medical condition based on the feature values of the set of meta-features for the test sample, in particular wherein the medical condition is hypertrophic cardiomyopathy, amyloidosis and/or aortic stenosis.

Example 13: The method of any one of examples 10 to 12, wherein:

the parameter values of the set of relevant parameters for the test sample are determined from one or more microscopic images of the cells in the test sample; and/or the method further comprises performing a single-cell phenotyping by determining feature values of the set of meta-features and/or parameter values of the set of relevant parameters for at least one of the plurality of cells in the test sample, and/or performing a population-level phenotyping by determining average feature values of the set of meta-features and/or average parameter values of the set of relevant parameters averaged over a set of cells from the plurality of cells in the test sample; and/or the method further comprises determining the set of relevant parameters and the set of meta-features using the method according to any one of examples 1 to 9.

Example 14: A computer program product comprising a set of machine-readable instructions executable by a processing device, wherein the instructions cause the processing device to execute a method according to any one of the preceding examples.

Example 15: A system comprising a processing device and a data storage coupled to the processing device, wherein the data storage stores a set of machine-readable instructions that, when executed by the processing device, cause the processing device to:

receive at least one microscopic image of a test sample of biological cells and at least one microscopic image of a control test sample of biological cells;

determine parameter values of a set of relevant parameters for each of a plurality of cells in the test sample and for each of a plurality of cells in the control test sample from the at least one microscopic image of the respective sample;

determine feature values of a set of meta-features from the parameter values of the set of relevant parameters for the test sample; and determine feature values for the set of meta-features from the parameter values of the set of relevant parameters for the control test sample, wherein the set of relevant parameters and the set of meta-features were determined using the method according to one of examples 1 to 9, wherein the system preferably further comprises the test sample and the control test sample, wherein the test sample is to be exposed to a test substance.

The invention claimed is:

1. A method of studying an effect of a test substance on a test sample of biological cells using a set of relevant parameters and a set of meta-features ($f_1$, $f_2$, $f_L$), the method comprising:

exposing the test sample to the test substance;

determining parameter values of the set of relevant parameters for each of a plurality of cells in the test sample; and determining feature values of the set of meta-features ($f_1$, $f_2$, $f_L$) for the test sample, wherein each of the feature values is calculated from the parameter values of a cluster ($C_1$, $C_2$, $C_L$) of correlated parameters from the set of relevant parameters that is associated with the respective meta-feature ($f_1$, $f_2$, $f_L$), wherein a reference sample for determining the set of meta-features ($f_1$, $f_2$, $f_L$) was exposed to a stimulus substance, wherein each cluster ($C_1$, $C_2$, $C_L$) used for calculating the feature values includes at least one parameter from each of two or more distinct measurement categories; and wherein a correlation structure of the clusters ($C_1$, $C_2$, $C_L$) is validated as consistent across both a control sample and the reference sample, such that only parameters showing robust correlation in both contexts are used for calculating the feature values.

2. The method of claim 1, wherein the set of relevant parameters and the set of meta-features are determined by:

receiving parameter values of a set of cell parameters ($p_1$, $p_2$, $p_N$) for each of a plurality of cells in the control sample and for each of a plurality of cells in the reference sample;

identifying a set of relevant parameters from the set of cell parameters ($p_1$, $p_2$, $p_N$) by comparing the parameter values from the control sample and the parameter values from the reference sample for at least one of the cell parameters ($p_1$, $p_2$, $p_N$);

identifying clusters ($C_1$, $C_2$, $C_L$) of correlated parameters within the set of relevant parameters based on correlations between the parameter values of the relevant parameters; and defining a meta-feature ($f_1$, $f_2$, $f_L$) for at least one of the clusters ($C_1$, $C_2$, $C_L$) as a mathematical function of the parameters of the respective cluster.

3. The method of claim 1, further comprising:

determining parameter values of the set of relevant parameters for each of a plurality of cells in a control test sample;

determining feature values of the set of meta-features ($f_1$, $f_2$, $f_L$) from the parameter values of the set of relevant parameters for the control test sample; and comparing feature values of meta-features ($f_1$, $f_2$, $f_L$) for the test sample and feature values of meta-features ($f_1$, $f_2$, $f_L$) for the control test sample to assess an effect of the test substance.

4. The method of claim 1, wherein the biological cells are cardiomyocytes and the stimulus substance comprises a hypertrophy inducing substance, in particular at least one of phenylephrine, adrenaline, noradrenaline, isoproterenol, insulin, endothelin, and angiotensin and/or a mediator involved in one or more medical conditions, in particular in one or more cardiovascular conditions, and/or the test substance comprises a candidate substance to be tested as a potential inhibitor or modulator of the medical condition.

5. The method of claim 1, wherein the test substance comprises patient-specific material, in particular a blood sample, blood components and/or human-induced pluripotent stem cell-derived cardiomyocytes, iPSC-CMs, in combination with one or more pharmacological substances, wherein the stimulus substance comprises patient specific material of one or more reference patients diagnosed with a medical condition to be tested, in combination with one or more pharmacological substances and/or the stimulus substance comprises patient specific material of one or more reference patients without the medical condition to be tested, in combination with one or more pharmacological substances and/or a mediator involved in one or more medical conditions, in particular in one or more cardiovascular conditions.

6. The method of claim 1, wherein the test substance comprises a sample of a patient, in particular a blood sample of the patient, comprising blood serum or blood plasma of the patient, wherein the method further comprises diagnosing a medical condition, assessing severity of a medical condition, assessing prognosis, and/or assessing a progress of therapeutic treatment against a medical condition based on the feature values of the set of meta-features ($f_1$, $f_2$, $f_L$) for the test sample, in particular wherein the medical condition is hypertrophic cardiomyopathy, amyloidosis, ischemic cardiomyopathy, dilatative cardiomyopathy, hypertensive heart disease, cardiac arrest, and/or aortic stenosis.

7. The method of claim 1, wherein the method is used to distinguish different cell types, in particular to distinguish one or more of: fibroblast, cardiomyocyte, immune cell, or others, and/or to distinguish different cell sub-types, in particular one or more of cardiomyocyte subtypes or target cells for potential therapeutic agents.

8. The method of claim 1, wherein the method further comprises:

assessing suitability of therapeutic treatments for an individual patient, in particular regarding treatment efficacy, adverse events, time to treatment response, wherein the method is used for continuous therapeutic monitoring, and/or assessing a prognosis and/or a probability of major cardiac events and/or a time to major cardiac events and/or a probability of death and/or a time to death, wherein the test substance comprises patient specific material in combination with one or more pharmacological substances, wherein the stimulus substance comprises patient specific material of one or more reference patients with a known prognosis and/or a known probability of major cardiac events and/or a known time to major cardiac events and/or a known probability of death and/or a known time to death, in combination with one or more pharmacological substances.

9. The method of claim 1, wherein: the method further comprises performing a single-cell phenotyping by determining feature values of the set of meta-features ($f_1$, $f_2$, $f_L$) and/or parameter values of the set of relevant parameters for at least one of the plurality of cells in the test sample, and/or performing a population-level phenotyping by determining average feature values of the set of meta-features ($f_1$, $f_2$, $f_L$) and/or average parameter values of the set of relevant parameters averaged over a set of cells from the plurality of cells in the test sample.

10. The method of claim 1, wherein the plurality of cells include one or more of one or more cells extracted from mammalian hearts, in particular one or more of whole heart derived single cell suspensions, cardiomyocytes, fibroblasts, immune cells, and/or one or more mammalian stem-cell derived cardiomyocytes, in particular human induced pluripotent stem cell-derived cardiomyocytes.

11. The method of claim 1, wherein a medical condition is chosen from the field of cardiovascular conditions, in particular wherein the medical condition is hypertrophic cardiomyopathy, amyloidosis, ischemic cardiomyopathy, dilatative cardiomyopathy, hypertensive heart disease, and/or aortic stenosis.

12. The method of claim 1, wherein determining parameter values of the set of relevant parameters for each of a plurality of cells in the test sample comprises obtaining a plurality of images of the plurality of cells at a plurality of time points, wherein in particular the plurality of images are obtained using a microscope.

13. The method of claim 1, further comprising an initial step of staining or labelling the biological cells, a cell compartment, a cell structure, a specific protein or mRNA of interest and/or the test substance with a stain or dye or with an imaging marker.

14. A system comprising a processing device and a data storage coupled to the processing device, wherein the data storage stores a set of machine-readable instructions that, when executed by the processing device, cause the processing device to:

receive at least one microscopic image of a test sample of biological cells and at least one microscopic image of a control test sample of biological cells;

determine parameter values of a set of relevant parameters for each of a plurality of cells in the test sample and for each of a plurality of cells in the control test sample from the at least one microscopic image of the respective sample;

determine feature values of a set of meta-features ($f_1$, $f_2$, $f_L$) from the parameter values of the set of relevant parameters for the test sample; and determine feature values for the set of meta-features ($f_1$, $f_2$, $f_L$) from the parameter values of the set of relevant parameters for the control test sample, wherein the system further comprises the test sample and the control test sample, wherein the test sample is to be exposed to a test substance, wherein each cluster of parameters used for calculating the feature values includes at least one parameter from each of two or more distinct measurement categories; and wherein a correlation structure of the clusters is validated as consistent across both the control test sample and a reference sample, such that only parameters showing robust correlation in both contexts are used for calculating the feature values.

15. The system of claim 14, wherein the set of relevant parameters and the set of meta-features ($f_1$, $f_2$, $f_L$) were determined by:

receiving parameter values of a set of cell parameters ($p_1$, $p_2$, $p_N$) for each of a plurality of cells in a control sample and for each of a plurality of cells in the reference sample;

identifying a set of relevant parameters from the set of cell parameters ($p_1$, $p_2$, $p_N$) by comparing the parameter values from the control sample and the parameter values from the reference sample for at least one of the cell parameters ($p_1$, $p_2$, $p_N$);

identifying clusters ($C_1$, $C_2$, $C_L$) of correlated parameters within the set of relevant parameters based on correlations between the parameter values of the relevant parameters; and defining a meta-feature ($f_1$, $f_2$, $f_L$) for at least one of the clusters ($C_1$, $C_2$, $C_L$) as a mathematical function of the parameters of the respective cluster.

16. A non-transitory computer-readable storage medium comprising instructions stored thereon that, when executed by a computing device cause the computing device to perform operations of studying an effect of a test substance on a test sample of biological cells using a set of relevant parameters and a set of meta-features ($f_1$, $f_2$, $f_L$), the operations comprising:

exposing the test sample to the test substance;

determining parameter values of the set of relevant parameters for each of a plurality of cells in the test sample; and determining feature values of the set of meta-features-for the test sample ($f_1$, $f_2$, $f_L$), wherein each of the feature values is calculated from the parameter values of a cluster ($C_1$, $C_2$, $C_L$) of correlated parameters from the set of relevant parameters that is associated with the respective meta-feature ($f_1$, $f_2$, $f_L$), wherein a reference sample for determining the set of meta-features ($f_1$, $f_2$, $f_L$) was exposed to a stimulus substance, wherein each cluster (C1, C2, CL) used for calculating the feature values includes at least one parameter from each of two or more distinct measurement categories; and wherein a correlation structure of the clusters (C1, C2, CL) is validated as consistent across both a control sample and the reference sample, such that only parameters showing robust correlation in both contexts are used for calculating the feature values.

* * * * *